United States Patent [19]

Ferkol, Jr. et al.

[11] Patent Number: 5,972,901
[45] Date of Patent: Oct. 26, 1999

[54] SERPIN ENZYME COMPLEX RECEPTOR—MEDIATED GENE TRANSFER

[75] Inventors: Thomas W. Ferkol, Jr., Euclid; Pamela B. Davis; Assem-Galal Ziady, both of Cleveland Heights, all of Ohio

[73] Assignee: Case Western Reserve University, Cleveland, Ohio

[21] Appl. No.: 08/656,906

[22] Filed: Jun. 3, 1996

Related U.S. Application Data

[63] Continuation-in-part of application No. 08/655,705, Jun. 3, 1996, which is a continuation of application No. PCT/US95/03677, Mar. 23, 1995, which is a continuation-in-part of application No. 08/216,534, Mar. 23, 1994, abandoned.

[51] Int. Cl.$^6$ .................................................. A01N 43/04
[52] U.S. Cl. ...................... 514/44; 424/93.21; 435/7.8; 435/91.4; 435/320.1; 435/325; 435/455; 530/388.22; 530/887.3; 530/324; 536/23.1
[58] Field of Search .................... 514/44; 424/93.21; 435/7.8, 91.4, 320.1, 325, 172.3, 45, 375, 455; 530/388.22, 887.3, 324; 536/23.1

[56] References Cited

U.S. PATENT DOCUMENTS

| 5,108,921 | 4/1992 | Low et al. | 435/325 |
|---|---|---|---|
| 5,166,320 | 11/1992 | Wu et al. | 530/395 |
| 5,354,844 | 10/1994 | Beug et al. | 530/345 |

FOREIGN PATENT DOCUMENTS 0 551118 A2  10/1992  European Pat. Off. .

OTHER PUBLICATIONS

Ledley, Human Gene Therapy. 1995, 6:1129–1144.
Coghlan. New Scientist, Nov. 1995:14–15.
Laemmli et al. P.N.A.S. 1975, vol. 72, 11:4288–4292.
Wagner et al., *Proc. Natl. Acad. Sci.*, 88:4255–4259 (1991).
Dubensky et al., *Proc. Nat. Acad. Sci. USA*, 81:7529–33 (1984).
Benvenisty and Reshef, *Proc. Nat. Acad. Sci. USA*, 83:9551–55 (1986).
Wolff et al., *Science*, 247:1456–68 (1990).
Acsadi et al., *New Biologist*, 3:71–81 (1991).
Maniatis et al., *Science*, 236:1237 (1987).
Voss et al., *Trends Biochem. Sci.*, 11:287 (1986).
Dijkema et al., *EMBO J.* 4:761 (1985).
Uetsuki et al., *J. Biol. Chem.*, 264:5791 (1989).
Kim et al., *Gene* 91:217 (1990).
Mizushima and Nagata, *Nuc. Acids. Res.*, 18:5322 (1990).
Gorman et al., *Proc. Natl. Acad. Sci. USA* 79:6777 (1982).
Boshart et al., *Cell* 41:521 (1985).
Ennever et al., *Biochem. Biophys. Acta,* 826:67 (1985).
Kasahara et al. (1994) *Science* 266:1373.
Valesia–Wittmann et al. (1994) *J. Virol.* 68:4609.
Miller et al., *Biochemistry* 20:1874–1880 (1981).
Miller et al., *Biochemistry*, 18:5134–43 (1979).
Matsukura et al., *Proc. Nat. Acad. Sci.,* 84:7706–10 (1987).
Zerial et al., Nucleic Acids Res., 15:9909–19 (1987).
Leonetti et al., *Gene*, 72:32–33 (1988).
Monsigny et al. Biol. Cell., 51:187 (1984).
Ferkol et al., *FASEB J.,* 7:1081 (1993).
Schlepper–Schäfer, J. et al., *Exp. Cell. Res.* 165:494 (1986).
Bijsterbosch, M.K. et al., *Mol. Pharmacol* 36:484 (1989).
Bijsterbosch, M.K. et al., *Mol. Pharmacol* 41:404 (1992).
Perales et al., *Proc. Natl. Acad. Sci. USA*. 91:4086 (1994).
Kobayashi, *Immunochemistry* 8: 785–800 (1971).
Harlow and Lane,*Antibodies: A Laboratory Manual,* Cold Spring Harbor Laboratory Press, Cold Spring Harbor, NY, pp. 196–223 (1988).
Fiedler et al., *Am J. Physiol* 261:L255 (1991).
Morrison and Oi, *Adv. Immunol.* 44:76 (1989).
Shin and Morrison, *Methods Enzymol.* 178:459 (1989).
Bird et al., *Science* 242:423 (1988).
Huston et al., *Proc. Natl. Acad. Sci. USA* 85:5879 (1988).
Batra et al.,*Mol. Cell. Biol.* 11:22 (1989).
Chaudhary et al. (1989) *Nature* 339:394.
Chaudhary et al., *Proc. Natl. Acad. Sci. USA* 87:949 (1990).
Pantoliano et al., *Biochem.* 30:10118 (1991).
Nicholls et al., *J. Immunological Methods* 165:81(1993).
Johnson and Bird, *Methods in Enzymol.* 203:88 (1991).
Johnson et al.,*Biochem. Biophys. Acta* 950:45 (1988).
Huston et al. *Proc. Natl. Acad. Sci. USA* 85:5879 (1988).
Pantoliano et al., *Biochem.* 30:10117 (1991).
Perlmutter, *Pediatric Res.* 36:271–277 (1994).
Enghild et al., *J. Biol. Chem.* 269:20159–20166 (1994).
Perlmutter et al., *J. Biol. Chem.* 265:16713–16716 (1990).
Perlmutter et al., *Proc. Natl. Acad. Sci. USA* 87:3753–3757 (1990).
Kahlil et al., *Brain Res.* 651:227–235 (1994).
Joslin et al., *J. Biol. Chem.* 266:11282–11288 (1991).
Joslin et al., *J. Biol. Chem.* 268:1886–1893 (1993).
Joslin et al., *J. Biol. Chem.* 266:21897–21902 (1991).
Boland et al., *J. Biol. Chem.* 270:28022–28028 (1995).
Perlmutter, Pediatric Res. 36:271 (1994).
Bu et al., J. Biol. Chem. 267:15595 (1992).
Ferkol et al., *J. Clin. Invest.* 92:2394 (1993).
Lin and Culp, *Biotechniques* 11:344–351 (1991).
Ferkol et al., *Proc. Natl. Acad. Sci. USA* 93:101 (1996).
Hunter and Greenwood, *Nature* 194:49 (1962).
Brasier et al., *BioTechniques* 7:1116–1122 (1989).
Lim and Chase *Biotechniques* 7:576–579 (1989).
Mann and Fish ,*Methods of Enzymology* 26:28–42 (1972).
Wu and Wu, *J Biol Chem* 262:44299 (1991).
Wu et al., *J. Biol. Chem.* 266:14338 (1990).
Ferkol et al., *J. Clin. Invest.* 95:493 (1995).

*Primary Examiner*—Bruce R. Campell
*Assistant Examiner*—Dave Trong Nguyen
*Attorney, Agent, or Firm*—Banner & Witcoff, Ltd.

[57] ABSTRACT

Nucleic acids are compacted, substantially without aggregation, to facilitate their uptake by target cells of an organism to which the compacted material is administered. The nucleic acids may achieve a clinical effect as a result of gene expression, hybridization to endogenous nucleic acids whose expression is undesired, or site-specific integration so that a target gene is replaced, modified or deleted. The targeting may be enhanced by means of a target cell-binding moiety. The nucleic acid is preferably compacted to a condensed state.

22 Claims, 29 Drawing Sheets

OTHER PUBLICATIONS

Perales et al., *Proc. Natl. Acad. Sci. USA*. 91:4086 (1994).

Chen et al., "Design of a genetic immunotoxin to eliminate toxin immunogenicity," Gene Therapy 2:116 (1995).

Barinaga, "Step Taken Toward Improved Vectors for Gene Transfer," Science 266:1326 (1994).

Shin et al., "Transferrin–antibody fusion proteins are effective in brain targeting," Proc. Nat. Acad. Sci. 92:2820 (1995).

Shin and Morrison, "Expression and characterization of an antibody binding specificity joined to insulin–like growth factor 1: Potential applications for cellular targeting," Proc. Nat. Acad. Sci. 87:5322 (1990).

Wagner et al., "Transferrin–polycation conjugates as carriers for DNA uptake," Proc. Nat. Acad. Sci. 87:3410 (1990).

Zenke et al., "Receptor–mediated endocytosis of transferrin–polycation conjugates: An efficient way to introduce DNA into hematopoietic cells," Proc. Nat. Acad. Sci. 87:3655 (1990).

Ferkol et al., "Targeted Gene Delivery To Respiratory Epithelial Cells," Abstract at 1992 Cystic Fibrosis Conference.

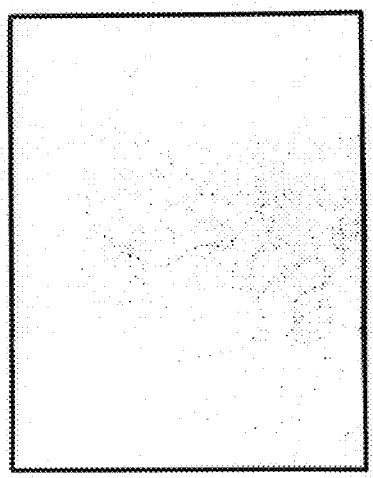
FIG. 1B
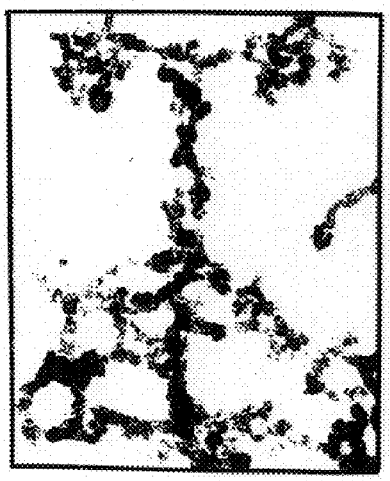
FIG. 1C
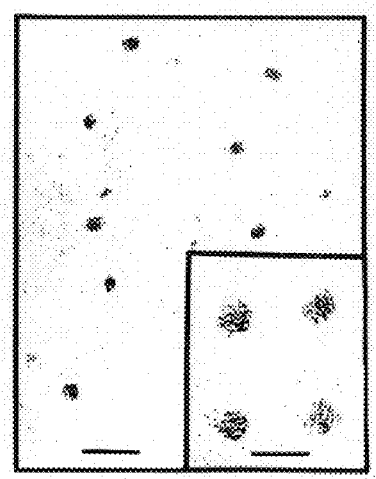
FIG. 1D
FIG. 1E

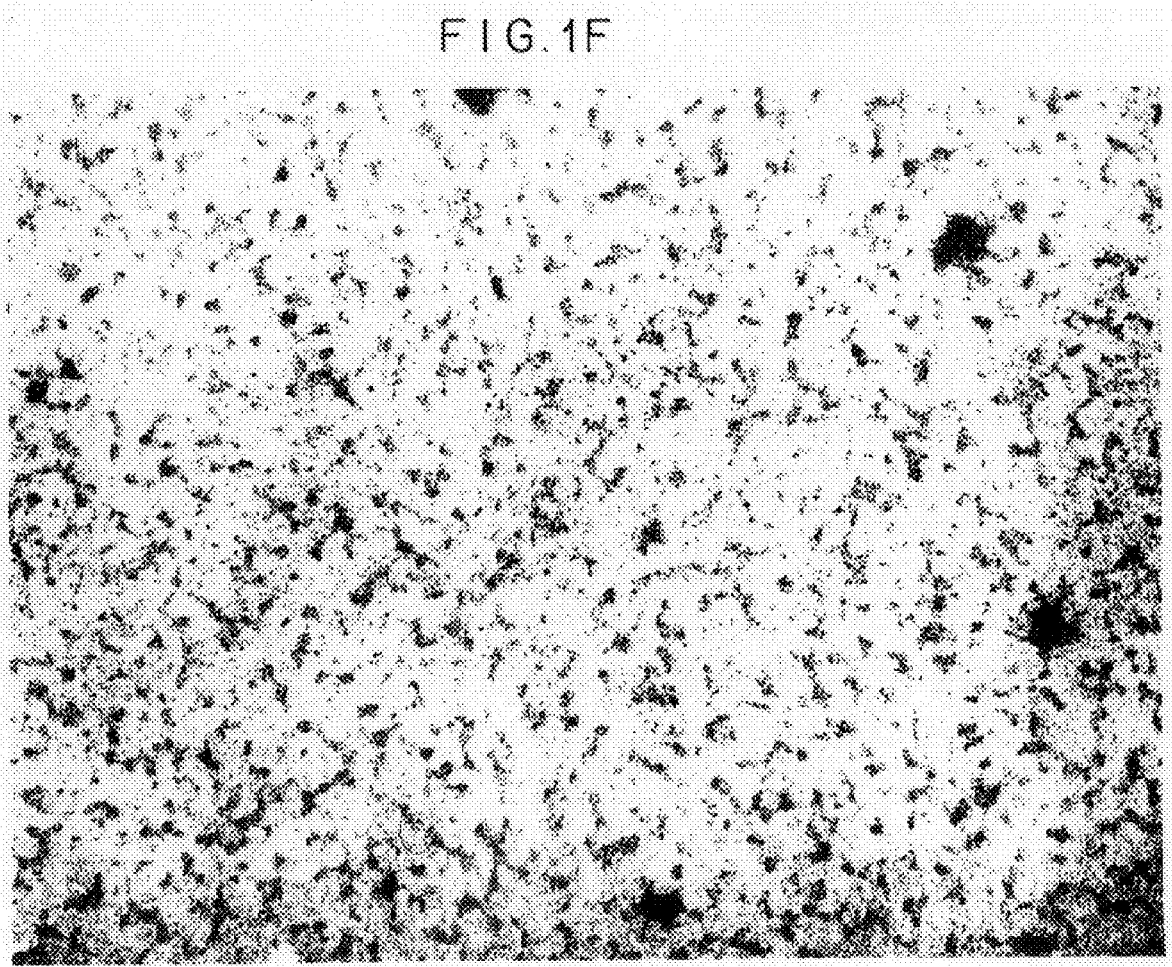

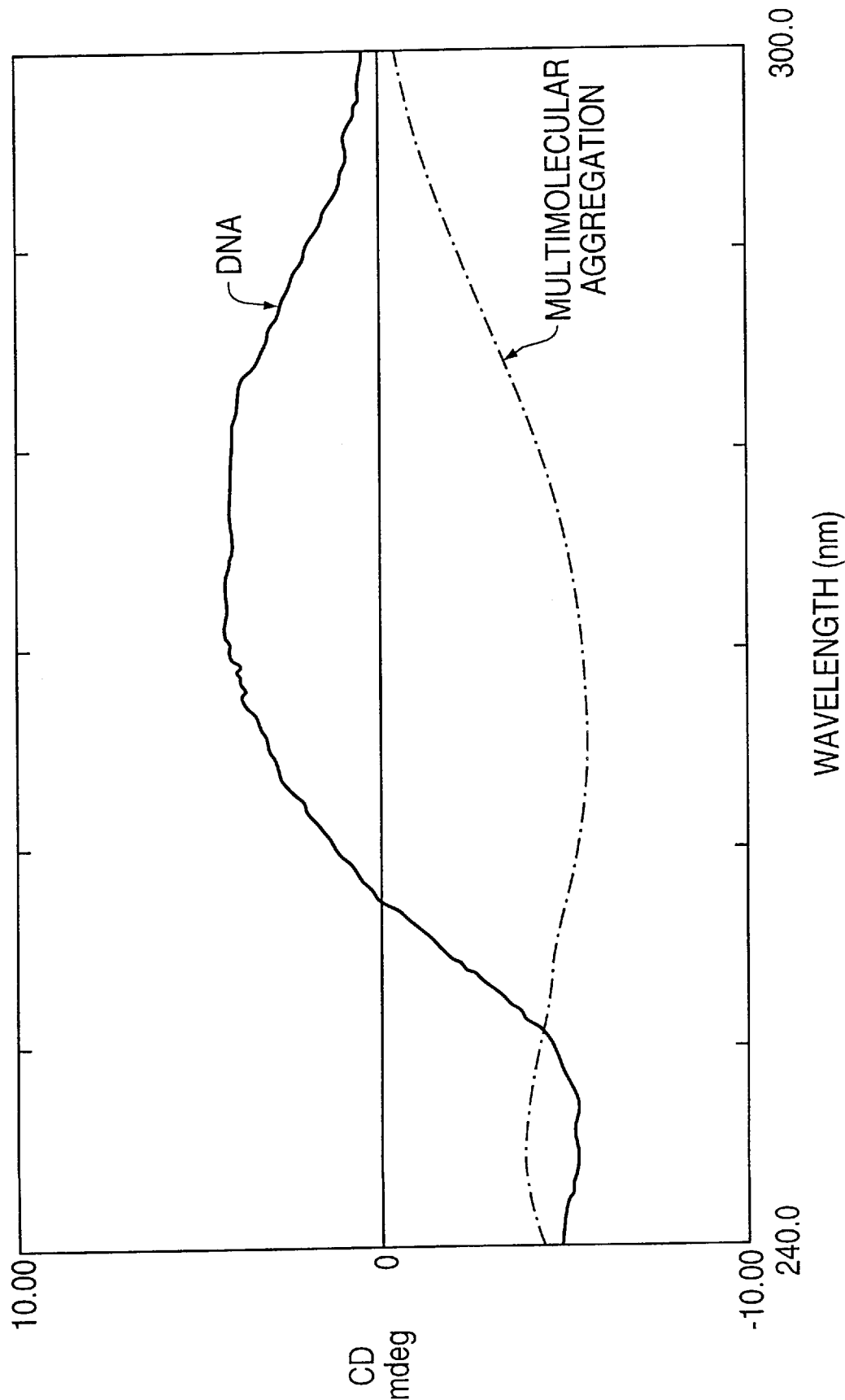

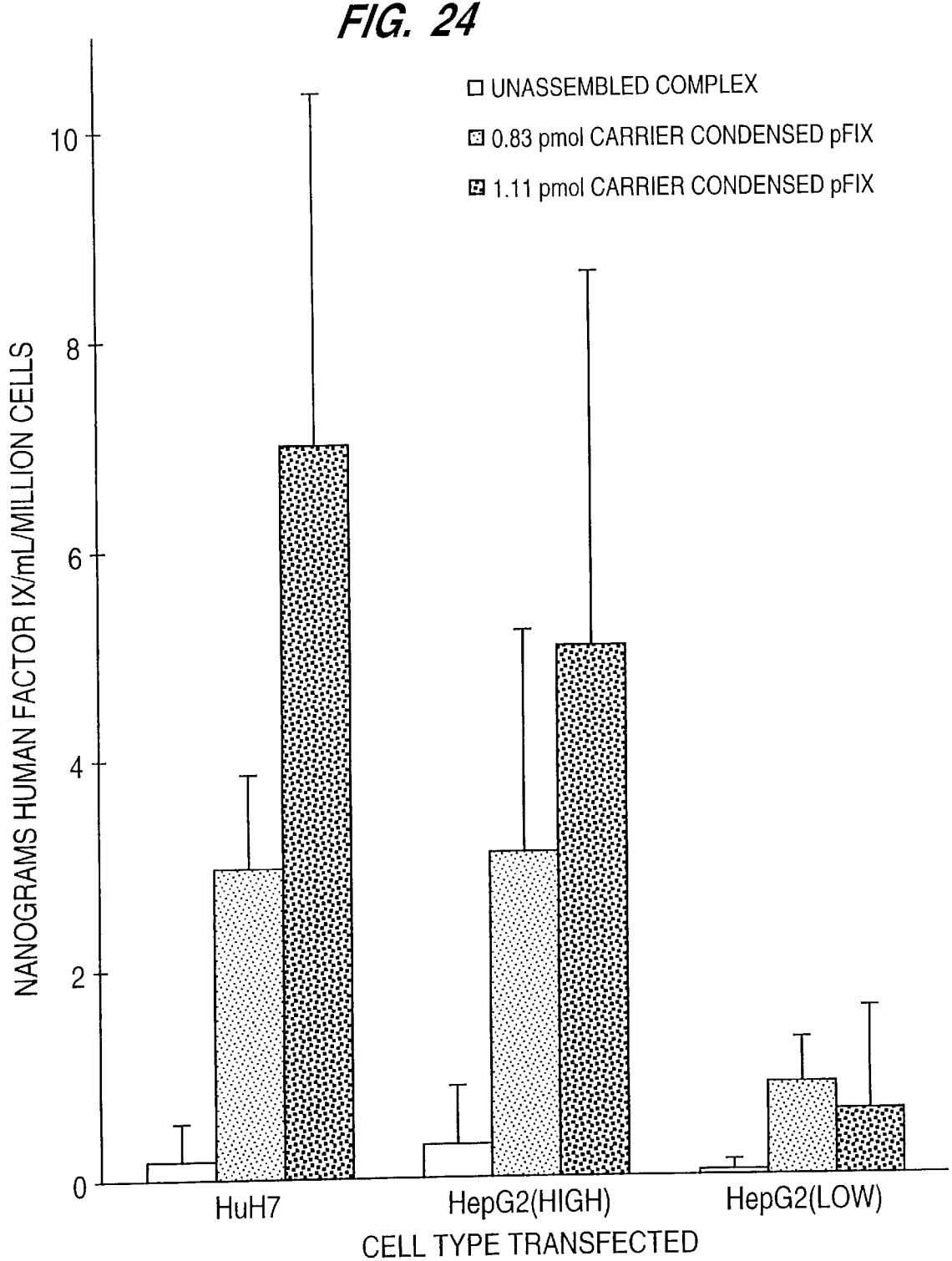

SERPIN ENZYME COMPLEX RECEPTOR—MEDIATED GENE TRANSFER

This application is a Continuation-In-Part of application Ser. No. 08/655,705, filed Jun. 3, 1996 pending which is a Continuation of PCT application Ser. No. PCT/US95/03677, filed Mar. 23, 1995, which is a Continuation-In-Part of application Ser. No. 08/216,534, filed Mar. 23, 1994, abandoned, hereby incorporated by reference in its entirety.

This invention was made with government support under Grant Nos. DK 49138 and DK 43999 awarded by the National Institutes of Health, Department of Health and Human Services. The Government has certain rights in the invention.

FIELD OF THE INVENTION

The present invention relates to the in vivo delivery of exogenous nucleic acids to cells of multicellular organisms. In particular, the present invention relates to the delivery of exogenous nucleic acids to cells having a serpin enzyme complex receptor on their surface.

BACKGROUND

Functional exogenous genes can be introduced to mammalian cells in vitro by a variety of physical methods, including transfection, direct microinjection, electroporation, and coprecipitation with calcium phosphate. Most of these techniques, however, are impractical for delivering genes to cells within intact animals.

Receptor-Mediated Uncompacted DNA Delivery In Vivo

Receptor-mediated gene transfer has been shown to be successful in introducing transgenes into suitable recipient cells, both in vitro and in vivo. This procedure involves linking the DNA to a polycationic protein (usually poly-L-lysine) containing a covalently attached ligand, which is selected to target a specific receptor on the surface of the tissue of interest. The gene is taken up by the tissue, transported to the nucleus of the cell and expressed for varying times. The overall level of expression of the transgene in the target tissue is dependent on several factors: the stability of the DNA-carrier complex, the presence and number of specific receptors on the surface of the targeted cell, the receptor-carrier ligand interaction, endocytosis and transport of the complex to the nucleus, and the efficiency of gene transcription in the nuclei of the target cells.

Wu, et al., U.S. Pat. No. 5,166,320, discloses tissue-specific delivery of DNA using a conjugate of a polynucleic acid binding agent (such as polylysine, polyarginine, polyornithine, histone, avidin, or protamine) and a tissue receptor-specific protein ligand. For targeting liver cells, Wu suggests "asialoglycoprotein (galactose-terminal) ligands".

Wagner, et al., Proc. Natl. Acad. Sci., 88:4255–4259 (1991) and U.S. Pat. No. 5,354,844 disclose complexing a transferrin-polylysine conjugate with DNA for delivering DNA to cells via receptor mediated endocytosis. Wagner, et al., teach that it is important that there be sufficient polycation in the mixture to ensure compaction of plasmid DNA into toroidal structures of 80–100 nm diameter, which, they speculate, facilitate the endocytic event.

Direct Injection Of Naked, Uncompacted DNA

The possibility of detecting gene expression by directly injecting naked DNA into animal tissues was demonstrated first by Dubenski et al., Proc. Nat. Acad. Sci. USA, 81:7529–33 (1984), who showed that viral or plasmid DNA injected into the liver or spleen of mice was expressed at detectable levels. The DNA was precipitated using calcium phosphate and injected together with hyaluronidase and collagenase. The transfected gene was shown to replicate in the liver of the host animal. Benvenisty and Reshef, Proc. Nat. Acad. Sci. USA, 83:9551–55 (1986) injected calcium phosphate precipitated DNA intraperitoneally into newborn rats and noted gene expression in the livers of the animals 48 hours after transfection. In 1990, Wolff et al., Science, 247:1456–68 (1990), reported that the direct injection of DNA or RNA expression vectors into the muscle of mice resulted in the detectable expression of the genes for periods for up to 2 months. This technique has been extended by Acsadi et al., New Biologist, 3:71–81 (1991) to include direct injection of naked DNA into rat hearts; the injected genes were expressed in the heart of the animals for up to 25 days. Other genes, including the gene for dystrophin have been injected into the muscle of mice using this technique. This procedure forms the base of a broad approach for the generation of immune response in an animal by the administration of a gene by direct injection into the target tissue. The gene is transiently expressed, producing a specific antigen. (See Donnelly et al., The Immunologist, 21, pp. 20–26 (1994) for a recent review). However, the DNA used in these experiments has not been modified or compacted to improve its survival in the cell, its uptake into the nucleus or its rate of transcription in the nucleus of the target cells.

SUMMARY OF THE INVENTION

The present invention relates to the delivery of exogenous nucleic acids to cells, including but not limited to the cells of multicellular organisms. When the nucleic acid includes an expressible gene, that gene can be expressed in the cell. In some embodiments, a tissue-specific carrier molecule is prepared, which is a bifunctional molecule having a nucleic acid-binding moiety and a target tissue-binding moiety.

The nucleic acid can be compacted at high concentrations with the carrier molecule at a critical salt concentration. The nucleic acid-loaded carrier molecule is then administered to the organism.

In one embodiment, the present invention contemplates a method for delivering an oligonucleotide to a mammalian cell, comprising the steps of: a) providing: i) a target binding moiety capable of binding to a serpin enzyme complex receptor; ii) a nucleic acid binding moiety; iii) an expression vector comprising an oligonucleotide encoding one or more gene products; iv) a mammalian cell having on its exterior surface a serpin enzyme complex receptor; b) conjugating the target binding moiety to the nucleic acid binding moiety to form a carrier; c) coupling the expression vector with the carrier to form a pharmaceutical composition; and d) contacting the mammalian cell with the pharmaceutical composition under conditions such that the pharmaceutical composition binds to the receptor and results in delivery of the pharmaceutical composition to the interior of the mammalian cell. It is preferred that the expression vector (i.e., the nucleic acid or oligonucleotide encoding one or more gene products) is compacted. The compaction of nucleic acids (e.g., expression vectors) associated with a carrier comprising a conjugate between a TBM and a NABM is described in detail herein. Preferably, the pharmaceutical compound comprising the carrier and the expression vector are compacted to a diameter of less than 100 nm, preferably less than 80 nm and most preferably having a diameter of about 10 to 25 nm, with a diameter of about 15 to 25 nm being particularly preferred.

As used herein, a "pharmaceutical composition" is a composition comprising an aggregate (i.e., a complex) between an expression vector (i.e., a nucleic acid molecule) and a carrier comprising a target binding moiety conjugated to a nucleic acid binding moiety. The pharmaceutical composition may further comprise a pharmaceutically acceptable excipient. The terms "pharmaceutical composition" and therapeutic composition" are used herein interchangeably. It is not intended that the pharmaceutical compositions be limited to any particular expression vector, carrier or exciepient.

In a preferred embodiment, the expression vector further comprises a promoter sequence operably linked to the oligonucleotide encoding one or more gene products. The present invention is not limited by the nature of the promoter sequence employed.

Any promoter sequence which is functional in the target cell (i.e., the cell expressing a serpin enzyme complex (SEC) receptor on its exterior surface), may be employed to achieve expression of the gene(s) of interest. The promoter sequence may be from a mammalian gene, including but not limited to the gene encoded by the expression vector (i.e., the gene(s) of interest present on the expression vector may be under the transcriptional control of their native or endogenous promoter).

The promoter sequence may be derived (i.e., obtained or isolated) from a gene expressed in all mammalian cells (i.e., a constitutive or ubiquitous promoter) such as β-acitin, human elongation factor 1α gene, etc. Alternatively, the promoter may be derived from a gene which is expressed in a tissue-specific manner so long as the promoter is active in the target cell. For example, when liver cells are the target cells, promoters derived from genes expressed in the liver such as phosphoenol pyruvate carboxykinase, albumin, metallothionein, surfactant, apoE, pyruvate kinase, LDL receptor, HMG CoA reductase, etc. may be employed.

Alternatively, the promoter may be derived from viral sequences, such as viral long terminal repeats (LTRs), which are expressed in a variety of cell types. For example, the LTR of the Rous sarcoma virus (RSV), Moloney murine leukemia virus (MoMLV) and the human cytomegalovirus (CMV) may be used in the present invention. However, it is not intended that the viral promoter be limited to a particular viral promoter as various promoters may be used in the present invention.

The expression vector may also comprise an enhancer sequence. Transcriptional control signals in eucaryotes comprise "promoter" and "enhancer" elements or sequences. Promoters and enhancers consist of short arrays of DNA sequences that interact specifically with cellular proteins involved in transcription [Maniatis, et al., *Science* 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss, et al., *Trends Biochem. Sci.*, 11:287 (1986) and Maniatis, et al., supra (1987)]. For example, the SV40 early gene enhancer is very active in a wide variety of cell types from many mammalian species and has been widely used for the expression of proteins in mammalian cells [Dijkema, et al., *EMBO J.* 4:761 (1985)]. Two other examples of promoter/enhancer elements active in a broad range of mammalian cell types are those from the human elongation factor lot gene [Uetsuki et al., *J. Biol. Chem.*, 264:5791 (1989); Kim et al., *Gene* 91:217 (1990); and Mizushima and Nagata, *Nuc. Acids. Res.*, 18:5322 (1990)], the LTRs of the Rous sarcoma virus [Gorman et al., *Proc. Natl. Acad Sci. USA* 79:6777 (1982)], and the human cytomegalovirus [Boshart et al., *Cell* 41:521 (1985)].

The enhancer and/or promoter sequences employed may be "endogenous" or "exogenous" or "heterologous." An endogenous enhancer or promoter is one which is naturally linked with a given gene in the genome. An exogenous (heterologous) enhancer or promoter is one which is placed in juxtaposition to a gene by means of genetic manipulation (i.e., molecular biological techniques).

In one embodiment, the target binding moiety is a peptide comprising a recognition sequence for the SEC receptor. As used herein, the term "recognition sequence for the SEC receptor" means a peptide sequence which is capable of acting as a ligand for the SEC receptor. Peptides comprising the pentapeptide binding domain FVF/YLI (SEQ ID NOS:28 and 29) are preferred recognition sequences. However, the present invention is not limited by the nature of the peptide comprising the recognition sequence; any peptide capable of binding to and mediating internalization via the SEC receptor is contemplated. In a preferred embodiment, the recognition sequence is selected from the group comprising SEQ ID NOS:28 and 29. In another embodiment, the target binding moiety is a peptide having the amino acid sequence set forth in SEQ ID NO:31.

It is not intended that the present invention be limited by the nature of the nucleic acid binding moiety. In one embodiment, the nucleic acid binding moiety is a polycation, such as poly-L-lysine. Other nucleic acid binding moieties including, but not limited to protamines, polyarginine, avidin (employed when the expression vector comprises biotin moieties), polyornithine, and histones may be employed.

The term "polycation" as used herein refers to a peptide or polypeptide (i.e., protein) sequence which contains an abundance of amino acid residues having positively charged (i.e., basic) side chains (e.g., arginine and lysine) such that the peptide has a positive charge and is capable of binding ionically to nucleic acids (which are negatively charged). Preferably the polycation comprises at least 4 amino acid residues.

The present invention is not limited by the location of the recipient or target cell. The target cell may be a cultured cell or more preferably the cell may be located in a recipient animal, including a human. In a preferred embodiment, the recipient mammalian cell is selected from the group consisting of hepatocytes, mononuclear phagocytes, neutrophils, intestinal epithelial cells, glial cells and neuronal cells.

In a preferred embodiment, the contacting of the mammalian cell with the pharmaceutical (i.e., therapeutic) composition comprises administrating the complex to the recipient animal. The present invention is not limited by the nature of the administration of the composition. In one embodiment, the administration comprises injection of an aqueous solution containing the pharmaceutical composition into the recipient animal (e.g., by intravenous injection).

The present invention can be used with success with a variety of animals. Particular therapeutic success is achieved with humans. In that regard, it may be desirable, following injection of the composition, to examine the relevant tissue expressing a SEC receptor on its exterior surface for the expression of the one or more gene products encoded by the expression vector.

In a preferred embodiment, the method of the present invention further comprises, following contacting the mammalian cell with the pharmaceutical composition, examining the contacted cell for the expression of the one or more gene products encoded by the expression vector.

The present invention further provides a composition comprising a nucleic acid binding moiety and a target binding moiety, the target binding moiety being capable of binding to a serpin enzyme complex receptor present on the surface of a mammalian cell. In one embodiment, the target binding moiety is a peptide comprising a recognition sequence for the SEC receptor. The present invention is not limited by the nature of the peptide comprising the recognition sequence; any peptide capable of binding to and mediating internalization via the SEC receptor is contemplated. In a preferred embodiment, the recognition sequence is selected from the group comprising SEQ ID NOS:28 and 29. In another embodiment, the target binding moiety is a peptide having the amino acid sequence set forth in SEQ ID NO:31.

It is not intended that the present invention be limited by the nature of the nucleic acid binding moiety. In one embodiment, the nucleic acid binding moiety is a polycation, such as poly-L-lysine. Other nucleic acid binding moieties such as protamines, polyarginine, avidin (employed when the expression vector comprises biotin moieties), polyornithine,and histones may be employed.

The present invention also provides a fusion protein comprising a target binding moiety capable of binding to a serpin enzyme complex receptor present on the surface of a mammalian cell and a nucleic acid binding moiety. In one embodiment, the target binding moiety is a peptide comprising a recognition sequence for the SEC receptor. The present invention is not limited by the nature of the peptide comprising the recognition sequence; any peptide capable of binding to and mediating internalization via the SEC receptor is contemplated. In a preferred embodiment, the recognition sequence is selected from the group comprising SEQ ID NOS:28 and 29. In another embodiment, the target binding moiety is a peptide having the amino acid sequence set forth in SEQ ID NO:31.

The present invention is not limited by the nature of the nucleic acid binding moiety present on the fusion protein. In a preferred embodiment, the nucleic acid binding moiety comprises at least a portion of a protamine protein. The invention is not limited by the source of the protamine; protamine isolated from a variety of sources (e.g., rat, mouse, human, fish, etc.) is contemplated.

The fusion proteins of the present invention may be produced using a variety of approaches known to the art, including but not limited to chemical synthesis of the desired peptide sequence or expression of the desired fusion protein by molecular biological means (i.e, construction of an expression vector containing a coding region encoding the desired fusion protein).

The fusion proteins of the present invention may further comprise a spacer or linker sequence between the target binding moiety capable of binding to a SEC receptor and the nucleic acid binding moiety. The spacer preferably contains 0 to 30 amino acid residues.

The present invention further contemplates fusion proteins comprising a target binding moiety capable of binding to a SEC receptor and a portion of a protein having therapeutic properties, such as an enzymatic activity, cytokine activity and antibiotic activity (e.g., a peptide antibiotic). These fusion proteins are capable of delivering the therapeutic activity to cells expressing the SEC receptor on their surface.

Still further, the present invention contemplates the production of retrovirus particles comprising modified (i.e., chimeric) envelope proteins containing protein sequences comprising a target binding moiety capable of binding to a SEC receptor. Retrovirus particles bearing these modified envelope proteins may be used to deliver genes of interest to cells expressing the SEC receptor.

BRIEF DESCRIPTION OF THE DRAWINGS

FIG. 1A—Physical characterization of the galactose-poly-L-lysine/DNA complexes. FIG. 1A shows CD spectra associated with normal DNA in solution and with certain poly-L-lysine/DNA complexes. Sixty micrograms of RNA-free CMV-β-galactosidase plasmid (dissolved in TE buffer, pH 8), 150 μl of 700 mM NaCl were vortexed at medium speed in a VIBRAX apparatus (IKA-VIBRAX-VXR). Nineteen micrograms of α-galactopyranosyl-phenyl isothiocyanate/poly-L-lysine biconjugate in 150 μl of 700 mM NaCl were added dropwise to the vortexing solution of DNA. The slow addition of the polycation results in the formation of a turbid solution which is dissolved by the slow, stepwise addition of 3 μl aliquots of 5M NaCl. The disappearance of the turbidity was monitored by eye and the solutions of DNA/poly-L-lysine complexes were investigated by CD. At this point (0.97M NaCl), the CD spectrum was that characteristic of aggregated DNA. Further addition of 2 μl aliquots of 5M NaCl (resulting in a concentration of 1.031M NaCl) yielded the CD spectrum expected for a condensed (or a relaxed) DNA complex. The CD spectrum of uncomplexed double stranded DNA at 1M NaCl was also taken. The spectra were obtained using a JASCO-600 spectropolarimeter with a 0.1 cm cuvette. The spectrum of the buffer was subtracted in each case.

FIG. 1B–1G are electronic micrographs (EM). 1B–1D, 1F and 1G are taken at 300,000×. The bar in 1D represents 33.3 nm. FIG. 1E was taken at 600,000×, and the bar is 16.6 nm long. Uranyl acetate staining was performed as previously described. (Ennever, et al., *Biochem. Biophys. Acta*, 826:67 (1985)). Briefly, the grid was subjected to glow discharge prior to staining. A drop of DNA solution was added to the grid, blotted and stained using 0.04% uranyl acetate.

For the EM studies shown in FIGS. 1B–1F, 60 μg of PEPCK-hFIX plasmid DNA (dissolved in TE buffer, pH 8), in 150 μl of 700 mM NaCl were vortexed at medium speed in a VIBRAX apparatus (IKA-VIBRAX-VXR). Nineteen micrograms of α-galactopyranosyl-phenyl isothiocyanate/poly-L-lysine bioconjugate in 150 μl of 700 mM NaCl were added dropwise to the vortexing solution of DNA. The slow addition of the polycation results in the formation of a turbid solution which is dissolved by the slow, stepwise addition of 3 μl aliquots of 5M NaCl. The disappearance of the turbidity was monitored by eye and the solution of DNA/poly-L-lysine complexes was investigated by EM (FIG. 1C). Further addition of 2 μl aliquots of 5M NaCl resulted in structural changes as shown in FIGS. 1D and 1E.

FIG. 1B is an EM of uncomplexed DNA (1 μg/ml at 1M NaCl). FIG. 1C depicts a DNA complex at a suboptimal concentration of NaCl (760 mM). The DNA is in the aggregated state; clusters of unimolecular toroids are visible. In FIG. 1D the DNA complex is at an optimal concentration of NaCl for the complex in question (968 mM). The DNA is properly condensed; only individual toroids can be seen. For FIG. 1E, four complexes of DNA from FIG. 1D were selected and printed at higher magnification.

In FIG. 1F, we see a DNA complex, at a concentration of 1.068M NaCl, which is above optimal for condensation of this complex. The DNA is in the relaxed state. Note the branched unimolecular toroids in which a nucleus of condensation is visible and the rod-like DNA fibers.

Differences in concentration of NaCl required for aggregated, condensed, and relaxed states in the above experiments represent DNA or polycation specific differences.

In a third experiment, complexes of CMV-β-galactosidase and galactosylated poly-L-lysine were formed essentially as in Wu et al. Briefly, plasmid DNA and galactosylated poly-L-lysine were combined in 3M NaCl. The samples were incubated for 1 hour at room temperature, then dialyzed against 0.15M NaCl for 16 hr through membranes with a 3,500-dalton molecular mass limit. On visual inspection, no precipitates were present in the dialysate.

FIG. 1G is an electron micrograph of the resulting DNA complex, which is in the multimolecular aggregated state. Note that the toroids here are larger than in 1C or 1D (the scale is the same). FIG. 1H shows the CD spectrum from 240 to 300 nm for uncomplexed DNA and for aggregated multimolecular DNA/poly-L-Lys complexes, so as to highlight the inversion of the normal DNA spectrum maximum at 269 nm. This inversion is characteristic of multimolecular aggregation.

In another experiment, sixty micrograms of PEPCK-hFIX plasmid DNA (dissolved in TE buffer, pH 8), in 150 μl of 200 mM NaCl were vortexed at medium speed in a VIBRAX apparatus (IKA-VIBRAX-VXR). Nineteen micrograms of α-galactopyranosyl-phenyl isothiocyanate/poly-L-lysine biconjugate in 150 μl of 200 mM NaCl were added dropwise to the vortexing solution of DNA. The addition of the polycation resulted in the formation of precipitates on visual inspection.

FIG. 1I is a CD spectrum, given by a precipitated DNA complex. It is essentially flat from 240 to 300 nm. FIG. 1J is an electron micrograph of the precipitated DNA.

FIG. 2A and 2B —Functional relevance and specificity of the gene transfer system. (A) The relative concentration of human factor IX in the blood of animals treated with the DNA complex was evaluated by measuring the procoagulant activity of human factor IX. A modification of the one stage, kaolin-activated, partial thromboplastin time with factor IX-deficient human plasma was used. Blood samples were obtained from experimental animals by venipuncture. One fiftieth volume of 500 mM sodium citrate, pH 5.0, was added to prevent coagulation, and the plasma was stored at −20° C. The samples were assayed in duplicate, and their activity was compared to the functional activity of pooled plasma from 24 normal adult human males. In all calculations, one unit of factor IX activity in one ml of normal human plasma is equivalent to 100% functional activity or approximately 3 μg of factor IX per ml. Background human factor IX activity in the rat plasma was subtracted prior to graphic representation. (B) Transfected animals were fed a carbohydrate-free/high protein diet for one week. Blood samples were taken at the initiation of the treatment and after one week on the diet and analyzed by Western blot hybridization. The animals at 8 and 12 days were compared with transfected rats fed a standard chow diet. The data were obtained by densitometric analysis of Western blot photographic films and indicate fold increase in human factor IX protein after the dietary treatment.

FIG. 3—Tissue specificity of mannosylated DNA complex in targeting DNA to the macrophages in vivo. Mannosylated poly-L-lysine was conjugated to SV40/luciferase DNA. 300 μg of the DNA complex were introduced into the caudal vena cava of rats. Four days after injection tissue extracts were made and assayed for luciferase activity. The luciferase activity is plotted as Integrated Light Units per milligram of protein extract from spleen, liver and lung. In other tissues no activity was found. Data are expressed as means±standard error of the mean (SEM). The light bars are the non-transfected controls (n=4), and the dark bars, animals transfected with mannosylated poly-L-lysine/DNA complexes (n=5).

FIG. 4—Specificity of mannosylated DNA complex in targeting DNA to primary culture of macrophages in vitro. Primary cultures of peritoneal macrophages were transfected with either galactosylated poly-L-lysine (light bars) or mannosylated poly-L-lysine (dark bars) conjugated to a SV40/luciferase DNA. At the indicated times (2, 4, 8, and 24 hours) cells were washed. Twenty-four hours after transfection, cells were harvested and assayed for luciferase activity. The luciferase activity is plotted as Relative Luciferase Activity after being standardized by the activity found in untransfected controls. Data are expressed as means±standard error of the mean (SEM).

FIG. 5—Competition between the mannosylated DNA complex and mannosylated bovine serum albumin for binding to the Mannose receptor of macrophages. Primary culture of peritoneal macrophages were transfected with mannosylated poly-L-lysine conjugated to SV40/luciferase DNA (T). Prior to the addition of the DNA complex a 100-fold excess mannosylated bovine serum albumin was added to one set of plates (Tc). Non-transfected controls (NT) were also assayed for luciferase activity 24 hours after transfection. The luciferase activity is plotted as Relative Luciferase Activity after being standardized relative to the activity found in untransfected controls. Data are expressed as means±standard error of the mean (SEM).

FIG. 6—In vivo gene transfer using the anti-rat plg-R Fab-poly-L-lysine conjugated DNA complex. Fab-poly-L-lysine was conjugated to SV40/luciferase DNA and introduced into the caudal vena cava of rats (Transfected) (n=3). Untransfected controls (Control) (n=3), animals injected with an Fab-poly-L-lysine-DNA complex containing an Fab fragment obtained from an irrelevant IgF (IFab) (n=3), and animals injected with a DNA complex that does not contain an SV40/Luciferase gene (IDNA) (n=3), were run as controls. Two days after injection tissue extracts were prepared and assayed for luciferase activity. The luciferase activity is plotted as Integrated Light Units per milligram of protein extract. Data are expressed as means±standard error of the mean (SEM).

FIG. 7—Time-course of expression in lung and liver of animals injected using the anti-rat plg-R Fab-poly-L-lysine conjugated DNA complex. Fab-poly-L-lysine was conjugated to SV40/luciferase DNA and introduced into the caudal vena cava of rats (n=9). Rats were killed 2 (n=3), 4 (n=3) and 6(n=3) days after injection. Lung and liver extracts were prepared and assayed for luciferase activity. The luciferase activity is plotted as Integrated Light Units per milligram of protein extract using a logarithmic scale. Data are expressed as means±standard error of the mean (SEM).

FIG. 8—Competition between the galactoslyated DNA complex and asialoorosomucoid for binding to the ASGP receptor of HepG2 cells. HepG2 hepatoma cells were transfected with galactosylated poly-L-lysine conjugated to PEPCK-hFIX DNA. Prior to the addition of the DNA complex a 100-fold excess asialoorosomucoid was added to one set of plates (+Comp.). DNA internalization was monitored by slot-blot hybridization of the culture medium containing the DNA complex. Data are expressed as percentage of DNA internalized by the receptor at different times after transfection.

FIG. 9—Direct injection to the muscle and liver of naked DNA vs. condensed DNA. One hundred micrograms of naked DNA encoding SV40-luciferase were injected into the liver and abdominal muscle of two rats. The same amount of the pSV40-luciferase plasmid complexed to poly-L-lysine and condensed as described in Example 1 was injected as well into the liver and abdominal muscle of another two animals. Rats were sacrificed 48 hours post-injection. A piece of liver and abdominal muscle were homogenized in lysis buffer and cell lysates were analyzed for luciferase activity. All luciferase measurements were performed in triplicate, expressed as an average of the values and standardized for total protein. FIG. 9 shows the integrated luciferase units per mg of protein in the two different sets of animals.

FIG. 10—Direct injection into the brain tectum of naked DNA vs. condensed DNA. Intratectal injections of naked and poly-L-lysine condensed plasmid DNA can achieve high levels of expression in the cell body of the neuron over 20 days. β-galactosidase activity in retinas from rats whose brains were injected into the tectal areas and administered with either naked pCMV-lacZ, or condensed pCMV-lacZ (pCMV-lacZ+lys) at the concentrations shown. When the DNA is not condensed with poly-L-lysine the level of expression returns to background after 10 days post-injection.

FIG. 11—Changes in the absorbance of the DNA complexes during the condensation process. A plasmid containing the chimeric CMV-hLDL receptor gene was condensed with poly-L-lysine, using the procedure described in detail in Example 1. After the addition of poly-L-lysine the absorbance of the solution at 260 nm was determined. Concentrated NaCl was then added stepwise and the absorbance determined. The expected absorbance for the DNA contained in the complex is indicated by the dotted line. The initial NaCl concentration used in the condensation reaction was 500 mM.

FIG. 12—Relationship between the structure of the DNA complex and its function in adult rats. DNA-galatosylated poly-lysine complexes were prepared which correspond to various states of condensation/aggregation shown in FIG. 1B–1G. The DNA consisted of the SV40 promoter linked to the structural gene for *P. pyralis* luciferase gene. Rats were injected in the caudal vena cava with 300 μg of the various DNA complexes and the activity of luciferase was determined in extracts from the liver and the spleen 48 hr after injection. Each bar represents the mean±SEM for three rats; control rats were not injected with the DNA complex.

FIG. 13—Introduction of 3 mg of PEPCK-hLDLr in its relaxed (non complexed) vs. condensed form. In order to introduce the DNA complex into the animal, we perform a single injection of 3–10 ml of the DNA-complex solution (~400–900 mM NaCl) into the marginal ear vein of the rabbit. Approximately 1.5 ml of blood was drawn at the times indicated from the ear artery at 4 p.m. The determination of the concentration of serum cholesterol was performed in the Clinical Laboratory of University Hospitals of Cleveland from 300 μl of serum. The administration of a DNA complex solution containing 3 mg of the pPEPCK-hLDLR plasmid in a relaxed state to rabbit #676 did not result in a significant decrease (first arrow) in total serum cholesterol levels. A second injection of DNA complexes appropriately condensed containing 3 mg of the same DNA (second arrow) caused a 20% reduction of the levels of cholesterol in the blood. Four weeks after this second administration, cholesterol returned to approximately pre-treatment levels, reaching a peak at about 35 days.

FIG. 14—Injection of the poly-L-lysine/DNA complex containing 9 mg of the chimeric PEPCK-hLDLr gene. In our second experiment, 9 mg of the PEPCK-hLDLr gene appropriately condensed with galactosylated poly-L-lysine were administered to rabbit #737. As shown in FIG. 14, the treatment resulted in a 38% reduction of total serum cholesterol levels which lasted for about 5 weeks. Thus, a 3-fold increase in the dose of DNA complex resulted in a 2-fold reduction in total serum cholesterol levels.

FIG. 15—Injection of the poly-L-lysine/DNA complex containing 3 mg of the chimeric CMV-hLDLr gene. The administration of a DNA complex solution containing 3 mg of the chimeric CMV-hLDL receptor gene to rabbit #16 resulted in a maximal reduction of 30% in total serum cholesterol levels (FIG. 15). Eleven weeks after the injection, cholesterol levels are still 20% below those observed before the treatment.

FIG. 16A and 16B—Injection of multiple doses of the poly-L-lysine/DNA complex containing 3 mg of the chimeric CMV-hLDLr gene. Rabbits #775 (FIG. 16A) and #774 (FIG. 16B) were injected with 3 mg of the pCMV-hLDLR complex. In rabbit #775, this caused a maximal 24% reduction in cholesterol concentration in the blood, 3 weeks after treatment. Two additional injections did not result in a further significant reduction in serum cholesterol. In Rabbit #774, we observed a 36% decrease in the cholesterol levels in the blood (FIG. 16B) after the initial injection. Four reinjections once every 2 weeks were performed with the same amount of DNA complex. Two of them resulted in a minimal effect while the other two in a null reduction of total serum cholesterol levels. However, after five administrations of the DNA complex solution containing 3 mg of pCMV-hLDLr, the concentration of cholesterol had dropped about 48% with respect to pre-treatment levels.

Rabbit #774 was then treated with 10 mg of lovastatin (striped bar) per day for 10 weeks. A further 20% reduction in the levels of cholesterol has been observed. The inhibition of the endogenous pathway for cholesterol synthesis has thus brought the cholesterol concentration of rabbit #774 to 40% of that prior to the first gene transfer (FIG. 16B).

FIG. 17—Mock-injection of the poly-L-lysine/DNA complex containing 3 mg of the chimeric SV40-luciferase gene (irrelevant DNA). In order to control for a possible nonspecific reduction in total serum cholesterol levels by injecting rabbits with the galactosylated poly-L-lysine/DNA complexes in a solution with high NaCl concentration (~900 mM), we have administered a DNA complex solution containing an irrelevant DNA such as the luciferase gene into rabbit #775. FIG. 17 shows that the injection results in a non-significant ($\leq 12\%$) and transient ($\leq 5$ days) reduction in the serum cholesterol concentration. Thus, we have confirmed that the reduction in total serum cholesterol levels after the injection of appropriately condensed DNA particles encoding the human LDL receptor gene are not a result of either the high NaCl concentration of the solution or the presence of galactosylated poly-L-lysine/DNA particles.

FIG. 18—Relationship of turbidity to NaCl concentration. The figure shows the effect of initial and current NaCl concentration on the turbidity of a DNA/poly-lysine solution. Each line represents a different initial concentration.

FIG. 19—Effect of poly-L-lysine length on condensation concentration of NaCl.

FIG. 20A and 20E —CD spectra for different complexes. CD spectra were taken in a 0.1 cm path-length cuvette. The DNA was complexed with poly-L-lysine at identical molar ratios of amino to phosphate groups and various CD spectra compared: (A) standard control for DNA in 1M NaCl; (B) Ψ-DNA as observed at a concentration of NaCl at which multimolecular aggregation occurs; (C) aggregated DNA shows turbidity and decreased ellipticity; (D) condensed, unimolecular complexes of DNA; and (E) relaxed DNA complex spectrum. The spectra was taken at equal concentrations of polymer and the signal for the buffer was subtracted in each case. Details of the assay are presented in the Methods.

FIGS. 21A–D provide NMR spectra obtained from unmodified polylysine, LC sulfo SPDP-conjugated polylysine, LC sulfo SPDP-conjugated polylysine following treatment with DTT and LC sulfo SPDP-conjugated polylysine complexed with the C1315 peptide, respectively.

FIG. 22 provides a graph depicting the specific binding (expressed as cpm/one million cells) plotted against the concentration of iodinated C105Y peptide (nM). Traces are shown for the specific binding of $^{125}$I-C105Y to HuH7 cells (o), HepG2 (high) cells (□) and HepG2 (low) cells (◊).

FIG. 23A provides a graph depicting the dose dependence and time course of transfection of various cell lines with the C1315 peptide-based complex.

FIG. 23B provides a graph depicting a competition experiment in which a 10-fold molar excess of free C1315 peptide (i.e., not present in a complex with an expression vector) was present during transfection experiments using the C1315 peptide-based complex.

FIG. 24 depicts the level of expression of Factor IX by various transfected cell lines.

DETAILED DESCRIPTION OF THE PREFERRED EMBODIMENTS

The Multicellular Organism

Figure 1A:
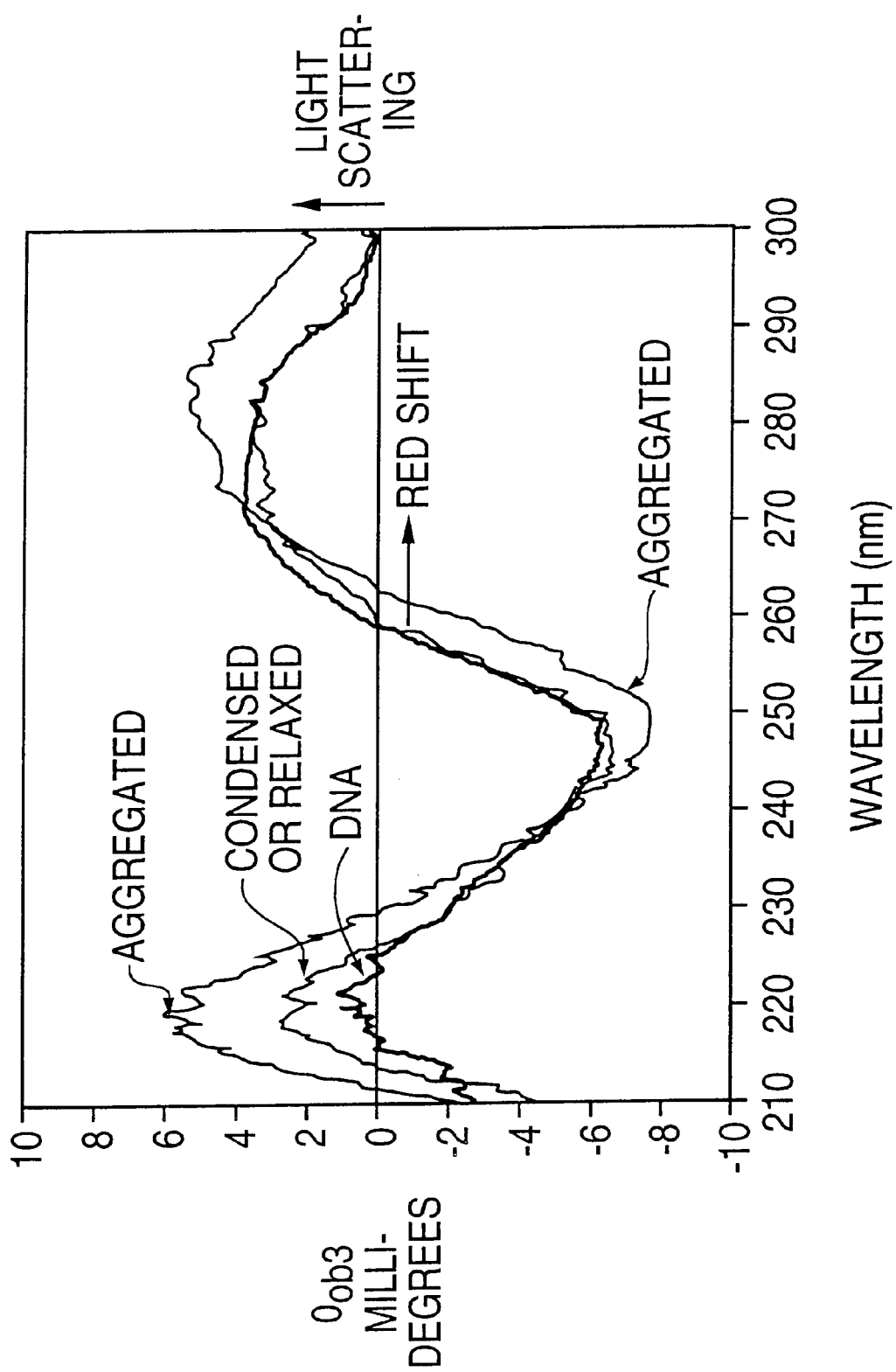
Figure 1G:
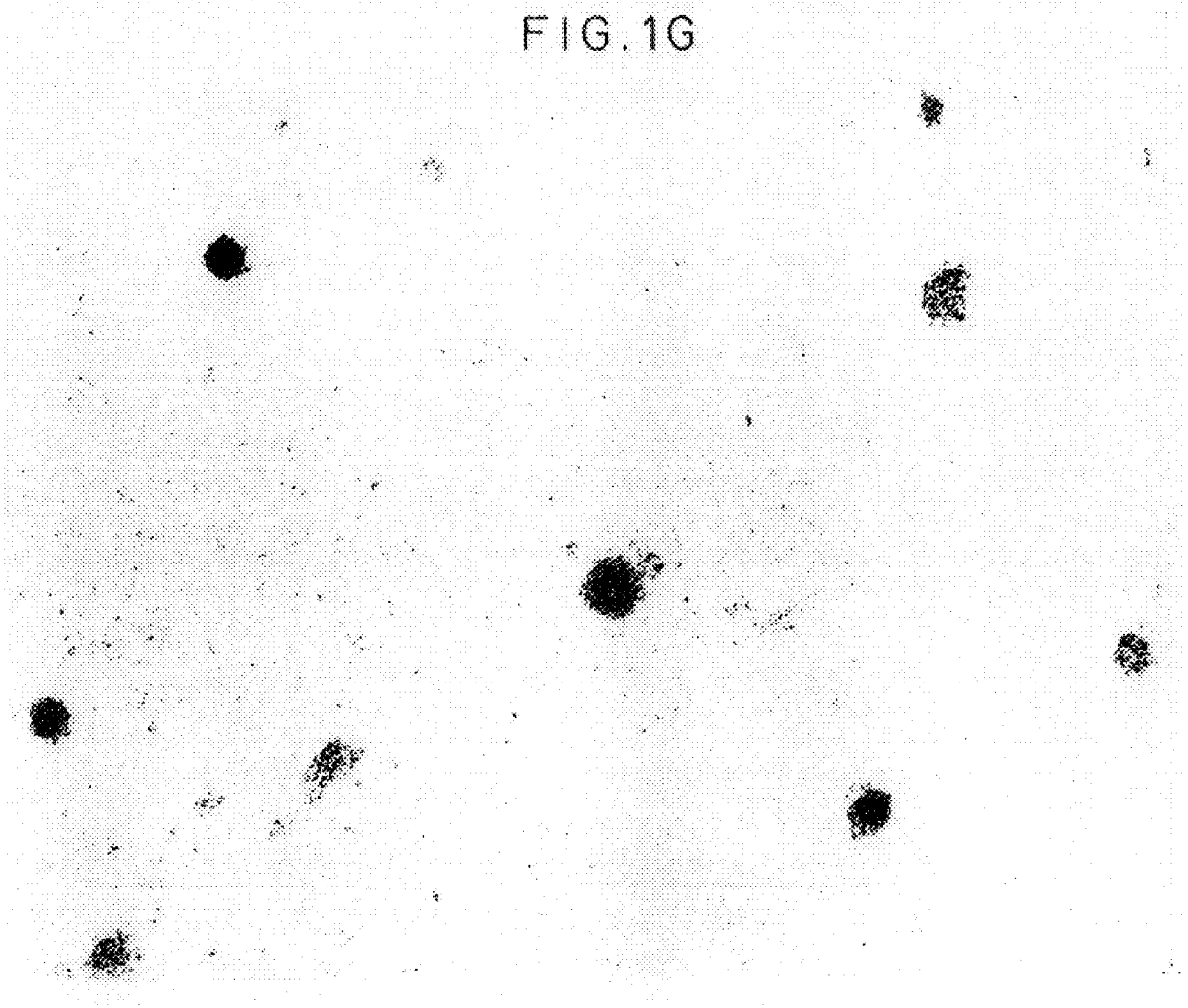
Figure 1I:
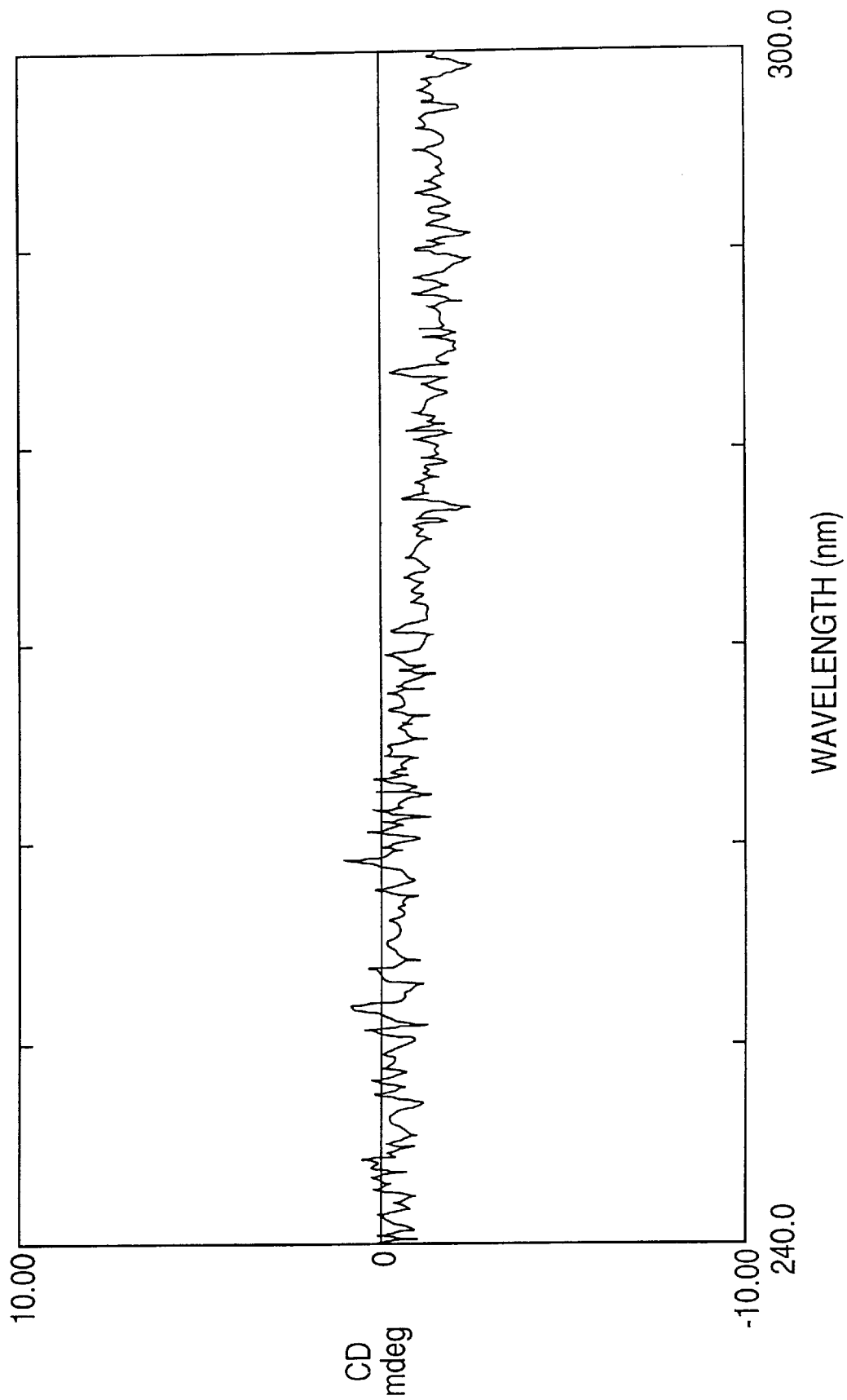
Figure 1J:
Figure 2A:
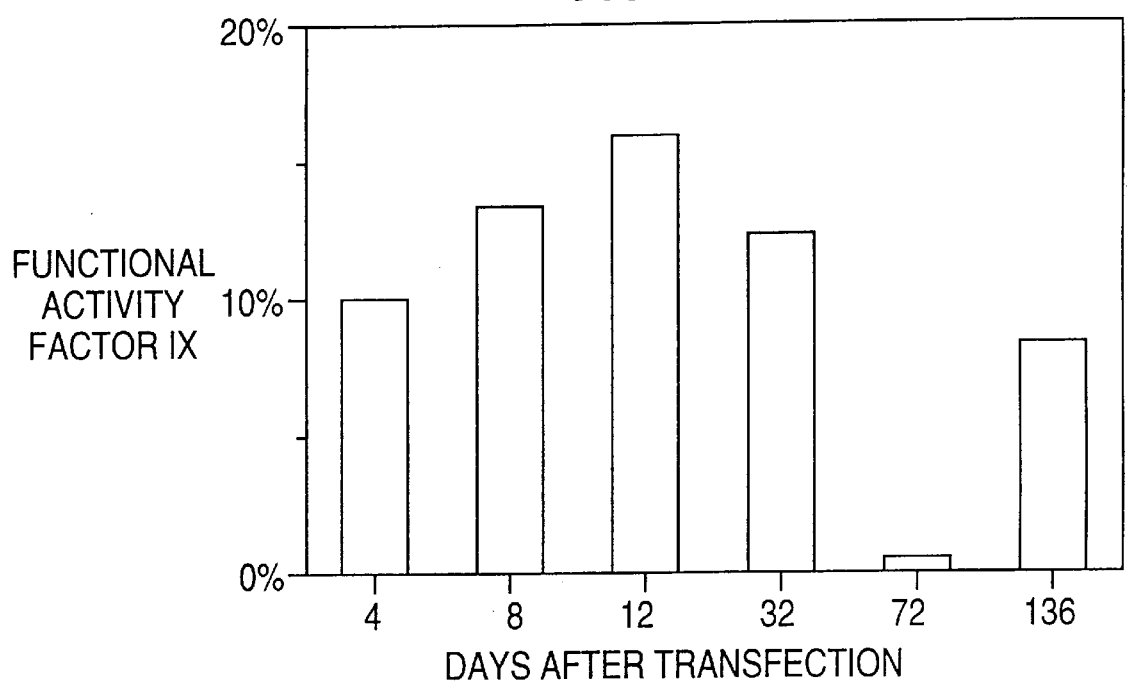
Figure 2B:
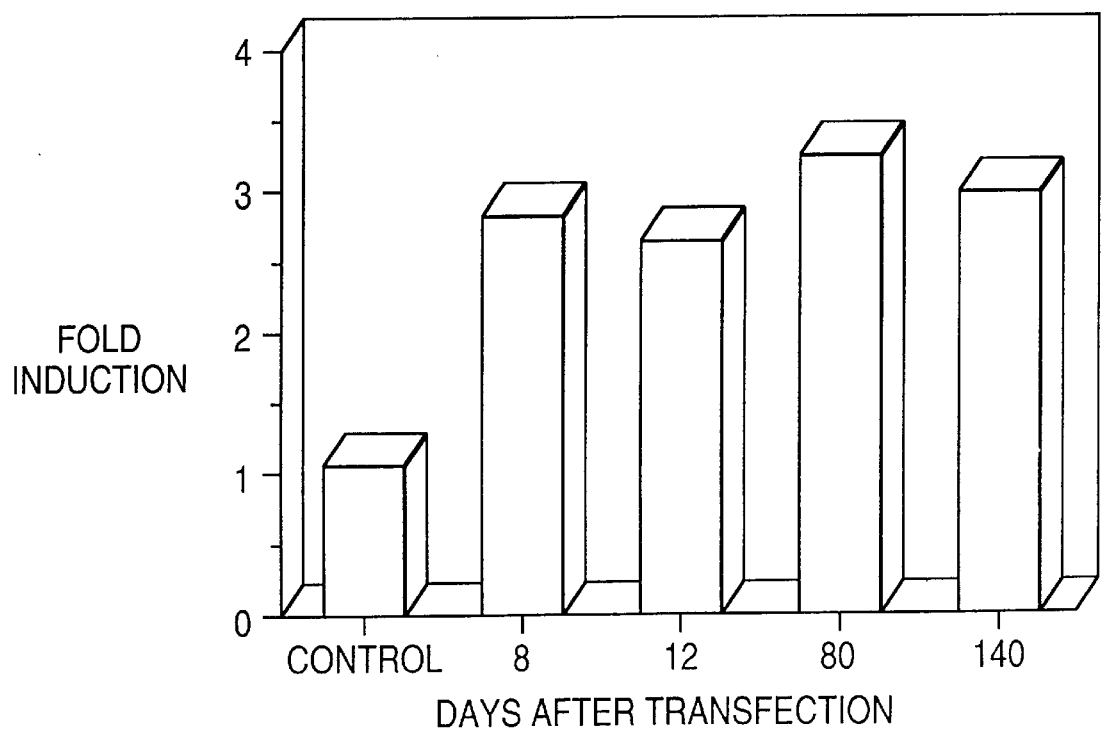

Any multicellular organism into which it may be desirable to introduce exogenous nucleic acid is a potential subject for the present invention. The multicellular organism may be a plant or an animal, preferably the latter. The animal is preferably a vertebrate animal, and more preferably a higher vertebrate, i.e., a mammal or bird, the former being especially preferred. Among mammals, preferred subjects are human and other primates, laboratory animals such as mice, rats, rabbits and hamsters, pet animals such as dogs and cats, and farm animals such as horses, cows, goats, pigs and sheep. It will be noted that these animals come from four orders of class Mammalia: Primata, Rodenta, Carnivora and Artiodactyla.

The Target Cell

The target cells may belong to tissues (including organs) of the organism, including cells belonging to (in the case of an animal) its nervous system (e.g., the brain, spinal cord and peripheral nervous cells), the circulatory system (e.g., the heart, vascular tissue and red and white blood cells), the digestive system (e.g., the stomach and intestines), the respiratory system (e.g., the nose and the lungs), the reproductive system, the endocrine system (the liver, spleen, thyroids, parathyroids), the skin, the muscles, or the connective tissue.

Alternatively, the cells may be cancer cells derived from any organ or tissue of the target organism, or cells of a parasite or pathogen infecting the organism, or virally infected cells of the organism.

A useful procedure for hepatic gene therapy requires an efficient and relatively non-invasive approach to the introduction of genes of interest into the liver. Several techniques, employing receptor mediated gene transfer, have been used with some success. However, there is a need for a readily reproducible procedure which results in the prolonged expression of the transgene in the liver, even in the absence of partial hepatectomy, and which therefore could be used for human gene therapy. Exogenous DNA has been introduced into hepatocytes of adult animals by targeting the asialoglycoprotein (ASGP) receptor by means of a ligand-poly-L-lysine biconjugate. For the ligand-targeting technique to be efficient, the DNA must be in a form which permits it to remain intact in the blood and is small enough to be recognized by the ASGP receptor on the surface of the hepatocytes. Wagner, et al. have targeted genes to the transferrin receptor in hepatoma cells by condensing the DNA with a poly-L-lysine/transferrin conjugate, into a complex with a diameter of 80–100 nm. This size DNA conjugate is appropriate for recognition by the transferrin receptor in hepatoma cells, but the ASGP receptor of hepatocytes discriminates against ligands larger than 10–20 nm in diameter.

The present inventors have developed a procedure for the introduction of genes into the liver of adult animals by receptor mediated uptake which resulted in the expression of the gene for 140 days (the duration of the experiment). This procedure has potential for application to human gene therapy. The major advantages of this method are: (i) the ease of preparation of the DNA complex; (ii) the ability to target genes to specific tissues; (iii) the prolonged expression of the gene in the liver; (iv) the relative safety of the complex, since it is devoid of infectious viral DNA; and (v) the episomal maintenance of the introduced gene.

TARGETING

A. Generally

"Targeting" is the administration of the compacted nucleic acid in such a manner that it enters the target cells in amounts effective to achieve the clinical purpose. In this regard, it should be noted that DNA and RNA are capable of replication in the nucleus of the target cell, and in consequence the ultimate level of the nucleic acid in the cell may increase after uptake. Moreover, if the clinical effect is mediated by a protein expressed by the nucleic acid, it should be noted that the nucleic acid acts as a template, and thus high levels of protein expression can be achieved even if the number of copies of the nucleic acid in the cell is low. Nonetheless, it is desirable to compact high concentrations of DNA to increase the number of target cells which take up the DNA and the number of DNA molecules taken up by each cell.

The route and site of administration may be chosen to enhance targeting. For example, to target muscle cells, intramuscular injection into the muscles of interest would be a logical choice. Lung cells might be targeted by administering the compacted DNA in aerosol form. The vascular endothelial cells could be targeted by coating a balloon catheter with the compacted DNA and mechanically introducing the DNA.

In some instances, the nucleic acid binding moiety, which maintains the nucleic acid in the compacted state, may also serve as a targeting agent. Polymers of positively charged amino acids are known to act as nuclear localization signals (NLS) in many nuclear proteins. A pSV40-luciferase DNA condensed with poly-L-lysine, was injected in situ into the abdominal muscle of rats. Despite the absence of an explicit target cell binding moiety, we observed a 20-fold higher luciferase activity in rats injected with the complexed DNA than in the rat injected with naked DNA. Nonetheless, in some embodiments, targeting may be improved if a target cell binding moiety is employed.

B. Use Of A Target Binding Moiety (TBM)

If a TBM is used, it must bind specifically to an accessible structure (the "receptor") of the intended target cells. It is not necessary that it be absolutely specific for those cells, however, it must be sufficiently specific for the conjugate to be therapeutically effective. Preferably, its cross-reactivity with other cells is less than 10%, more preferably less than 5%.

There is no absolute minimum affinity which the TBM must have for an accessible structure of the target cell; however, the higher the affinity, the better. Preferably, the affinity is at least $10^3$ liters/mole, more preferably, at least $10^6$ liters/mole.

The TBM may be an antibody (or a specifically binding fragment of an antibody, such as an Fab, Fab, $V_M$, $V_L$ or CDR) which binds specifically to an epitope on the surface of the target cell. Methods for raising antibodies against cells, cell membranes, or isolated cell surface antigens are known in the art. Furthermore, the TBM may comprise a single-chain Fv which binds specifically to an epitope on the surface of the target cell. The single-chain Fv may comprise a fusion protein with a NABM or a therapeutic protein sequence (e.g, an enzyme, cytokine, protein antibiotic, etc.).

The TBM may be a lectin, for which there is a cognate carbohydrate structure on the cell surface.

The target binding moiety may be a ligand which is specifically bound by a receptor carried by the target cells.

One class of ligands of interest are carbohydrates, especially mono- and oligosaccharides. Suitable ligands include galactose, lactose and mannose.

Another class of ligands of interest are peptides (which here includes proteins), such as insulin, epidermal growth factor(s), tumor necrosis factor, prolactin, chorionic gonadotropin, FSH, LH, glucagon, lactoferrin, transferrin, apolipoprotein E, gp120 and albumin.

The following table lists preferred target binding moieties for various classes of target cells:

| Target Cells | Target Binding Moiety |
| --- | --- |
| liver cells | galactose |
| Kupffer cells | mannose |
| macrophages | mannose |
| lung, liver, intestine | Fab fragment vs. polymeric immunoglobulin receptor (pIg R) |
| adipose tissue, | insulin |
| lymphocytes | Fab fragment vs CD4 or gp120 |
| enterocyte | Vitamin B12 |
| muscle | insulin |
| fibroblasts | mannose-6-phosphate |
| nerve cells | Apolipoprotein E |

The target binding moiety may be encompassed with a larger peptide or protein. The present invention provides peptides containing the pentapeptide binding domain for the serpin enzyme complex (SEC) receptor. The present invention further contemplates the production of retroviral particles comprising modified (i.e., chimeric) envelope proteins containing protein sequences comprising a target binding moiety capable of binding to a SEC receptor (or any other desired receptor). Retrovirus particles bearing these modified envelope proteins may be used to deliver genes of interest to cells expressing the SEC receptor. Retroviral particles bearing chimeric proteins containing peptide ligands and a portion of the envelope (env) protein of retroviruses (e.g., ecotropic Moloney murine leukemia virus or avian retroviruses) have been shown to be capable of binding to cells expressing the cognate receptor [Kasahara et al. (1994) *Science* 266:1373 and Valsesia-Wittmann et al. (1994) *J. Virol.* 68:4609]

The use of a target binding moiety is not strictly necessary in the case of direct injection of the NABM/NA condensed complex. The target cell in this case is passively accessible to the NABM/NA condensed complex by the injection of the complex to the vicinity of the target cell.

C. Liposome-Mediated Gene Transfer

The possibility of detecting gene expression by encapsulating DNA into a liposome (body contained by a lipid bilayer) using various lipid and solvent conditions, and injecting the liposome into animal tissues, has been demonstrated. However, despite the potential of this technique for a variety of biological systems, the DNA used in these experiments has not been modified or compacted to improve its survival in the cell, its uptake into the nucleus or its rate of transcription in the nucleus of the target cells. Thus, these procedures have usually resulted in only transient expression of the gene carried by the liposome.

Cationic lipids have been successfully used to transfer DNA. The cationic component of such lipids can compact DNA in solution. This method has been shown to result in heavily aggregated DNA complexes that, when used for transfecting the DNA in vitro, results in increased efficiency of gene transfer and expression (relative to naked DNA). Although the formation of these complexes can promote gene transfer in vitro, the injection of such complexes in vivo does not result in long lasting and efficient gene transfer.

The condensation procedure of the present invention provide structural features to the DNA/cationic lipid complex that will make it more amenable to prolonged in vivo expression. The combination of such methods could be accomplished by either of two procedures:

1. Formation of condensed DNA complex that is later encapsulated using neutral lipids into liposome bodies, or
2. Using the procedure described in this patent, the formation of highly condensed unimolecular DNA complexes upon condensation with cationic lipids could be accomplished. These complexes should provide a higher efficiency of gene transfer into tissues of animals in vivo.

The procedure of the present invention for the condensation of DNA, if coupled to the encapsulation of the resulting compacted DNA into a liposome body, could provide a variety of advantages for transfection into animals:

1. The liposome promotes the passive fusion with the lipid bilayer of the cytoplasmic membrane of mammalian cells in tissues.
2. The condensed DNA could then transfer the genetic information with a higher efficiency through the cell compartments to the nucleus for its expression.
3. Condensed DNA could be protected against degradation inside the cell, thus augmenting the duration of the expression of the newly introduced gene.
4. Possible immunological response to the polycation condensed DNA could be avoided by the encapsulation with the immunologically inert lipid bilayer.

The Nucleic Acid Binding Moiety

Any substance which binds reversibly to a nucleic acid may serve as the nucleic acid binding moiety (NABM), provided that (1) it binds sufficiently strongly and specifically to the nucleic acid to retain it until the conjugate reaches and enters the target cell, and does not, through its binding, substantially damage or alter the nucleic acid and (2) it reduces the interactions between the nucleic acid and the solvent, and thereby permits condensation to occur. The ultimate criterion is one of therapeutic effectiveness of the conjugate.

Preferably, the NABM is a polycation. Its positively charged groups bind ionically to the negatively charged DNA, and the resulting charge neutralization reduces DNA-solvent interactions. A preferred polycation is polylysine. Other potential nucleic acid binding moieties include Arg-Lys mixed polymers, polyarginine, polyornithine, histones, avidin, and protamines.

The Nucleic Acid

Basic procedures for constructing recombinant DNA and RNA molecules in accordance with the present invention are disclosed by Sambrook, J. et al., In: *Molecular Cloning: A Laboratory Manual*, Second Edition, Cold Spring Harbor Press, Cold Spring Harbor, N.Y. (1989), which reference is herein incorporated by reference.

The nucleic acid may be a DNA, RNA, or a DNA or RNA derivative such as a derivative resistant to degradation in vivo, as discussed below. Within this specification, references to DNA apply, mutatis mutandis, to other nucleic acids as well, unless clearly forbidden by the context. The nucleic acid may be single or double stranded. It is preferably of 10 to 1,000,000 bases (or base pairs), more preferably 100 to 100,000, and the bases may be same or different. The bases may be the "normal" bases adenine (A), guanine (G), thymidine (T), cytosine (C) and uracil (U), or abnormal bases such as those listed in 37 CFR § 1.822 (p) (1). The nucleic acid may be prepared by any desired procedure.

In a preferred embodiment, the nucleic acid comprises an expressible gene which is functional in the target cell. For example, the gene may encode coagulation factors, (such as Factor IX), enzymes involved in specific metabolic defects, (such as urea cycle enzymes, especially ornithine transcarbamylase, argininosuccinate synthase, and carbamyl phosphate synthase); receptors, (e.g., LDL receptor); toxins; thymidine kinase to ablate specific cells or tissues; ion channels (e.g., chloride channel of cystic fibrosis); membrane transporters (e.g., glucose transporter); and cytoskeletal proteins, (e.g., dystrophin). The gene may be of synthetic, cDNA or genomic origin, or a combination thereof. The gene may be one which occurs in nature, a non-naturally occurring gene which nonetheless encodes a naturally occurring polypeptide, or a gene which encodes a recognizable mutant of such a polypeptide. It may also encode an mRNA which will be "antisense" to a DNA found or an mRNA normally transcribed in the host cell, but which antisense RNA is not itself translatable into a functional protein.

For the gene to be expressible, the coding sequence must be operably linked to a promoter sequence functional in the target cell. Two DNA sequences (such as a promoter region sequence and a coding sequence) are said to be operably linked if the nature of the linkage between the two DNA sequences does not (1) result in the introduction of a frame-shift mutation in the region sequence to direct the transcription of the desired gene sequence, or (3) interfere with the ability of the gene sequence to be transcribed by the promoter region sequence. A promoter region would be operably linked to a DNA sequence if the promoter were capable of effecting transcription of that DNA sequence. In order to be "operably linked" it is not necessary that two sequences be immediately adjacent to one another. A nucleic acid molecule, such as DNA, is said to be "capable of expressing" a mRNA if it contains nucleotide sequences which contain transcriptional regulatory information and such sequences are "operably linked" to nucleotide sequences which encode the RNA. The precise nature of the regulatory regions needed for gene expression may vary from organism to organism, but in general include a promoter which directs the initiation of RNA transcription. Such regions may include those 5'-non-coding sequences involved with initiation of transcription such as the TATA box.

If desired, the non-coding region 3' to the gene sequence coding for the desired RNA product may be obtained. This region may be retained for its transcriptional termination regulatory sequences, such as those which provide for termination and polyadenylation. Thus, by retaining the 3'-region naturally contiguous to the coding sequence, the transcriptional termination signals may be provided. Where the transcriptional termination signals are not satisfactorily functional in the expression host cell, then a 3' region functional in the host cell may be substituted.

The promoter may be an "ubiquitous" promoter active in essentially all cells of the host organism, e.g., for mammals, the beta-actin promoter, or it may be a promoter whose expression is more or less specific to the target cells. Generally speaking, the latter is preferred. A promoter native to a gene which is naturally expressed in the target cell may be used for this purpose, e.g., the PEPCK (phosphoenol pyruvate carboxykinase) promoter for expression in mammalian liver cells. Other suitable promoters include albumin, metallothionein, surfactant, apoe, pyruvate kinase, LDL receptor HMG CoA reductase or any promoter which has been isolated, cloned and shown to have an appropriate pattern of tissue specific expression and regulation by factors (hormones, diet, heavy metals, etc.) required to control the transcription of the gene in the target tissue. In addition, a broad variety of viral promoters can be used; these include MMTV, SV-40 and CMV. An "expression vector" is a vector which (due to the presence of appropriate transcriptional and/or translational control sequences) is capable of expressing a DNA (or cDNA) molecule which has been cloned into the vector and of thereby producing an RNA or protein product. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, when a eukaryotic expression vector is employed, then the appropriate host cell would be any eukaryotic cell capable of expressing the cloned sequences.

In addition to or instead of an expressible gene, the nucleic acid may comprise sequences homologous to genetic material of the target cell, whereby it may insert itself ("integrate") into the genome by homologous recombination, thereby displacing a coding or control sequence of a gene, or deleting a gene altogether.

In another embodiment, the nucleic acid molecule is "antisense" to a genomic or other DNA sequence of the target organism (including viruses and other pathogens) or to a messenger RNA transcribed in cells of the organisms, which hybridizes sufficiently thereto to inhibit the transcription of the target genomic DNA or the translation of the target messenger RNA. The efficiency of such hybridization is a function of the length and structure of the hybridizing sequences. The longer the sequence and the closer the complementarily to perfection, the stronger the interaction. As the number of base pair mismatches increases, the hybridization efficiency will fall off. Furthermore, the GC content of the packaging sequence DNA or the antisense RNA will also affect the hybridization efficiency due to the additional hydrogen bond present in a GC base pair compared to an AT (or AU) base pair. Thus, a target sequence richer in GC content is preferable as a target.

It is desirable to avoid antisense sequences which would form secondary structure due to intramolecular hybridization, since this would render the antisense nucleic acid less active or inactive for its intended purpose. One of ordinary skill in the art will readily appreciate whether a sequence has a tendency to form a secondary structure. Secondary structures may be avoided by selecting a different target sequence.

An oligonucleotide, between about 15 and about 100 bases in length and complementary to the target sequence may be synthesized from natural mononucleosides or, alternatively, from mononucleosides having substitutions at the non-bridging phosphorous bound oxygens. A preferred analogue is a methylphosphonate analogue of the naturally occurring mononucleosides. More generally, the mononucleoside analogue is any analogue whose use results in oligonucleotides which have the advantages of (a) an improved ability to diffuse through cell membranes and/or (b) resistance to nuclease digestion within the body of a subject (Miller, P. S. et al., *Biochemistry* 20:1874–1880 (1981)). Such nucleoside analogues are well-known in the art. The nucleic acid molecule may be an analogue of DNA or RNA. The present invention is not limited to use of any particular DNA or RNA analogue, provided it is capable of fulfilling its therapeutic purpose, has adequate resistance to nucleases, and adequate bioavailability and cell take-up. DNA or RNA may be made more resistant to in vivo degradation by enzymes, e.g., nucleases, by modifying internucleoside linkages (e.g., methylphosphonates or phosphorothioates) or by incorporating modified nucleosides (e.g., 2'-0-methylribose or 1'-alpha- anomers). The entire nucleic acid molecule may be formed of such modified linkages, or only certain portions, such as the 5' and 3' ends, may be so affected, thereby providing resistance to exonucleases.

Nucleic acid molecules suitable for use in the present invention thus include but are not limited to dideoxyribonucleoside methylphosphonates, see Mill, et al., Biochemistry, 18:5134–43 (1979), oligodeoxynucleotide phosphorothioates, see Matsukura, et al., *Proc. Nat. Acad. Sci.*, 84:7706–10 (1987), oligodeoxynucleotides covalently linked to an intercalating agent, see Zerial, et aL, Nucleic Acids Res., 15:9909–19 (1987), oligodeoxynucleotide conjugated with poly(L-lysine), see Leonetti, et al., *Gene*, 72:32–33 (1988), and carbamate- linked oligomers assembled from ribose-derived subunits, see Summerton, J., Antisense Nucleic Acids Conference, 37:44 (New York 1989).

Compaction Of The Nucleic Acid

It is desirable that the complex of the nucleic acid and the nucleic acid binding moiety be compacted to a particle size which is sufficiently small to achieve uptake by receptor mediated endocytosis, passive internalization, receptor-mediated membrane permeabilization, or other applicable mechanisms. Desirably, the complex of the compacted nucleic acid, the target binding moiety, and the nucleic acid binding moiety is small, e.g., less than 100 nm, because the sinusoidal capillary systems of the lung and spleen will trap aggregates of that size, and more preferably less than 80 or 90 nm, as that is the typical internal diameter of coated-pit endocytic vesicles. Since complexes larger than 30 nm may be susceptible to nonspecific takeup by macrophages in the spleen and liver, the conjugate is preferably also smaller than 30 nrn.

In the case of the ASGP receptor of the liver, complexes larger than 15–23 nm are excluded from uptake. This size limitation in vivo for the receptor is probably directly related to the existence of another receptor for galactosylated proteins in the Kupffer cells of the liver. The Kupffer cell receptor is very efficient in taking up and degrading galactosylated molecules of larger size in vivo and thus, would compete for the uptake of the galactosylated DNA complex with the ASGP receptor on the surface of hepatocytes. Most preferably, for liver delivery, the complex is less than 23 nm, more preferably less than 15 nm, still more preferably no more than 12 nm in diameter.

Figure 12:
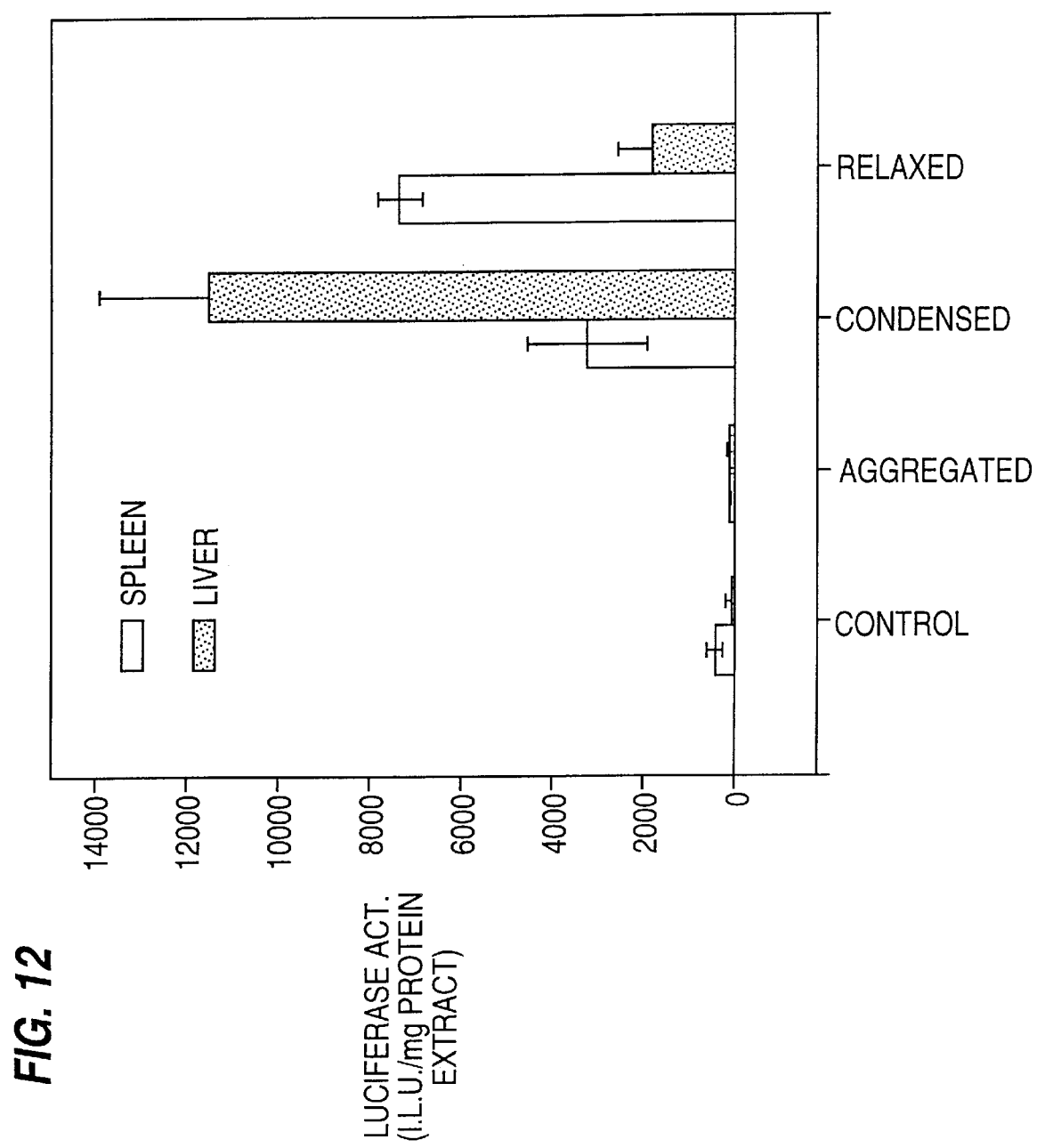

The present invention calls for the complex of the nucleic acid and the nucleic acid-binding carrier to be compacted without causing aggregation or precipitation, and preferably to a condensed state (see FIG. 12). For the purpose of the present invention, it is helpful to characterize DNA as having one of the following states: normal (uncondensed); condensed; relaxed; uni-aggregated (clusters of unimolecular toroids); multi-aggregated (clusters of multimolecular toroids); and precipitated. These states are defined in terms of their appearance under electron microscopy (see Table 103).

Condensed DNA is in a state in which interaction with the solvent is minimal and therefore the DNA is in the form of isolated spheres or toroids. It is not fibrous to an appreciable degree. Relaxed DNA, typically formed by dissociation of polycation from the DNA, forms fibers. Aggregated DNA forms clumped or multimolecular toroids.

The theoretical size of a unimolecular DNA complex can be calculated by the formulae set forth in legends "b" and "c" of Table 106. Preferably, the complexes of this invention have a diameter which is less than double the size calculated by one or both of these formulae. Larger complexes are likely to correspond to multimoleculary aggregated DNA.

DNA can be compacted to a condensed state by neutralizing its charge, e.g., by addition of a polycation, or otherwise reducing its interactions with solvent. However, the polycation can cause aggregation or precipitation of the DNA if a chaotropic agent is not employed to prevent it. Compaction therefore can be accomplished by judicious use of both the polycation (to condense the DNA) and (as needed) of a chaotropic agent (to prevent aggregation or precipitation).

Overuse of the chaotropic agent can, however, result in relaxation of the DNA. Preferably, the complex has a unaggregated, unimolecular toroid structure condensed to smaller than 23 nm in diameter; the degree of compaction may be determined by electron microscopy. For example, a complex of the PEPCK-hFIX gene with galactosylated polylysine has been compacted to a unimolecular toroid with a mean diameter of about 12 nm, as shown in Table 106.

The term "unimolecular toroid" indicates that the toroid contains only one nucleic acid molecule; the toroid may contain many carrier (e.g., galactosylated poly-Lys) molecules. A typical ratio is one DNA molecule to about 100 carrier molecules, per "unimolecular" toroid. Alternatively, and perhaps more precisely, this structure may be referred to as a mono-nucleic acid toroid. Unimolecular and multimolecular toroids (the latter each contain more than one DNA molecule) may be distinguished by the different size of each of the complexes when viewed by the electron microscope, indicating the multi- or unimolecular (counting only the DNA molecules) composition of the toroids.

We have also used other techniques to identify structural changes in the DNA upon poly-L-lysine binding. The first of these is the spectrophotometric determination of the turbidity in the solution using the absorbance at 400 nm. Turbidity is primarily an indicator of aggregation. Aggregation is confirmed by a circular dichroism (CD) value greater than 0 at wavelengths from 300 to 340 nm.

Figure 18:
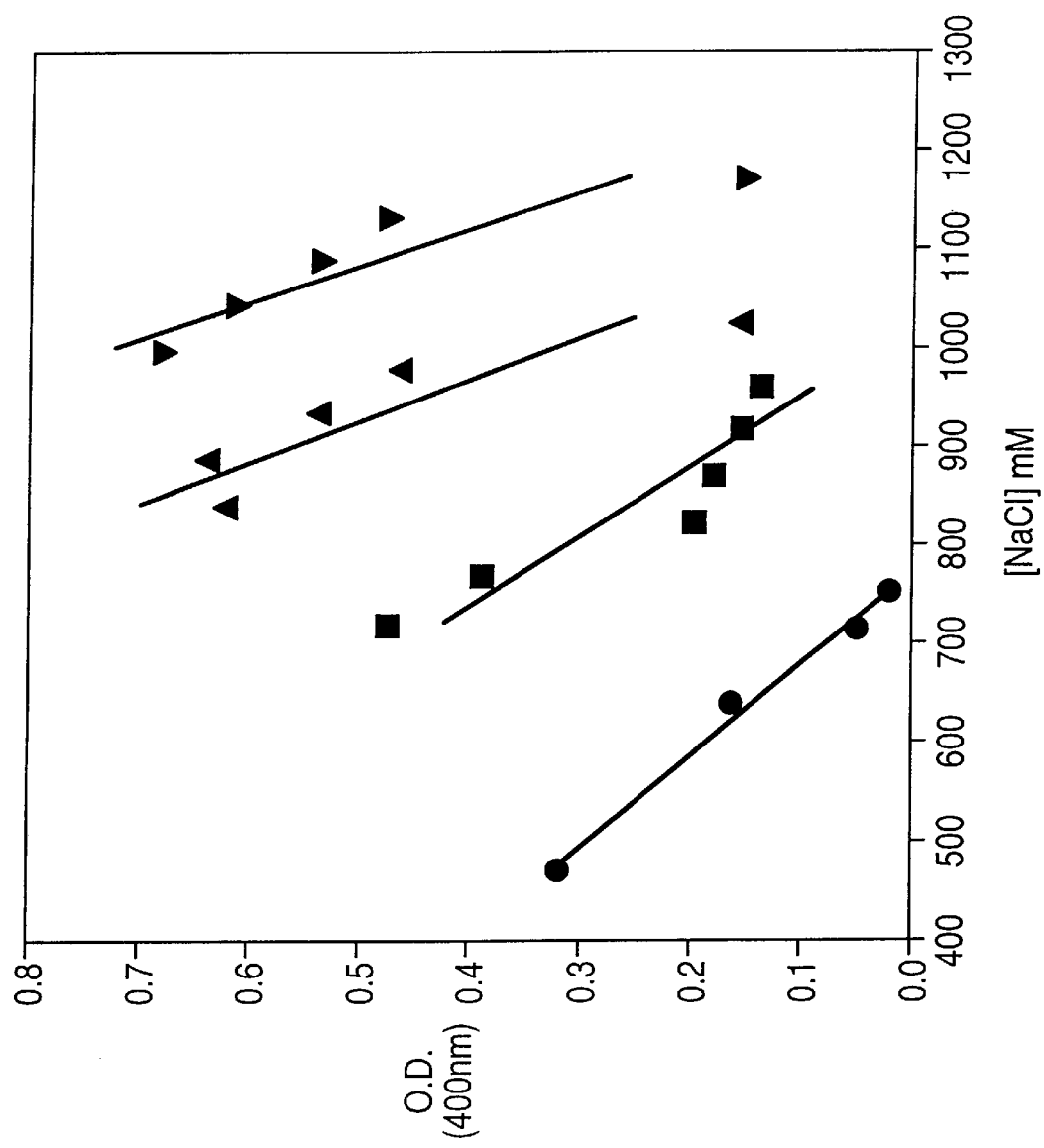

FIG. 18 illustrates the effect on turbidity of adding the poly-L-lysine to the DNA solution at different starting concentrations of NaCl. Turbidity increases as the initial concentration of salt is increased (this could be easily confirmed by eye), indicating that the condensation of the DNA complex at lower ionic strength results in a suspension of particles composed of unimolecular DNA-poly-L-lysine complexes interacting with each other. We noted that the solutions of DNA condensed at lower salt concentration were clear, with the presence of particulate matter in suspension. Solutions containing the DNA complex with different degrees of turbidity were analyzed by EM to visualize the DNA structures formed in each situation. Appropriately condensed, unimolecular DNA complexes were found with both clear and slightly turbid solutions. This was not true for the condensation of DNA complexes at initial low ionic strength where we noted minimal absorbance at 400 nm (FIG. 18) because the solutions containing particles in suspension did not absorb at 400 nm. However, when these solutions were analyzed using EM, we noted the expected transitional structures shown in FIG. 1. When the particles in suspension became totally dispersed, the structures identified by EM were essentially identical to condensed unimolecular DNA complexes. Thus, turbidity of the solution containing the DNA complexes is dependent on the initial concentration of salt used for condensation of the complex. Although the mechanisms responsible for the observed differences in the condensation of DNA at initial low and high ionic strength is not clear, we adapted our protocol to appropriately condense DNA, avoiding the formation of turbid solutions.

Figure 11:
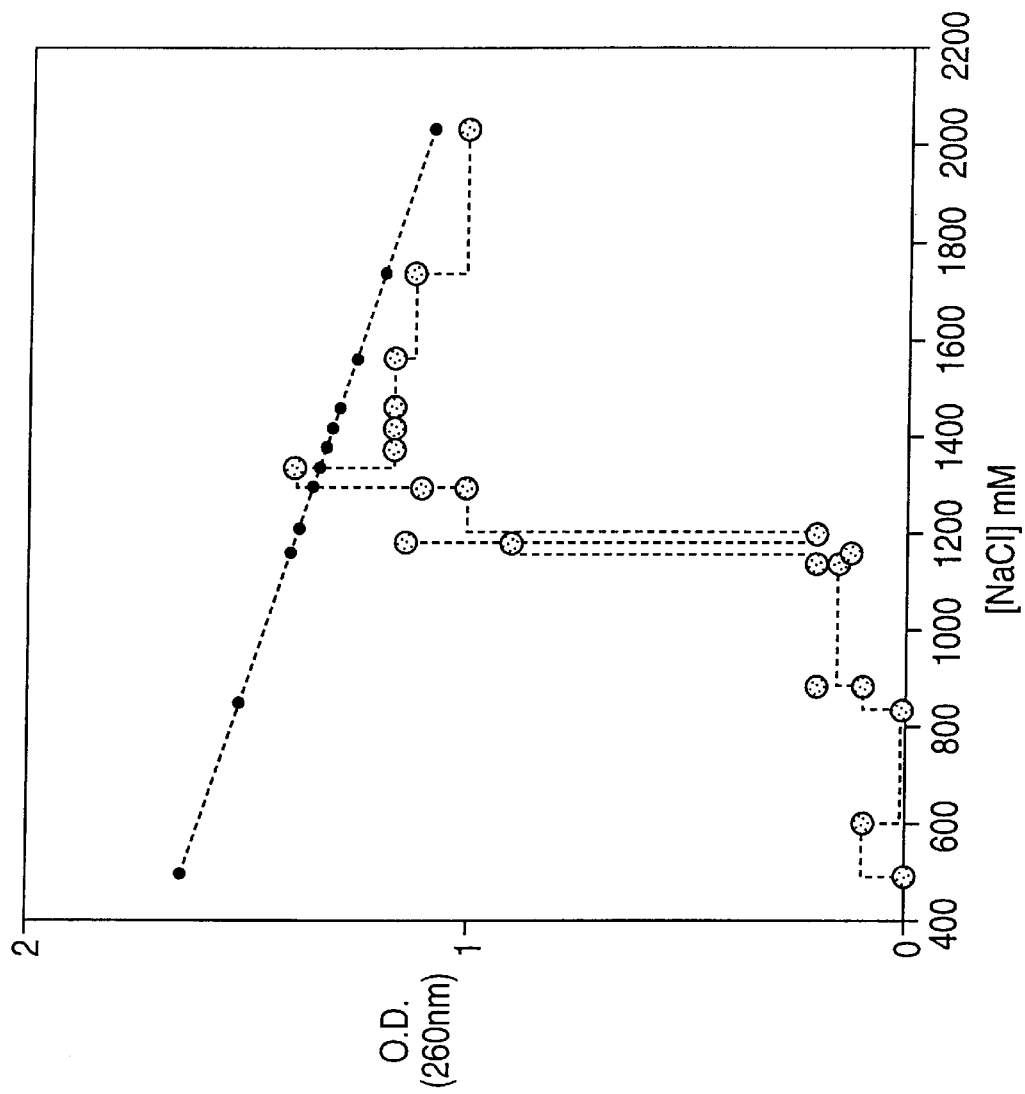

A more reliable technique for diagnosing the structural transition of DNA-poly-L-lysine complexes in solution is the absorbance of the condensing complex at 260 nm as the concentration of NaCl increases. The uni-aggregated DNA complex in suspension has only 10–30% of the expected absorbance because the particulate matter does not absorb at 260 nm. The addition of NaCl disperses the uni-aggregated DNA complex in suspension which results in the observed steep increase in the absorbance noted in FIG. 11. At this point the solution is clear and there are no visible particulate structures in suspension. This feature of the DNA-poly-L-lysine condensation clearly correlates with the structures shown in FIG. 1. At a concentration of NaCl which causes a steep increase in the absorbance at 260 nm, we observed unaggregated, condensed complexes by EM; before this critical concentration of NaCl was attained, the DNA complex appear aggregated and at higher NaCl concentrations the DNA complex was relaxed. A second transition in absorbance at 260 nm, as a result of the relaxation of the condensed DNA complex that was in suspension, indicates the full solubilization of the DNA complex.

Circular dichroism (CD) can be used to monitor the condensation of DNA. When the spectrum is identical to that of DNA alone, then the DNA complex is assumed to be correctly compacted, i.e., into unimolecular complexes. In another words, the positive spectrum at 220 nm is quantitatively similar to the 220 nm spectrum of DNA alone, and the cross-over (the wavelength at which the spectrum of the complex crosses the 0 point) is essentially identical to that of DNA alone. When the DNA aggregates into multimolecular complexes, the positive spectrum at 270 nm is inverted into a negative spectrum at that wavelength (this is called psi-DNA structure or $\psi$-DNA).

Table 103 sets forth the characteristics of each state as determined by naked eye observation, circular dichroism spectroscopy, electron microscopy, and absorbance at 260 nm.

It should be noted that any other techniques which are capable of identifying condensed DNA complexes may be used instead of or in combination with those discussed above.

To compact the nucleic acid, the carrier is added to the nucleic acid solution, whereby the carrier disrupts the nucleic acid: solvent interactions allowing the nucleic acid to condense. Preferably, at least the turbidity of the solution is monitored as the carrier is added, so that a change in state is promptly detected. Once turbidity appears, the state of the DNA may be further analyzed by CD spectroscopy to determine whether the DNA is in the condensed or the aggregated state. (Precipitation should also be detectable with the naked eye.) Preferably, the carrier is added sufficiently slowly to the nucleic acid solution so that precipitation and aggregation are minimized. If precipitation or aggregation occur, a chaotropic salt should be added slowly, and the result again examined by CD spectroscopy. The preferred salt is NaCl. Other chaotropic salts can be used as long as they are tolerated by the animal (or cells) to which they will be administered. Suitable agents include Sodium sulfate ($Na_2SO_4$), Lithium sulfate ($Li_2SO_4$), Ammonium sulfate (($NH_4)_2SO_4$), Potassium sulfate ($K_2SO_4$), Magnesium sulfate ($MgSO_4$), Potassium phosphate ($KH_2PO_4$), Sodium phosphate ($NaH_2PO_4$), Ammonium phosphate ($NH_4H_2PO_4$), Magnesium phosphate ($MgHPO_4$), Magnesium chloride (Mg $Cl_2$), Lithium chloride (LiCl), Sodium chloride (NaCl), Potassium chloride (KCl), Cesium chloride (CaCl), Ammonium acetate, Potassium acetate, Sodium acetate, Sodium fluoride (NaF), Potassium fluoride (KF), Tetramethyl ammonium chloride (TMA-Cl), Tetrabutylammonium chloride (TBA-Cl), Trimethylammonium chloride (TEA-Cl), and Methyltriethylammonium chloride (MTEA-Cl).

We have investigated variables that affect condensation of DNA in vitro and the functional relevance of these parameters for efficient delivery of DNA complexes into animals by receptor-mediated endocytosis. We noted a strong correlation between the ionic strength at which the condensed DNA-poly-L-lysine complex remains stable in solution and the concentration of DNA. These experiments were performed using a 4.5 kb plasmid containing the promoter from the gene for PEPCK linked to the structural gene for hFIX, using a ratio of DNA to poly-L-lysine that resulted in a 1 to 1 ratio of negative to positive charges in solution. The variation in the final concentration of NaCl necessary to solubilize the particles is a logarithmic function of DNA concentration, in which the condensation of highly concentrated DNA-poly-L-lysine complexes occurs with only a slight increase in ionic strength. This physical characteristic of DNA condensation has clear advantages for the delivery of the DNA particles to tissues of adult animals in vivo since it has little effect on the ionic load in the animal's blood.

The linear fit of the data using the least square method is described by the following function:

$$\log_{10}(\text{NaCl, mM}) = b0*(\text{DNA}, \mu\text{M Phosphate}) + b1 \quad r2=0.97$$

where b0=2.52×10E−3, b1=0.577

We have observed variations in the function described by the above equation when we use different DNA plasmids and different DNA preparations during the condensation process. These differences are probably related to the variation in the affinity of poly-L-lysine for DNA of different sources and compositions. For maximum binding affinity we generally use DNA precipitated twice with sodium acetate and 2.5 volumes of −40 C ethanol (see Methods). We have not found an apparent difference in binding affinity of poly-L-lysine for DNA of different forms (i.e., supercoiled, nicked and linear) and for DNA extracted using anionic exchange chromatography or cesium chloride gradient centrifugation. This may indicate the presence of a contaminant in the DNA preparations from different sources which has poly-L-lysine binding activity, that is eliminated by sequential DNA precipitation.

Figure 19:
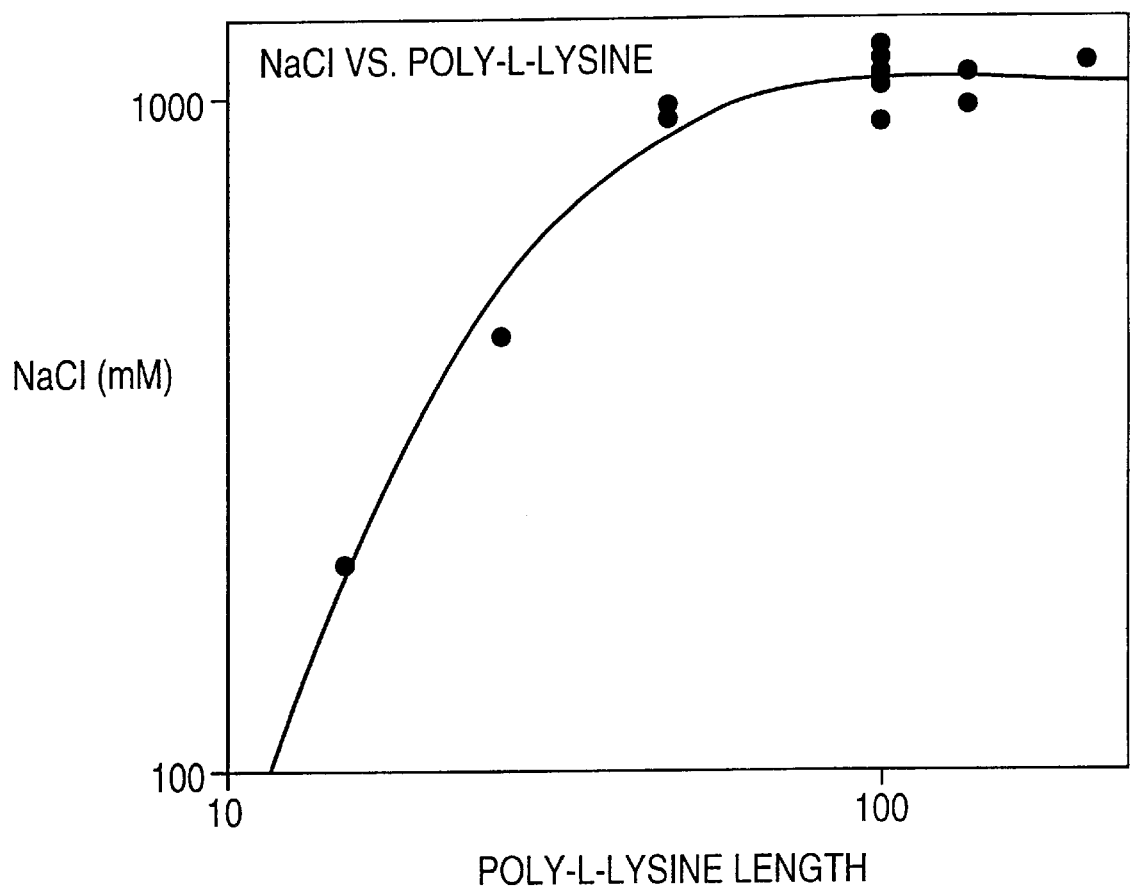
Figure 20A:
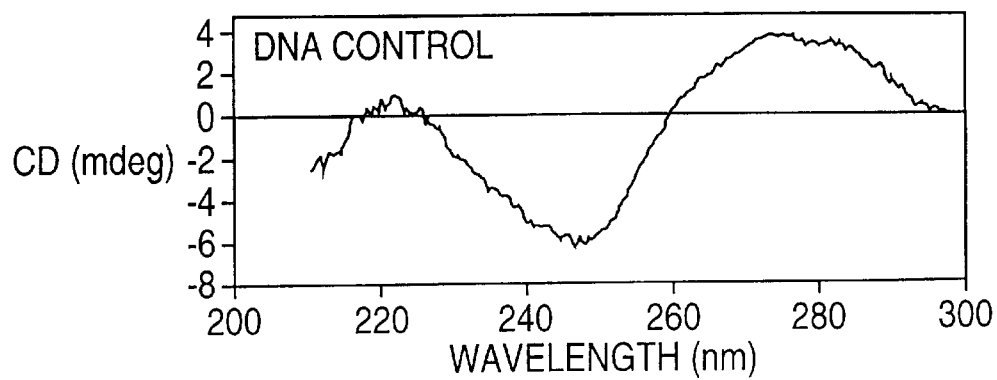
Figure 20B:
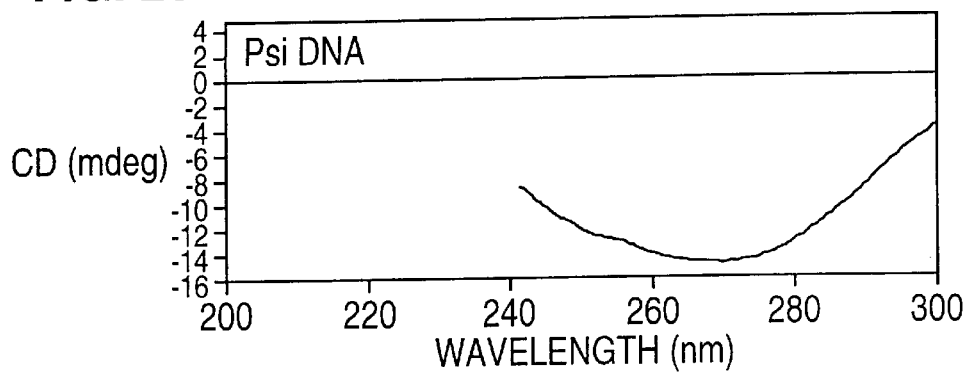
Figure 20C:
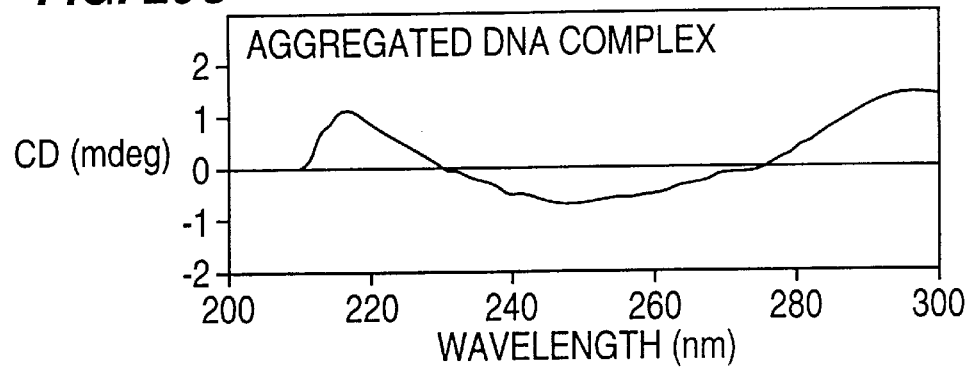
Figure 20D:
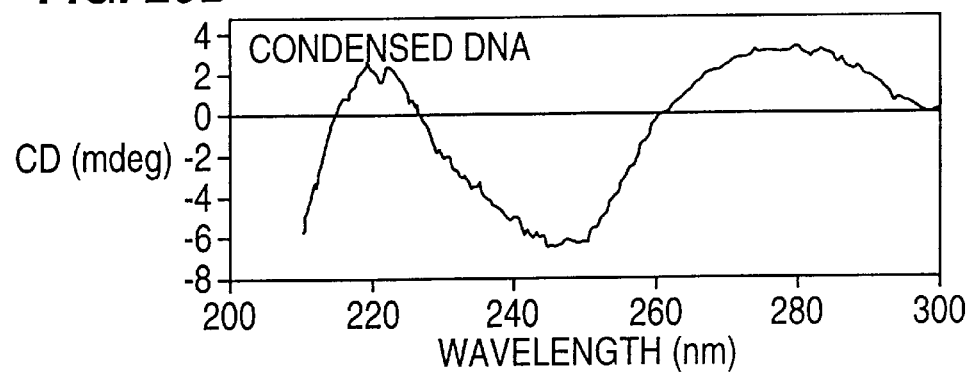
Figure 20E:
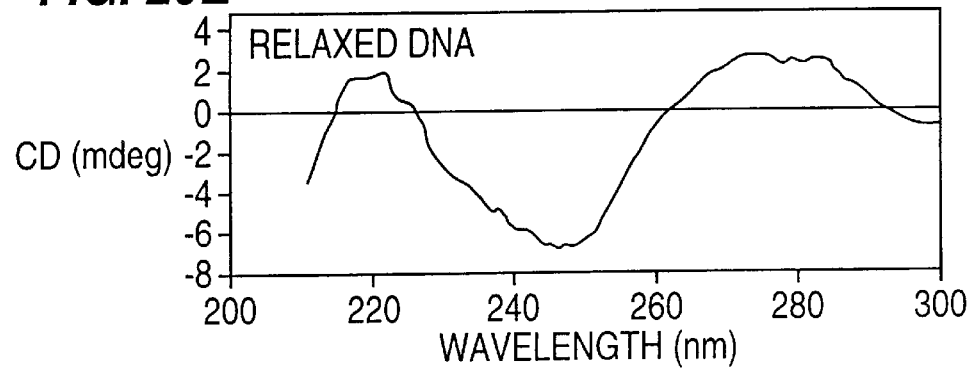

We have also investigated the effect of the length of the poly-L-lysine on the concentration of NaCl necessary for the effective condensation of DNA (FIG. 19). The correlation between these variables was assessed using a fixed concentration of DNA from different sources. We have used a broad range of poly-L-lysine lengths; essentially the sizes of poly-L-lysine available commercially. However, the length of the poly-L-lysine in an average of various sizes of the protein as determined by lowangle light scattering analysis of individual lots of chemically synthesized poly-L-lysine. The actual distribution of sizes within each sample varies from 60 to 80% of the material being distributed, which is +/−20% from the average size. This broad distribution within a single size is a source of error in our determinations. Nevertheless, there is a clear correlation observable in FIG. 19 between the length of the poly-L-lysine and the necessary concentration of NaCl needed for the condensation of the DNA complex in solution. This correlation is a linear function of poly-L-lysine length up to a size of 150 lysine residues, after which the function reaches saturation and there is no increase in the concentration of NaCl needed for the condensation of DNA with longer poly-L-lysine. These data are consistent with a cooperative binding between the poly-L-lysine and the DNA phosphate backbone. Thus, by reducing the length of the poly-L-lysine molecules used to condensed the DNA the solution of DNA complex injected into the animals will be less hypertonic. It is also important to consider the dilution of the DNA complex in the blood of the animal to evaluate the functional significance of these changes in ionic strength on the efficiency of this method for gene therapy. We have injected rats with DNA complexes containing longer range of poly-L-lysine lengths than those shown in FIG. 19 and rabbits with the shorter range of sizes of poly-L-lysine, and noted positive and persistent expression of the transfected genes in both cases.

The preferred minimum initial salt concentration is dependent on the compaction activity of the carrier and the chaotropic activity of the salt. If the NABM were $(\text{Lys})_8$, or $(\text{Lys})_{27}$, the initial NaCl concentration could be zero. With longer polyLys chains, however, in the absence of NaCl, precipitation would be immediate. With $(\text{Lys})_{50}$, the initial NaCl concentration is preferably be at least about 300 mM. Nonetheless, if the TBM is a protein that affects the condensation, the initial salt concentration could be as low as zero.

The carrier may be added continuously, or in small discrete steps. One may begin with a higher flow rate, or larger aliquots, and reduce the flow rate or aliquot size as the desired endpoint of the reaction is neared. Typically 0.1 to 10% of the carrier solution is added at a time to the DNA solution. Each addition is preferably made every 2 seconds to 2 minutes, with constant vortexing. However, longer settlement times may be allowed.

In one embodiment, a nucleic acid, contained in a salt solution, which is preferably at least 0.5M, but less than 1.5M NaCl, is mixed with poly-L-lysine (109 lysines) containing the covalently linked target cell binding moiety (for example, galactose), which is contained in a solution of NaCl at the same concentration (e.g., 0.5 to 1.5M NaCl). Preferably, the molar ratio of nucleic acid phosphate group to positively charged group of the DNA binding moiety is in the range of 4:1 to 1:4, and more preferably is about 1.5:1.

Some of Applicants' experimental results are set forth in Table 104. We have taken 16 examples (asterisked in the first column of Table 104) which were tested and worked in vivo, and regressed final NaCl concentration (the independent variable) against DNA concentration and poly-L-Lys length (the dependent variables), with the results given in Table 105.

The Conjugation

In the embodiments relying on a target-binding carrier molecule, the nucleic acid binding moiety will be conjugated, covalently or noncovalently, directly or indirectly, to the target cell binding moiety. The conjugation may be performed after, or, more usually before, the loading of the nucleic acid binding moiety with the nucleic acid of interest. Either way, the conjugation should not substantially interfere with the binding of the nucleic acid to the nucleic acid binding moiety, or, for that matter, with the ability of the target cell binding moiety to bind to the target cell.

Pharmaceutical Compositions And Methods

The compacted nucleic acid, optionally conjugated with a TBM, may be admixed with a pharmaceutically acceptable excipient (i.e., carrier) for administration to a human or other animal subject. It will be appreciated that it is possible for a DNA solution to contain both condensed DNA and relaxed DNA. The compositions of this invention preferably are sufficiently rich in condensed complexes so that the absorbance at 260 nm is less than 50% that of naked DNA of equal concentration. As stated in Table 103, condensed DNA usually has an absorbance of 20–30%, and relaxed DNA, 80–100%, that of naked DNA.

The administration may be by any suitable route of administration. The dosage form must be appropriate for that route. Suitable routes of administration and dosage forms include intravascular (injectable solution), subcutaneous (injectable solution, slow-release implant), topical (ointment, salve, cream), and oral (solution, tablet, capsule). With some routes of administration, the dosage form must be formulated to protect the conjugate from degradation, e.g., by inclusion of a protective coating or of a nuclease inhibitor.

The dosage may be determined by systematic testing of alternative doses, as is conventional in the art.

Rats (200–300 g) tolerate as much as 600 $\mu$g doses of the DNA complex of Example 1 without any apparent ill effects on growth or health. Mice (25 g) have been injected with 150 $\mu$g of that DNA complex without any apparent problem.

In humans, a typical trial dose would be 60–120 mg of DNA; if this dose is too low to be effective or so high as to be toxic, it may be increased, or decreased, respectively, in a systematic manner, until a suitable dose is identified.

For short life span cells, e.g., macrophages, a typical dosing schedule might be one dose every two weeks. For long life span cells, e.g., hepatocytes, one dose every two months might be preferable.

Adjuvants may be used to decrease the size of the DNA complex (e.g., 2–10 mM MgCl), to increase its stability (e.g., sucrose, dextrose, glycerol), or to improve delivery efficiency (e.g., lysosomotropic agents such as chloroquine and monensine). The complexes may be enclosed in a liposome to protect them and to facilitate their entry into the target cell (by fusion of the liposome with the cell membrane).

EXPERIMENTAL

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); CTAB (cetyltrimethylammonium bromide); fmol (femtomole); FPLC (fast protein liquid chromatography); HEPES (N-[2-Hydroxyethyl]piperazine-N-[2'-ethanesulfonic acid]); HPLC (high pressure liquid chromatography); DTT (dithiothreitol); DMF (N, N dimethyl formamide); DNA (deoxyribonucleic acid); i.d. (internal diameter); p (plasmid); μl (microliters); ml (milliliters); μg (micrograms); pmoles (picomoles); mg (milligrams); MOPS (3-[N-Morpholino]propanesulfonic acid); M (molar); mM (milliMolar); μM (microMolar); nm (nanometers); kdal (kilodaltons); OD (optical density); EDTA (ethylene diamine tetra-acetic acid); FITC (fluorescein isothiocyanate); LC sulfo SPDP (LC sulfo-N-succinimidyl-3-(2-pyridyldithio)proprionate); SDS (sodium dodecyl sulfate); $NaPO_4$ (sodium phosphate); Tris (tris (hydroxymethyl)-aminomethane); PMSF (phenylmethylsulfonylfluoride); TBE (Tris-Borate-EDTA, e.g., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); Boehringer Mannheim or BM (Boehringer Mannheim, Indianapolis, Ind.); New England Biolabs or NEB (New England Biolabs, Beverly, Mass.); Novagen (Novagen, Inc., Madison, Wis.); Pharmacia (Pharmacia Biotech Inc., Piscataway, N.J.); Perkin Elmer (Perkin Elmer, Norwalk, Conn.); Pierce (Pierce Chemical Co., Rockford, Ill.); Promega (Promega Corp., Madison, Wis.); Qiagen (Qiagen Inc., Chatsworth, Calif.); Stratagene (Stratagene Cloning Systems, La Jolla, Calif.); USB or U.S. Biochemical (U.S. Biochemical, Cleveland, Ohio).

EXAMPLE 1

Introduction

Christmas disease, or Hemophilia B, is a sex-linked recessive bleeding disorder due to a deficiency of functional coagulation factor IX in the circulation. Human factor IX (hFIX) is a plasma glycoprotein normally synthesized in the liver, that plays an integral role in the intrinsic coagulation pathway. Once it has been converted to its serine protease form (IXa) by activated plasma thromboplastin antecedent (factor XIa), the activated protein interacts with coagulation factor VIIIa, calcium ions, and phospholipids to produce a complex that converts factor X to Xa. Factor IX undergoes several post-translational modifications in the liver that are essential for its function before secretion into the blood. These include Vitamin K dependent γ-carboxylation of amino-terminal glutamic acid residues and β-hydroxylation of aspartic acid.

Christmas disease accounts for approximately 10 to 20 percent of all inherited clotting disorders. Affected individuals exhibit a wide range of clinical severity that generally correlates with the level of circulating factor IX. Patients with severe deficiencies of functional factor IX may bleed spontaneously into soft tissues and joints or after minor trauma. Transfusions of plasma or concentrates rich in factor IX are used to abort bleeding episodes by temporarily correcting the deficiency. Unfortunately, clinical management has been confounded by viral contamination of pooled plasma. Blood-borne infections, such as hepatitis and the acquired immunodeficiency syndrome, have become significant problems in the treatment of the hereditary clotting disorders. These complications stress the importance of developing alternative treatments.

The gene for human coagulation factor IX has been identified and sequenced; 1,248 base pairs, in length, the complementary DNA predicts a protein of 416 amino acids, and, after post-translational modifications, the mature protein has a molecular weight of approximately 54,000 Da. A gene encoding human coagulation factor IX may be used for genetic correction of hemophilia B.

A chimeric P-enolpyruvate carboxykinase-human factor IX(PEPCK-hFIX) gene (50% supercoiled/ 50% open circular) was condensed with galactosylated poly-L-lysine (average length 50 or 109 amino acids) by titration with NaCl. This process was monitored using CD spectroscopy and electron microscopy and resulted in the formation of a DNA-carrier complex of 10–12 nm in diameter at a critical NaCl concentration. We have introduced the PEPCK-hFIX gene, conjugated using this procedure, into the intact livers of adult rats and have demonstrated that the DNA-carrier complex specifically targets the gene to this organ and that hFIX DNA, mRNA and hFIX protein can be demonstrated up to 140 days (the duration of the experiment) after administration of the DNA-carrier complex. The gene is present as an episome as determined by Southern analysis of DNA isolated from the liver of an animal 32 days after injection of the DNA-conjugate. Transcription of the PEPCK-hFIX gene was controlled by diet for the entire time course of the experiment; feeding the animals a carbohydrate-free diet for one week resulted in the predicted induction of hFIX in the blood, as detected by Western blot hybridization.

Methods

A. Galactosylation

Polymers of L-lysine-HBr or L-lysine-Cl with an average chain length of 109 (Sigma) were galactosylated essentially as described by Monsigny, et al. (1984) Biol. Cell., 51, 187. Briefly, 2 mg of poly-L-lysine was reacted with 89 g of α-D-galactopyranosyl phenyl-isothiocyanate (Sigma G-3266) dissolved in N,N-Dimethyl formamide (5 mg/ml). The solution was adjusted to pH 9.0 by the addition of ⅒ volume of 1M sodium carbonate pH 9.0. Since the reaction is 10% efficient, 0.8% of the ε-$NH_3$ groups present in the solution are glycosylated. The tube was shielded from light by aluminum foil and mixed for 6 hours at room temperature. The solution was then dialyzed, using Spectra-Por dialysis tubing (Fisher 3500M.W. cutoff), against 500 ml of 5 mM NaCl buffer for 2 days with frequent changes of buffer (2 changes/day).

B. Analysis Of The ligand

The dialyzed solution was then analyzed spectrophotometrically at 205 Å and 250 Å for the concentration of poly-L-lysine and the concentration of phenyl-galactose residues, respectively. This step ensures that significant losses during dialysis have not occurred, and that the galactosylation reaction was complete, since in the solution only the modified galactose will absorb at 250 Å.

C. Complex Formation

Plasmid DNA was prepared using standard techniques. The DNA was re-suspended in 10 mM Tris-HCl, pH 8.0, containing 1 mM EDTA and the concentration of the DNA determined spectrophotometrically. The DNA preparation was digested twice with RNAses A+T1. This step ensures that RNA is not present in the solution (RNA inhibits the condensation of DNA by poly-L-lysine). A solution containing a high concentration of DNA (1.5–2 mg/ml) was used in further steps. An example of a typical protocol for DNA condensation is described as follows:

a) 300 μg of DNA in 200 μl of 0.75M NaCl (added from 5M NaCl solution) is vortexed at medium speed, using a VIBRAX machine (IKA-VIBRAX-VXR). This procedure is desirable to increase the effective length of the DNA polymer in high salt solutions, thus achieving efficient binding of the poly-L-lysine moiety to the DNA backbone.

b) 84 μg of poly-L-lysine-galactose in 200 μl of 0.75M NaCl (added from a 5M NaCl solution) is added dropwise over a period of 30 minutes to 1 hour in 20 μl aliquots. This amount translates into a molar ratio of 1 DNA $PO_4^-$ group to 0.7 carrier $NH_3^+$ groups.

c) The solution becomes turbid at the end of the process. 3 μl aliquots of 5M NaCl are added dropwise to the vortexing solution until turbidity disappears as monitored by eye. This process is slow, allowing 30 seconds between the addition of each new aliquot of 5M NaCl. Then the solution is subjected to CD spectroscopic monitoring while 2 μl aliquots of 5M NaCl are gradually added. The condensation process is complete when the diagnostic spectrum of the DNA complex is observed. For subsequent preparations of DNA complex consisting in the same plasmid DNA at the same concentration of nucleotide, the protocol can be followed without monitoring with CD and the results will be fully reproducible. When using different concentration of DNA or a different plasmid the CD monitoring should be repeated.

We have found that an alternative technique for monitoring DNA complex formation gives similar results. This technique consists of the following steps:

a) and b) Idem.

c) The solution becomes turbid at the end of the process. 3 μl aliquots of 5M NaCl are added dropwise to the vortexing solution until turbidity disappears as monitored by eye. This process is slow, allowing 30 seconds between the addition of each new aliquot of 5M NaCl. The solution is then centrifuged at full speed (12000× g) for 30 seconds using a microcentrifuge and the appearance of precipitate is monitored. If a precipitate is observed 2 μl aliquots of 5M NaCl are added. The solution is further vortexed for 0.5 minutes and the centrifugation step is repeated. The appearance of a precipitate is due to the aggregation of the DNA-complex in solution and indicates that the DNA has not been fully collapsed.

Results And Discussion

In developing the procedure described herein, we have monitored the physical structure of the DNA/ligand-poly-L-lysine conjugate using circular dichroism (CD) and electron microscopy and studied the conditions by which a functional complex is generated. We then determined the functional relevance of the physical structure of the DNA/ligand-poly-L-lysine conjugate using intact animals. The DNA was condensed by the addition of the ligand-poly-L-lysine in the presence of varying concentrations of NaCl. Either 60 μg of RNA-free CMV - β - galactosidase (A) or phFIX (B,C,D, and E), diluted to a final volume of 150 μl in 700 mM NaCl were vortexed at medium speed in a VIBRAX apparatus (IKA-VIBRAX-VXR). 19 μg of α-galactopyranosyl-phenyl isothiocyanate/poly-L-lysine biconjugate (Sigma) were diluted in the same way and added dropwise to the vortexing solution of DNA. For in vivo studies, 300 μg of DNA (dissolved in TE buffer, pH 8) in 150 μl of 700 mM NaCl were condensed with 95 μg of α-galactopyranosyl-phenyl isothiocyanate/poly-L-lysine biconjugate in 150 μl of 700 mM NaCl. The slow addition of the polycation results in the formation of a turbid solution which is dissolved by the stepwise addition of 3 μl aliquots of 5M NaCl. The disappearance of the turbidity was monitored by eye and at the point of no turbidity the solutions of DNA/poly-L-lysine complexes were investigated by both electron microscopy (E.M.) and CD spectroscopy.

Continuing addition of 2 μl aliquots of 5M NaCl resulted in structural changes as shown in FIGS. 1A–1F. Representative spectra demonstrating different structural conformations of the DNA complex at various concentrations of NaCl and in the presence and absence of added poly-L-lysine, are presented in FIG. 1. Polycation binding to DNA results in a specific spectrum characterized by a displacement of the cross-over to longer wavelengths; this shift can be correlated with the chiral packing of DNA/poly-L-lysine conjugates in high order, asymmetric structures similar to the Y-form of DNA. As shown in FIG. 1A, double stranded DNA (in 1M NaCl) has a characteristic spectrum which was markedly altered by the addition of poly-L-lysine at varying ionic strengths. (FIG 1a). When the ionic strength of the DNA/ligand-poly-L-lysine conjugate was increased the complex proceeded through a transition from an aggregated (FIG. 1C) to a condensed state (FIG. 1D & FIG. 1E). This corresponds to a shift in the spectrum of the complex as shown in FIG. 1A. The change in the CD spectra at 220 nm and the shift in the cross-over (0 line in FIG. 1A) that occurs with increasing ionic strength of the solution is of particular importance in monitoring the formation of condensed DNA complex by means of CD spectroscopy. If the ionic strength is increased above the critical range required for the condensation of the DNA complex, the complex assumes a non-condensed, relaxed conformation (FIG. 1F). This transition in the conformation of the DNA complex cannot be monitored by CD spectroscopy so that a rigorous titration of NaCl is critical to the success of this procedure. It is important to note that the diameter of the DNA complex observed in FIG. 1D (about 10 nm) conforms with the discrimination range desirable for internalization of molecular ligands by the hepatic receptor for asialoglycoproteins.

We therefore verified the functional relevance of the observed DNA structures as vehicles to transfer of the DNA into hepatocytes in vivo by receptor-mediated endocytosis. In order to establish the nature of the uptake process, we followed the removal of the DNA complex from the media by HepG2 cells, which contain the asialoglycoprotein receptor. The uptake of the DNA complex was completely inhibited when a 100-fold molar excess asialogetuin was used as a competitor, indicating that the complex was being taken up by receptor-mediated endocytosis via the ASGP.

A plasmid (pPFIX) containing a chimeric gene composed of the promoter of the gene for the cytosolic form of P-enolpyruvate carboxydinase (PEPCK) from the rat, linked to the cDNA for human coagulation Factor IX (hFIX) (Ferkol, et al., FASEB J., 7:1081 (1993)) was used to follow the delivery and expression of the DNA in the liver. The time-course of expression of hFIX gene in the transfected animals was determined by Western blot hybridization, using a monoclonal antibody against the mature hFIX peptide.

Adult, male Sprague-Dawley rats, approximately 250 g in weight, were anesthetized with ether. 300–400 $\mu$l of a solution containing 300 $\mu$g of pPFIX complexed as previously described with galactose-poly-L-lysine, were infused into the caudal cava vein. Rats were killed at 0, 4, 8, 12, 32, 72 and 136 days after transfection and tissues and blood samples taken.

Plasma samples (1 $\mu$l) from transfected animals and a 1:4 dilution of a human plasma control were subjected to electrophoresis in SDS/10% polyacrylamide gels and transferred onto nitrocellulose membrane filters using standard techniques. The blots were block with 1× PBS, pH 7.4, 0.03% polyoxyethylene sorbitan monolaurate (Tween 20), and 10% (w/v) dry skim milk for two hours at room temperature, followed by incubation with a 1/1000 dilution of a monoclonal murine anti-human factor IX antibody (3 $\mu$g/ml) for two hours at room temperature. The monoclonal antibody was kindly provided by Dr. Kenneth Smith (United Blood Services, Albuquerque, N.Mex.). The membrane was washed three times in 1× PBS, pH 7.4 and 0.03% Tween 20, then incubated with a 1/500 dilution of goat anti-murine 1 gg (H+L)—horseradish peroxidase conjugate. The membrane was then washed vigorously four times with 1× PBS, pH 7.4 and 0.03% Tween 20, and 10 ml of Western blot enhanced chemiluminescence detection solution was applied for one minute. The luminescence emitted from the filter was detected by a 20 second exposure to photographic film. We detected a band hybridizing specifically to the hFIX monoclonal antibody for as long as 140 days. No hybridizing band was detected in untransfected controls.

The liver from an animal 32 days after transfection was taken and genomic DNA isolated using standard techniques. 5 $\mu$g of total DNA from the transfected animal and from a non-transfected control were digested with either EcoRI or BglII overnight. Southern blot electrophoresis was performed by established methods. The DNA from the transfected animal only hybridized to 4.5 kb BglII and a 2.6 kb EcoRI probes.

Spleen, lung, heart and liver tissues were obtained from a rat transfected with 300 $\mu$g of the DNA complex. PCR analysis was carried out on total genomic DNA isolated from these tissues. Only the liver of the transfected rat, and not its spleen, lung or heart, or the liver of a control animal, was positive for the 720 bp probe.

The presence of mRNA transcripts for human factor IX in the livers of rats transfected with pFIX was determined after treatment of total cellular hepatic RNA with Moloney Murine Leukemia virus reverse transcriptase and amplification of the resultant cDNA by the polymerase chain reaction. Briefly, 1 $\mu$g of total rat liver RNA was treated with 10 U DNAse I (RNAse free), and added to a solution containing 500 nM of $(dT)_{16}$ oligonucleotide primer and 500 nM of each dNTP, and heated to 42° C., and 1 $\mu$l of the cDNA pool was amplified by the polymerase chain reaction, using primers expanding the 5' UTR region of the PEPCK promoter and the cDNA for hFIX. As a control, the same RNA samples not converted to cDNA by reverse transcriptase were also used as polymerase chain reaction templates to ensure that contaminating plasmid DNA had not been amplified. The products were separated by agarose gel electrophoresis and Southern blot hybridization using a radiolabeled human factor IX cDNA probe. We observed a band that hybridized specifically with the hFIX probe only in the transfected animals. No bands were detected in either non-transfected controls or transfected samples not converted to cDNA by reverse transcriptase.

The functional activity of hFIX in the plasma of transfected animals was analyzed by measuring the procoagulant activity of human Factor IX. A modification of the one stage, kaolin-activated, partial thromboplastin time with factor IX-deficient human plasma was used. Blood samples were obtained from experimental animals by venipuncture. One fiftieth volume of 500 mM sodium citrate pH 5.0, was added to prevent coagulation, and the plasma was stored at 20° C. The samples were assayed in duplicate, and their activity was compared to the functional activity of pooled plasma from 24 normal adult human males. In normal human plasma is equivalent 100% functional activity or approximately 3 $\mu$g of human Factor IX per ml. Background Factor IX activity in rat plasm (approximately 0.15 units/ml of Factor IX activity in rat serum) was subtracted from each value of human Factor IX determined in individual animals. The background values is non-specific cross activity of rat Factor IX determined in the human Factor IX assay used in this analysis. Blood samples were obtained from experimental animals by venipuncture. One fiftieth volume of 500 mM sodium nitrate, pH 5.0, was added to prevent coagulation, and the plasma was stored at 20° C. The normal concentration of hFIX in human plasma is 3 $\mu$g/ml, Approximately 15 ng/ml (72 days after transfection) to 1050 ng/ml (48 days after transfection) of active human factor IX were produced in individual animals injected with the DNA complex (Table 102). It is not clear if the small variations in the concentration of recombinant hFIX found in the animals represent a difference in delivery efficiency or in the expression of the newly introduced gene. The hFIX gene was expressed in the animals for up to 140 days (the duration of the experiment), with the highest level noted at 48 days (Table 102).

It has been established using transgenic animals (McGrane, et al., 1988, 1990; Short, et al. 1992) that transcription from the PEPCK promoter can be induced by the administration of a high protein-low carbohydrate diet. In order to demonstrate the regulated expression of the transgene, we analyzed the blood of transfected animals for the presence of hFIX by Western blot hybridization before and after feeding a high protein-low carbohydrate or a normal chow diet for 1 week. We noted up to 3-fold induction of PFIX gene expression in animals containing the PFIX gene for up to 140 days after injection of the DNA complex. The same PEPCK-hFIX gene, introduced into the livers of rats using an alternative method of receptor-mediated gene transfer targeting the ASGE, was active for only two days (Ferkol, et al., 1993); this suggests that the use of a highly compacted DNA complex may be responsible for the prolonged expression of the transgene noted in the present study.

Figure 3:
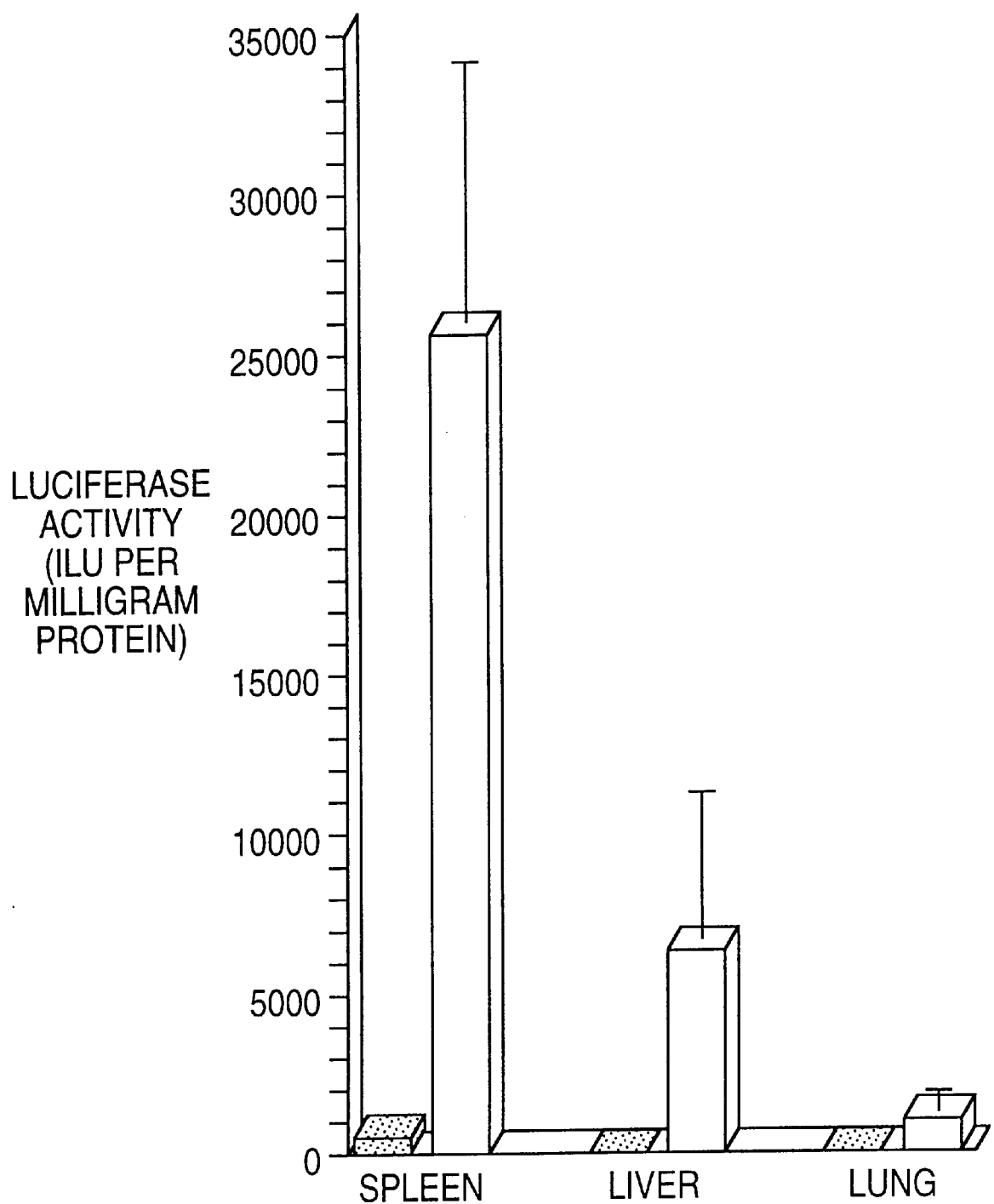
Figure 4:
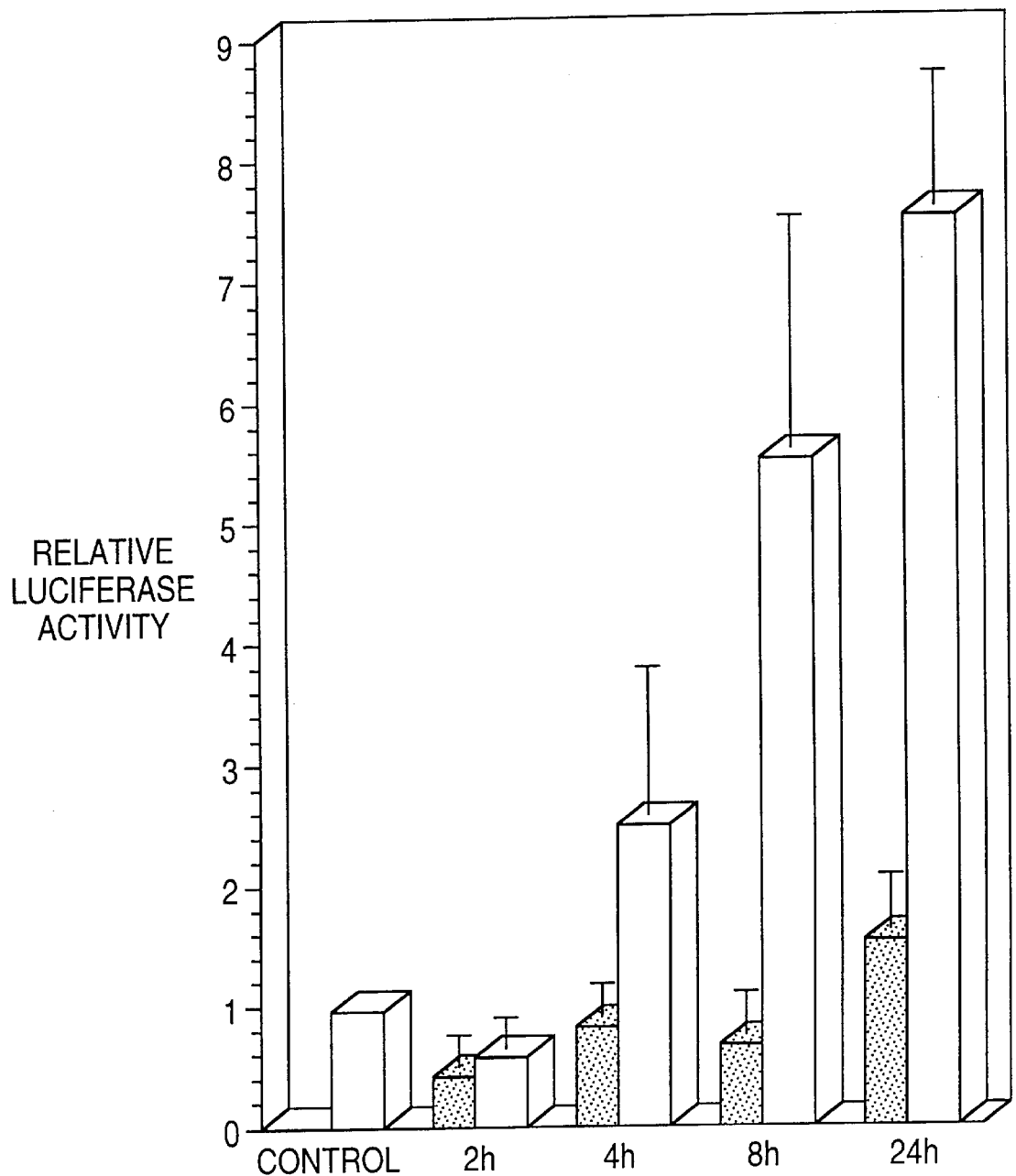
Figure 5:
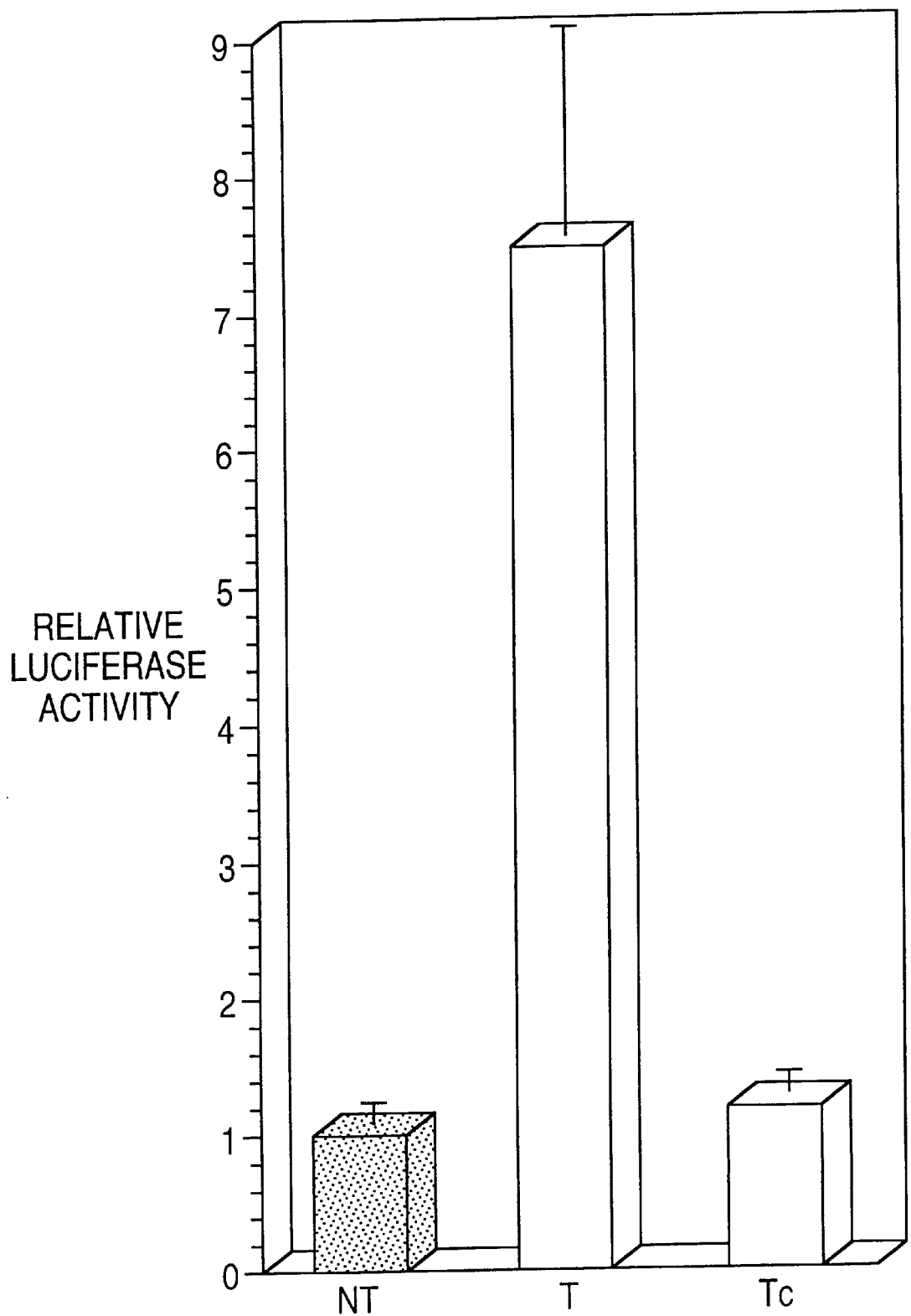
Figure 6:
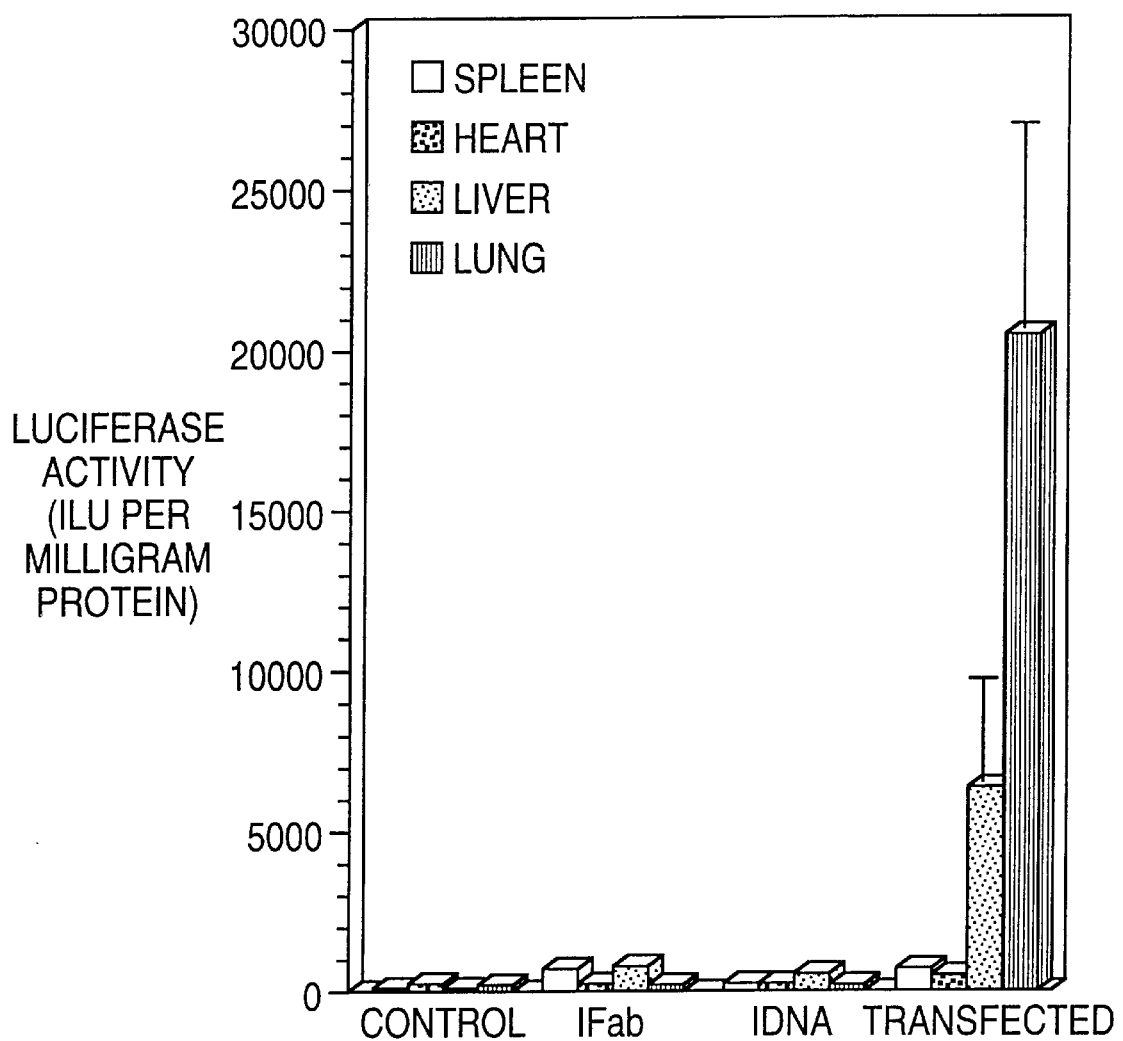
Figure 7:
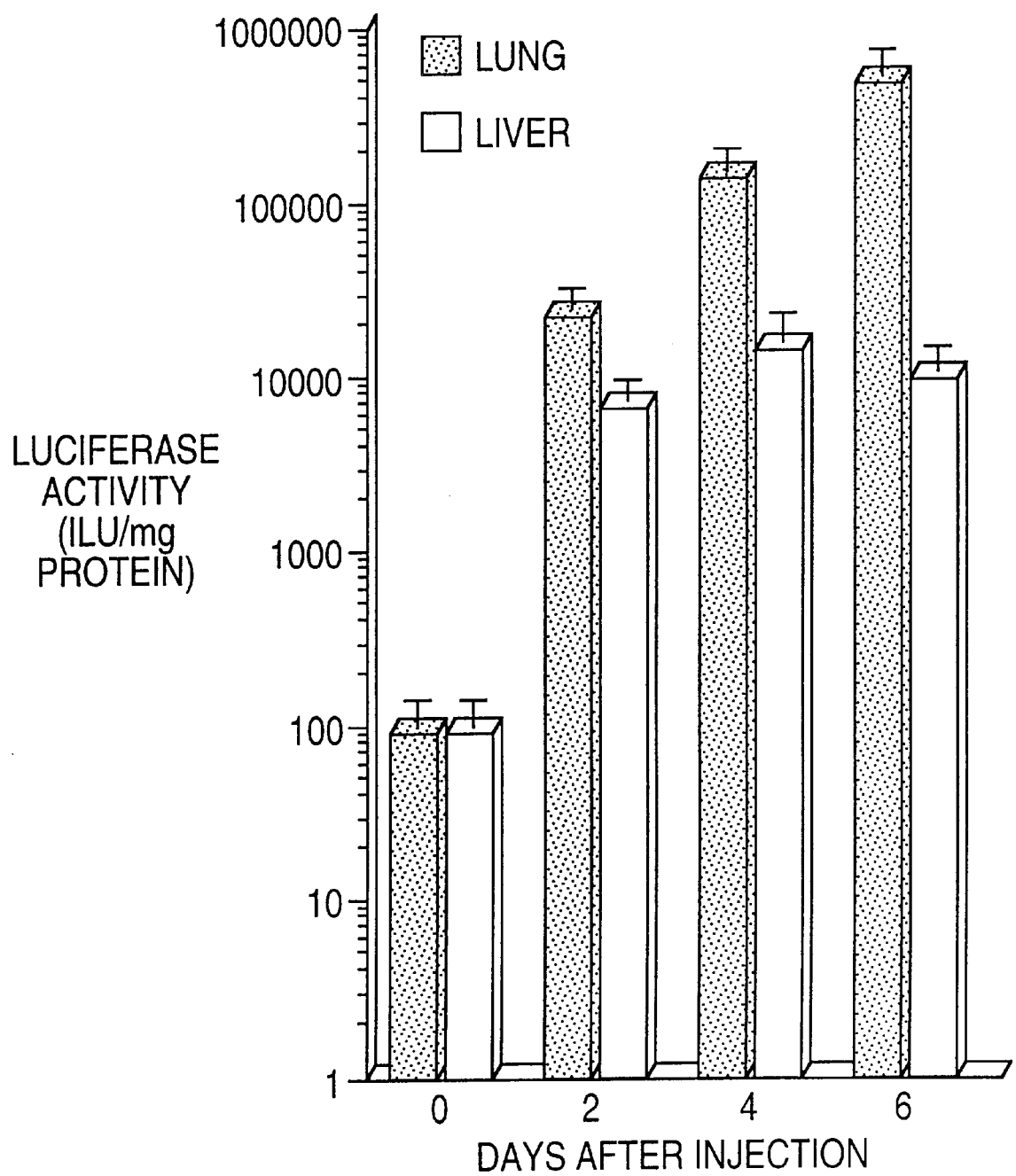
Figure 8:
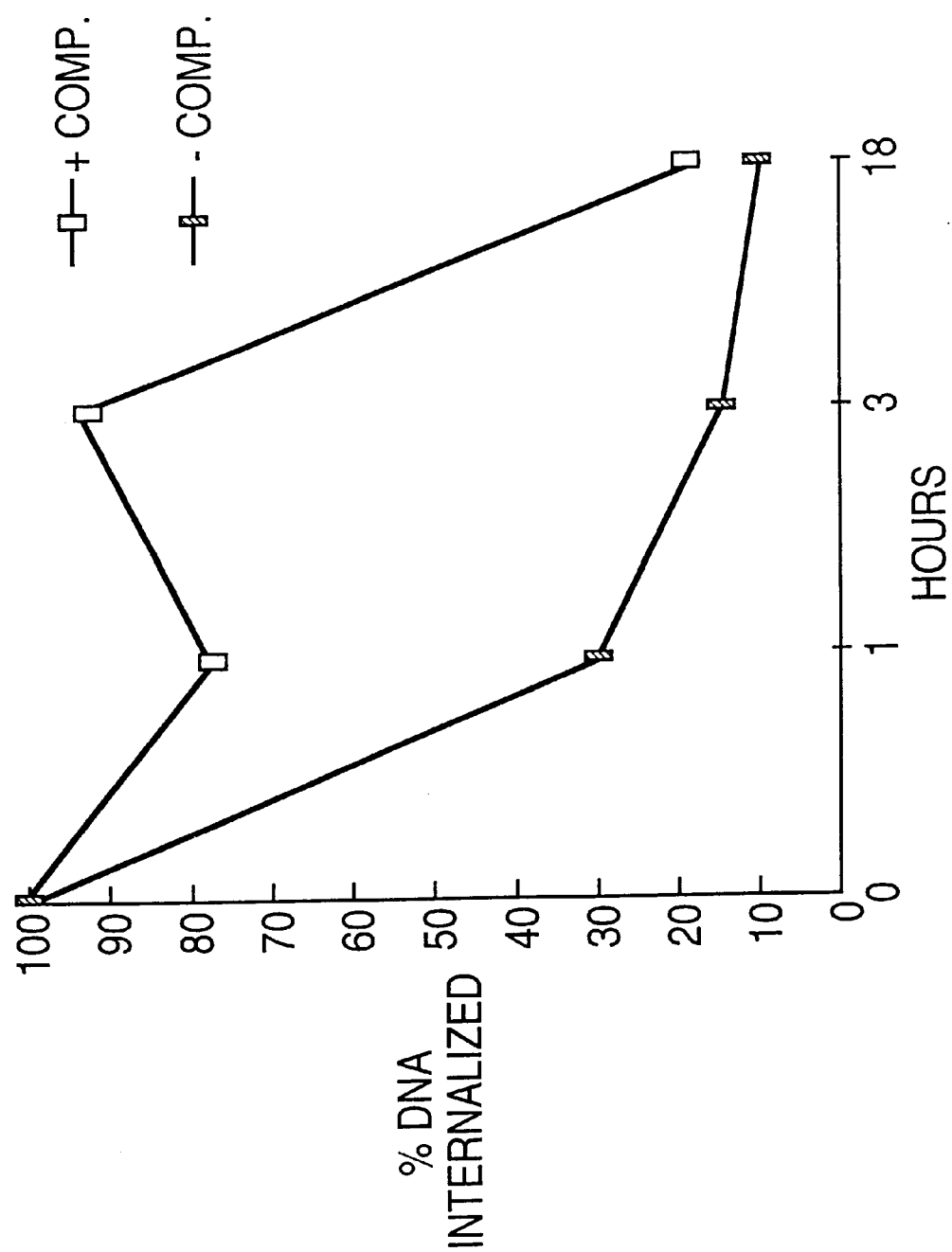

Detection of maintained levels of hFIX protein at time points as long as 140 days is evidence for expression throughout the experimental time course. A human FIX 800 bp. specific transcript was detected by PCR amplification of cDNA generated from total cellular RNA by reverse transcriptase, in the livers of animals expressing functional hFIX protein (FIG. 3A). The presence of mRNA along the experimental time-course would indicate that there is a maintained pool of transcriptionally active DNA in these animals which persistence will explain the prolonged expression and detection of hFIX and specific mRNA.

We have also established the presence of the transfected DNA in the liver of animals 32 days after transfection, and investigated its physical state. The DNA extracted was subjected to restriction enzyme analysis with BglII that linearizes the plasmid (4.5 Kb) and with EcoRI that releases the 2.6Kb chimeric gene from the plasmid. Southern blot hybridization using a hFIX specific probe demonstrated that the transfected DNA remains in episomal state in the transfected livers, since BglII produced a single band consistent with the size of the linear plasmid in contrast to the expected smeared hybridization when random integration occurs (FIG. 3B). We cannot rule out the possibility that a small proportion of the transfected DNA may have undergone random integration into the genome of the transfected animals. However, we believe that this event is improbable since the liver has not been subjected to stimulation of mitosis (i.e., partial hepatectomy).

The asialoglycoprotein receptor is present only in parenchymal cells of the liver. Nevertheless, it has been shown that asialoglycoproteins and other galactose terminal ligands can be taken up by macrophages by a mechanism dependent on the size of the molecular ligand. See Schlepper-Schäfer, J. et al., *Exp. Cell. Res.* 165:494 (1986); Bijsterbosch, M. K., et al., *Mol. Pharmacol* 36:484 (1989); and Bijsterbosch, M. K., et al., *Mol. Pharmacol* 41:404 (1992). The size of the DNA/ligand-poly-L-lysine complex in our experiments would be compatible with the discriminating range of the asialoglycoprotein receptor. In order to investigate the specificity of the DNA complex we have obtained DNA from different tissues in a transfected animal and amplified the transfected DNA by PCR. Our results show the absence of amplifiable DNA in tissues other than liver, which would indicate specific uptake by hepatocytes. It is especially interesting that there is no detectable uptake in macrophage-containing tissues like lung and spleen. In contrast, we have detected transfected DNA in the lung and spleen of animals transfected using the method described by Wu, et al. for receptor-mediated endocytosis by means of the asialoglycoprotein receptor. We believe that the small size of the molecular ligand achieved in our experiments is responsible for the specificity of uptake reported here.

EXAMPLE 2

In this Example a different promoter-gene construct (SV40/luciferase) is delivered to a different cell type (macrophages) by means of a different target cell binding moiety.

Introduction

The recognition and uptake of circulating glycoproteins by specific cells are determined by the nature of the exposed sugar residues present on the surface of the molecule. The clearance systems of specific glycoproteins are relatively exclusive and are mediated by specific types of cells. The mannose receptor recognizes glycoproteins with mannose, glucose, fucose, and N-acetylglucosamine residues in exposed, non-reducing positions. Various proteins and glycoprotein conjugates bearing these carbohydrate residues bind to isolated alveolar macrophages, and mannose-terminal glycoproteins infused into the circulation of rats are cleared by Kupffer cells in vivo. Conversely, galactose-terminal glycoproteins, which are cleared by the asialoglycoprotein receptor on hepatocytes, are not recognized by these cells. This cell-surface receptor is expressed by a variety of macrophage subtypes but not circulating monocytes, and mediates the delivery and internalization of mannose-terminal glycoproteins. The mannose receptor recycles constituitively from a pre-lysosomal compartment to the cell surface, and receptor expression is regulated by macrophages.

Macrophages present in various organs (i.e., liver, spleen, lung, and bone marrow) which bind mannose-terminal glycoproteins and therefore may be a target cell for receptor-mediated gene transfer. We tested this hypothesis by examining our ability to deliver functional exogenous genes cells which express the mannose receptor. In this report, a mannose-terminal neoglycoprotein carrier was synthesized and employed as a ligand for receptor-mediated gene transfer to primary murine macrophages isolated from the peritoneal exudates, which abundantly express the receptor on their surface. In addition, the reporter genes were transferred successfully into macrophages present in the liver and spleen of intact rats using the mannose-terminal neoglycoprotein carrier.

Methods

Materials: DNA-modifying enzymes, nucleotides, and 5-Bromo-4-chloro-3-indolyl-α-D-galactopyranoside were purchased from Boehringer Mannheim (Indianapolis, Ind., USA). All chemicals, including poly (L-lysine), a-D-mannopyranosylphenyl isothiocyanate albumin, and a-D-galactopyranosylphenyl isothiocyanate, were obtained from the Sigma Chemical Company (St. Louis, Mo., USA). Luciferase assay system was obtained from Promega (Madison, Wis., USA). The rabbit anti-p-galactosidase antibody and fluorescein isothiocyanate-conjugated goat anti-rabbit IgG was obtained from the 5 Prime to 3 Prime, Inc. All media, sera, and antibiotics were obtained from Gibco Laboratories (Grand Island, N.Y., USA).

Preparation Of Mannose-Terminal Glycoprotein Carrier: Synthetic glycoprotein carriers were constructed in which poly (L-lysine), average chain length 100 ($M_r$ 20,000 Da), was glycosylated using a-D-mannopyranosyl phenylisothiocyanate dissolved in N,N-dimethylformamide. The solution was adjusted to pH 9.5 by the addition of 1M Sodium carbonate, pH 9.5. Shielded from light and incubated for 16 hours at 22∞C, the solution was dialyzed against 5 mM Sodium chloride for two days. Approximately 0.8 to 1.0% of the amine side chains in the polylysine are glycosylated, as determined by absorbance spectroscopy at 250 nm. As a control, an alternative glycoprotein carrier was synthesized by substituting a-D-mannopyranosyl phenylisothiocyanate with a-D-galactopyranosyl phenylisothiocyanate.

Reporter Genes And Plasmid Preparation: The expression plasmid pGEMluc contained the SV40 viral promoter and enhancer elements ligated to the *P. pyralis* luciferase gene. The plasmids pCMVZ and pCMVIL2r, consisting of the cytomegalovirus (CMV) promoter linked to the *E. coli* lacZ and the interleukin 2 receptor genes, respectively, were also used as reporter genes. The plasmids were grown in *E. coli* DH5a, extracted, and purified by standard techniques (14). Digestions of the plasmids with restriction endonucleases yielded the appropriate size fragments, and purity was established by 1.0% agarose gel electrophoresis. The sizes of plasmids are as follows: pGEMluc, 6.0; pCMVlacZ, 10.9; and pCMVIL2r, 5.4 kB. No bacterial genomic DNA was present in the plasmid preparations.

Preparation Of Mannose-Terminal Glycoprotein Carrier-DNA Complexes: Complexes were formed analogously to Example 1, however, the DNA was about 80% supercoiled and 20% open circular.

Cells And Cell Culture: Primary macrophages were isolated from the peritoneal cavity of mice four days after the intraperitoneal injection of one milliliter of Brewer's thioglycolate medium. The macrophages from the peritoneal exudate were collected as previously described, and maintained in RPMI Media 1640. This method yielded approximately $5 \times 10^6$ cells per mouse, of which 40–75% were mononuclear phagocytes based on morphological characteristics of the cells and cytochemical identification. Transfections were performed one or two days after collection. The isolated cells were approximately 30–60% confluent at the time of transfection. Viability of cells was determined by serial cell counts and trypan blue exclusion.

DNA Delivery To Macrophages In Culture: One day after isolation, the cells isolated from the peritoneal exudates of mice were washed once with PBS (pH 7.4) and the media was changed immediately before transfection. The conjugate-DNA complex, containing 5 $\mu$g (0.4–0.7 pmol) plasmid, was applied to the culture medium and permitted to remain on the cells for 24 hours unless the experiment dictated otherwise. The cells were then either harvested for protein extraction or fixed for in situ $\beta$-galactosidase assays at several timepoints after transfection.

Animals: Adult, male Sprague-Dawley rats, weighing approximately 250 g., were anesthetized with ether. Using aseptic technique, 0.3 to 0.6 ml of a solution containing 300 $\mu$g (20.8–42.0 pmol) of an expression plasmid complexed to the carrier was injected into the caudal vena cava. The rats were killed at different intervals after infusion of the complexes and the livers, lungs, and spleens of transfected animals were removed for analysis. Furthermore, macrophages were isolated from the alveoli, the bone marrow, and spleen. Bone marrow cells were obtained from the rat's femur. The femur was surgically removed after the experimental animal was sacrificed, and one milliliter of media was infused into and aspirated from the marrow cavity. A single-cell suspension of the marrow was prepared by gently aspirating the cells with a Pasteur pipette. The cells extracted from the bone marrow were maintained in RPMI Media 1640 for 8–12 hours and permitted to attach to glass slides, at which time the adherent cells were fixed for immunocytochemical staining. Non-transfected and mock transfected animals were used as controls in all analyses. The animal research protocol was reviewed and approved by the Case Western Reserve University Institutional Animal Care Committee.

Cytochemical Assay For $\beta$-Galactosidase Activity: Individual cells expressing $\beta$-galactosidase were identified following incubation with 5-Bromo-4-chloro-3-indolyl-$\beta$-galactopyranoside (X-gal) as described previously. Briefly, the cells were fixed with a solution of 1% glutaraldehyde in PBS for 15 minutes, and then incubated with a solution containing 0.5% X-gal for 12 hours at 37° C. The cells were also stained for nonspecific esterase activity, which produces an insoluble grey-black dye. A minimum of 100 cells in tissue culture were counted to determine the percentage of cells expressing $\beta$-galactosidase.

Individual cells expressing $\beta$-galactosidase in tissues were identified following incubation with X-gal as described previously. Briefly, the cells were fixed with a solution of 0.5% glutaraldehyde in PBS for 10 minutes, washed twice with PBS, pH 7.5, and then incubated with a solution containing 0.5% X-gal, 5 mM Potassium ferricyanate, 5 mM Potassium ferrocyanate, and 1 mM Magnesium chloride in phosphate-buffered saline (pH 7.4) for 6 hours at 37° C. The stained tissues were fixed in 2% paraformaldehyde/0.5% glutaraldehyde in PBS overnight at 4° C., paraffin embedded by standard procedure, and cut into 5 $\mu$m sections. The sections were counterstained with 0.1% nuclear fast red. The adjacent tissue sections were also stained for nonspecific esterase activity, which appears brown-black. Blue colored cells were identified by light microscopy.

Cytochemical Identification Of Macrophages: Cells and tissue sections were stained nonspecific esterase activity, which is relatively specific for mononuclear phagocytes. The cell smears were fixed as described above, and incubated with a filtered solution containing a-naphthyl acetate and Fast Blue BB salt for 10 minutes at room temperature. Tissue sections were stained with this solution for 1–3 hours, and counterstained with 0.1% nuclear fast red.

Immunocytochemical Staining For $\beta$-Galactosidase: The expression of the transgene in cells isolated from tissues (spleen and bone marrow) transfected in vivo with the plasmid pCMVZ was determined by indirect immunofluorescence. Cell smears were fixed with methanol/acetone for 2 minutes at room temperature, and the cells were incubated with a rabbit anti-$\beta$-galactosidase polyclonal antibody for one hour at 37° C. The primary antibody was diluted 1:100 in PBS for immunodetection in the fixed cell smears. Fluorescein isothiocyanate conjugated anti-rabbit immunoglobulin G diluted 1:100 in PBS was used as the secondary antibody. The cells were also counterstained with propidium iodide, which produces red fluorescence in the cell nucleus. Between each incubation, the cells were washed three times for five minutes with PBS. The stained cells were examined by fluorescent microscopy.

Assays For Luciferase Activity: Cells in culture were harvested, lysed, and analyzed for luciferase activity as described previously. Tissues were harvested from transfected and control rats after the animals were sacrificed and perfused in situ with 50 milliliters of cold PBS, pH 7.5. The tissues were homogenized in lysis buffer and permitted to incubate at 22° C. for 10 minutes. The cell lysates were subsequently centrifuged for 5 minutes at 4° C. , and the protein extracts were analyzed for luciferase activity. The lysates were assayed for protein content and the measured integrated light units were standardized for total protein content. All measurements were performed in triplicate and expressed as an average of the values.

Statistical Analysis: Data are expressed as means±standard error of the mean (SEM), and evaluated by an analysis of variance using the Student-Newman-Keuls (SNK) test.

Results

In vitro Transfection Of Primary Macrophages Using The Mannose-Terminal Glycoprotein Carrier: Using an expression plasmid (pCMVZ) encoding the *E. coli* lacZ gene as a reporter gene, complexes of the plasmid and the mannose-terminal 5 glycoprotein carrier were applied to cells peritoneal exudates cells isolated from mice. Twenty-four hours after transfection, the cells were examined for $\beta$-galactosidase activity. The number of transfected cells varied from 5 to 26 per cent of all cells examined. In addition, the proportion of cells with non-specific esterase activity, a cytochemical marker characteristic of monocytes and macrophages, that expressed the transgene ranged from 40% to 75%. Transfections using complexes consisting of an irrelevant plasmid (pGEMluc ) bound to the carrier or the expression plasmid (pCMVZ) bound to a galactose-terminal glycoprotein carrier no significant β-galactosidase activity in the exudate cells. Faint blue staining was noted in these control cells, which was most likely due to endogenous β-galactosidase activity. Nevertheless, the percentage and intensity of blue stained cells in the controls was markedly less than that in the transfected dishes, The mannose-terminal glycoprotein carrier-DNA complex appeared to be non-toxic to cells since the percentage of cells viable, based on cell counts and trypan blue staining, after treatment was not significantly different than controls.

Complexes of the mannose-terminal glycoprotein carrier and the expression plasmid pGEMluc were applied to cells isolated from peritoneal exudates for increasing periods of time, and luciferase activity was measured in protein extracts of the transfected cells 24 hours following transfection. As noted in the previous experiments, the level of expression of the transferred gene varied. An eight-fold increase in relative luciferase activity in transfected cells was present ($p<0.01$), whereas protein extracts obtained from cells treated with a complexes formed using a galactose-terminal glycoprotein carrier did not express activity significantly different than the non-transfected control. Furthermore, the addition of a one hundred-fold molar excess of mannosylated bovine serum albumin over complex to the culture media immediately before transfection, which should compete with the carrier for the mannose receptor, completely inhibited the uptake and expression of the reporter gene ($p<0.01$). The duration of the transgene expression in these cells was also examined. The complexes of the mannose-terminal glycoprotein carrier and the expression plasmid pGEMluc were applied to cells for 24 hours, and protein extracts were assayed for luciferase activity at several timepoints after transfection. Optimal transgene expression was detected one day after treatment, and luciferase activity decreased to control levels eight days post transfection.

In vivo Transfection Of Macrophages Using The Mannose-Terminal Glycoprotein Carrier: The mannose-terminal glycoprotein carrier was used to transfer reporter genes into the spleen and livers of intact animals. Rats were anesthetized, and 300 µg of plasmid (pGEMluc) was complexed to the mannose-terminal glycoprotein carrier and infused slowly into the caudal vena cava over several minutes. Control and mock transfections of animals using complexes consisting of an irrelevant plasmid (pCMVlacZ) bound to the carrier were also performed in parallel. All animals injected with the complex survived. Luciferase assays were performed four days after infusion of the complexes in tissue homogenates extracted from liver, lungs, and spleen. We observed significant levels of transgene expression in the protein extracts from the spleen obtained from transfected animals. Lower levels of luciferase activity was found in the liver and lung. Non-transfected rats and animals treated with the complexes consisting of an irrelevant plasmid (pCMVlacZ) bound to the mannose-terminal glycoprotein carrier had no significant luciferase activity in protein extracts from any tissue. Twelve days after transfection, luciferase activity approximated background levels in all tissues examined.

The cellular distribution of the transgene expression was examined in sections of spleen and liver three days after the injection of complexes containing pCMVlacZ. The tissues were analyzed for β-galactosidase activity by a cytochemical stain. An animal treated with complexes made using an irrelevant plasmid (pCMVIL2r) served as control. β-galactosidase expression was detected in several small cells in the spleen located in the subcapsular region, which conformed to the distribution of cells that expressed non-specific esterase activity based on cytochemical staining. No β-galactosidase activity was found in the corresponding cells of the control spleen. Rare, blue-stained cells were present in hepatic sections of the transfected animal, and no hepatic endothelial cells, which also have surface mannose receptors, expressed the transgene. Nucleated cells were also isolated from the spleen and stained in vitro. Furthermore, cells extracted from the bone marrow and bronchoalveolar lavage fluid of the transfected and control animals were also treated with a solution containing X-gal and examined for β-galactosidase activity. Approximately 10–20 percent of the nucleated cells obtained from the spleen stained blue. Rare cells from the mock transfected animal were also faintly blue stained, most likely due to an endogenous β-galactosidase. Nevertheless, the percentage and intensity of blue stained cells in the controls was significantly less than that found in the control animal.

A polyclonal antibody directed against the bacterial β-galactosidase was used for the immunocytochemical localization of the transgene product to establish that the blue-stained cells in the spleen are not due to endogenous β-galactosidase or the nonspecific hydrolysis of X-gal. Nucleated cells isolated from the spleen and bone marrow of the animals described above were stained with antibody directed against β-galactosidase and fluorescein isothiocyanate conjugated anti-rabbit and examined for immunofluorescence. A number of the isolated cells, which were morphologically similar to the blue stained cells demonstrated in the cytochemical assay, had immunofluorescent staining. In addition, these cells had nonspecific esterase activity.

Discussion

We have developed a synthetic glycoprotein complex capable of mediating transfer of functional genes into macrophages in culture and the livers of whole animals. Expression plasmids non-covalently bound to an mannose-terminal glycoprotein carrier can be introduced efficiently into cells that express the mannose receptor. The delivery of DNA by a receptor-mediated gene transfer system is dependent on the presence of receptors on the surface of the targeted cell. Cells that fail to express the asialoglycoprotein receptor were not transfected by this system. In addition to macrophages, other cell types present in the peritoneal exudate that fail to express the mannose receptor, i.e., granulocytes, lymphocytes and fibroblasts, were not transfected. The expression of the reporter gene was localized to cells that had either non-specific esterase or peroxidase activity, reliable cytochemical markers used for macrophage identification.

The specificity and affinity of the ligand for the specific receptor are of considerable importance for the delivery of exogenous genes. Macrophages bind mannose-terminal glycoproteins with high affinity and specificity. The mannose-terminal glycoprotein carrier successfully introduced reporter genes into macrophages in culture and in intact animals, whereas transgene expression was not detected in cells transfected using a galactose-terminal glycoprotein carrier. Uptake does not appear to be due to a non-specific increase in pinocytosis or phagocytosis secondary to the presence glycoprotein in the culture medium. The delivery and expression of the plasmid is inhibited by the addition of mannosylated bovine serum albumin to the culture medium, which presumably competes for the binding site(s) on the mannose receptor. Finally, the substitution of an alternative monosaccharide for mannose could increase the affinity of the DNA-carrier complex, since the mannose receptor also recognizes glycoproteins with glucose, fucose, and N-acetylglucosamine residues in exposed positions. In addition, gene transfer efficiency could potentially be improved by altering the carbohydrate residue to an oligosaccharide, i.e., oligomannose, since monosaccharides are poorer ligands for the receptor than are polyvalent glycoproteins.

A major factor in determining the level of expression of the genes transferred into target cells involves the survival and delivery of the exogenous DNA to the nucleus. Expression of genes introduced by receptor-mediated mechanisms may be limited by the trapping and degradation of the complex in endosomal compartments. Mannose-terminal glycoproteins are introduced into macrophages by receptor-mediated endocytosis, delivered to a pre-lysosomal acidic compartment, and subsequently trafficked to the secondary lysosomes. Apparently, a portion of the introduced conjugate avoids destruction since the transferred DNA must escape degradation after the complex has entered the cell in order for the transgene to be expressed. The physical state of the DNA transferred into cells by these delivery systems may also contribute to its survival and subsequent expression, and highly compact form of DNA may be more resistant to nuclease digestion. Furthermore, the small size of the carrier-DNA complex may also permit the introduction of the plasmid into the cells of the reticuloendothelial system specifically via the mannose receptor and not by phagocytosis.

This study illustrates the potential of specifically directing gene transfer into macrophages by targeting the mannose receptor, and theoretically could provide an approach to the treatment of various inborn errors of metabolism, like Gaucher disease. Pharmacologic therapies that also target the mannose receptor have been shown to be effective in patients with Gaucher disease. Repeated treatments of affected individuals with modified human glucocerebrosidase, in which the outer carbohydrate moieties are cleaved to expose terminal mannose residues, have had substantial clinical improvement in their disease, as demonstrated by reduction in hepatosplenomegaly and resolution of anemia. Unfortunately, the cost of this therapy has been prohibitive to many patients. Bone marrow transplantation has been shown to be curative in the non-neuropathic form of the disease, yet the potential complications of transplantation precludes this procedure in many patients, particularly those in individuals with mild disease. However, because Gaucher disease can be corrected by bone marrow transplantation, one potential approach that has been proposed for the gene therapy of Gaucher disease involves the ex vivo transfer of the normal glucocerebrosidase gene into autologous hematopoietic stem cells and their subsequent introduction into the patient. Alternatively, lymphoblasts could be harvested from the affected individual, infected with replication-incompetent, recombinant retrovirus containing the wild-type gene, and returned to the patient. The secreted enzyme would enter the macrophages via the mannose receptor, thus becoming the secondary targets of therapy. In the system we describe in this manuscript, the macrophage would be the primary target for genetic correction. Practical questions regarding the efficiency of gene delivery, duration and level of expression achieved using this technique, and the immunologic properties of the DNA-carrier complexes need to be addressed. Nevertheless, receptor-mediated gene therapy has the potential of providing a non-invasive approach to the treatment of such diseases.

EXAMPLE 3

We have also used a Fab fragment of an antibody directed against the rat polymeric immunoglobulin receptor that is expressed in the airway epithelia. The Fab peptide was covalently coupled to poly-L-lysine and complexed to an SV40-luciferase expression vector using the procedure described below. Rats injected with the DNA complex had luciferase activity for as long as 8 days (the duration of the experiment) only in tissues that expressed the receptor. These finding underline the flexibility of this system for delivering DNA to specific tissues of an adult animal.

Introduction

Several methods of gene transfer into the respiratory tract have been developed that permits the introduction of functional genes into cells in vivo. However, many of these approaches have lacked specificity and are cytotoxic. Replication deficient, recombinant adenoviruses have been used to deliver the reporter genes to respiratory epithelial cells in a variety of animal models. However, the physiologic effects of treatment with adenovirus are not well understood, and recent evidence suggests that the first-generation adenoviral vectors administered at high viral titers to animals produce a substantial inflammatory response in the lung. Liposomes have also been used to transfer functional genes to the airway epithelium, but this approach has generally been toxic to cells and lack specificity.

Receptor-mediated gene transfer may provide a method for delivering DNA to specific target cells using a non-infectious, non-toxic vector. This form of gene transfer allows specific tissue targeting with DNA plasmids of considerable size, allowing for delivery of not only the transgene, but also promoter and enhancer elements. In the case of receptor-mediated systems, the delivery of exogenous DNA is dependent on the stability of the DNA-carrier complex, the presence and number of specific receptors on the surface of the targeted cell, the receptor-ligand affinity and interaction, and efficient internalization of the complex. Furthermore, expression of the transferred genes rely on their escape from the endosomal vesicles and trafficking to the target cell's nucleus. The duration of transgene expression in whole animals delivered by exploiting receptor-mediated endocytosis has been generally been transient, returning to background levels within seventy-two hours after treatment. This has been the case for reporter genes introduced into airway epithelial cells via the intratracheal route using adenovirus-polylysine and transferrin-adenovirus-polylysine vectors.

We have demonstrated that in primary cultures of human tracheal epithelial cells, targeting the polymeric immunoglobulin receptor (pIgR) permits the efficient delivery of the transgene specifically to cells that bear the receptor. The polymeric immunoglobulin receptor is expressed only in mucosal epithelial cells, including airway epithelial and submucosal gland cells, and is specifically adapted for the internalization and nondegradative transfer of large molecules. In this report, we show that targeting the polymeric immunoglobulin receptor in vivo results in expression of the transgene in tissues that contain receptor-bearing cells which was maximal six days after transfection.

Methodology

Materials: DNA-modifying enzymes, nucleotides, and 5-Bromo-4-chloro-3-indolyl-β-D-galactopyranoside were purchased from Boehringer Mannheim (Indianapolis, Ind., USA). Luciferase assay system was obtained from Promega (Madison, Wis., USA). Protein A MAPS agarose columns were purchased from BioRad (Richmond, Calif., USA). Papain and poly (L-lysine) were obtained from Sigma Chemical Company (St. Louis, Mo., USA), and N-Succinimidyl-3-(2-pyridyldithio)proprionate was from Pierce Chemical Company (Rockford, Ill., USA). The mouse monoclonal anti-human interleukin 2 receptor antibody was obtained from Dako Corporation. (Carpenteria, Calif., USA), and the fluorescein isothiocyanate-labelled secondary goat anti-mouse antibody was from Sigma Immunochemicals (St. Louis, Mo., USA). The Vectastain ABC method, used in the immunoperoxidase staining procedure, was purchased from Vector Laboratories (Burlingame, Calif., USA). All media, sera, and antibiotics were obtained from Gibco Laboratories (Grand Island, N.Y., USA).

Preparation Of Fab Fragments: The isolation and papain digestion of antibodies derived from rabbits immunized with rat secretory component has been described previously. Briefly, polyclonal antibody was isolated from rabbit serum using a Protein A MAPS agarose column as described by the manufacturer. Isolated immunoglobulin G (2 mg) was treated with 20 $\mu$g papain for 12 hours at 37° C. in the presence of 100 mM sodium acetate (pH 5.5) 50 mM cysteine, and 1 mM EDTA. The Fab fragment was separated from intact antibody and Fc fragments by Protein A chromatography. An irrelevant Fab (IFab) was generated by papain digestion of IgG from pre-immune rabbit serum.

Preparation Of Fab-Polylysine Conjugates: The Fab fragment of the anti-pIgR immunoglobulin G was covalently linked to poly (L-lysine) ($M_r$ 10,000 Da) using the heterobifunctional crosslinking reagent N-Succinimidyl 3-(2-pyridyldithio) proprionate (SPDP). The Fab fragment was incubated with a seventy-five fold molar excess of SPDP in 0.1M phosphate buffered saline (PBS), pH 7.5, at 22° C. for 60 minutes. After introduction of 2-pyridyl disulfide structures onto the Fab fragment, unreacted SPDP and low molecular weight reaction products were removed by dialysis. The disulfide bridges of the modified Fab fragment were cleaved with 25 mM dithiothreitol. Both the poly (L-lysine) and SPDP was added in fifteen fold molar excess to the modified Fab fragment, and the reaction was carried out at 22° C. for 24 hours. The conjugate was dialyzed to remove low molecular weight reaction products, and analyzed by separating the resultant proteins on a 0.1% SDS-7.5% polyacrylamide gel electrophoresis. As described previously, analysis of the conjugate demonstrated a protein that migrated slowly, corresponding to a protein greater than 200 kDa in size.

Reporter Genes And Plasmid Preparation: The expression plasmid pGEMluc contained the SV40 viral promoter ligated to the *P. pyralis* luciferase gene. The plasmids pCMVZ and pCMVIL2r, consisting of the cytomegalovirus (CMV) promoter linked to the *E. coli* lacZ and the interleukin 2 receptor genes, respectively, were also used as reporter genes. For studies of luciferase activity, these plasmids were employed as irrelevant DNA (IDNA) controls. The plasmids were grown in *E. coli* DH5a, extracted, and purified by standard techniques. Digestions of the plasmids with restriction endonucleases yielded the appropriate size fragments, and purity was established by 1.0% agarose gel electrophoresis. The sizes of plasmids are as follows: pGEMluc, 6.0; pCMVlacZ, 10.9; and pCMVIL2r, 5.4 kB. No contamination with bacterial genomic DNA or RNA was present in the plasmid preparations.

Preparation Of Fab-Polylysine-DNA Complexes: The carrier-DNA complexes were formed using a method described previously.

Animals: The anti-rat secretory component Fab antibody-polylysine carrier was used to transfer reporter genes into the airways and livers of intact animals. Adult, male Sprague-Dawley rats, weighing approximately 250 g., were anesthetized. Using aseptic technique, 0.3 to 0.6 ml of a solution containing 300 $\mu$g of an expression plasmid complexed to the carrier was injected into the caudal vena cava. The rats were sacrificed at several different times after infusion of the complexes and various organs were removed for analysis. Mock transfections of animals using complexes consisting of an irrelevant plasmid bound to the carrier or the expression plasmid bound to a carrier made with an irrelevant Fab fragment were also performed in parallel. The animal research protocol was reviewed and approved by the Case Western Reserve University Institutional Animal Care Committee.

Cytochemical Assay For $\beta$-Galactosidase Activity: Individual cells expressing $\beta$-galactosidase in tissues were identified following incubation with 5-Bromo-4-chloro-3-indolyl-$\beta$-galactopyranoside (X-gal) as described previously. Briefly, the cells were fixed with a solution of 0.5% glutaraldehyde in PBS for 10 minutes, washed twice with PBS, pH 7.5, and then incubated with a solution containing 0.5% X-gal, 5 mM Potassium ferricyanate, 5 mM Potassium ferrocyanate, and 1 mM Magnesium chloride in phosphate-buffered saline (pH 7.4) for 4 hours at 37° C. The stained tissues were fixed in 2% paraformaldehyde/0.5% glutaraldehyde in PBS overnight at 4° C., paraffin embedded by standard procedure, and cut into 5 $\mu$m sections. The sections were counterstained with nuclear fast red. Blue colored cells were identified by light microscopy. A minimum of 100 cells were counted to determine the percentage of cells per section that express $\beta$-galactosidase. In addition, adjacent sections were stained with Alcian blue/periodic acid Schiff or haematoxylon/eosin using standard protocols.

Assays For Luciferase Activity: Cells in culture were harvested, lysed, and analyzed for luciferase activity as described previously. Tissues were harvested from transfected and control rats after the animals were sacrificed and perfused in situ with cold PBS, pH 7.5, for five minutes. The tissues were homogenized in lysis buffer and permitted to incubate at 22° C. for 10 minutes. The cell lysates were subsequently centrifuged for 5 minutes at 4° C., and the protein extracts were analyzed for luciferase activity. The lysates were assayed for protein content and the measured integrated light units (10 second interval) were standardized for total protein content. All measurements were performed in triplicate and expressed as an average of the values.

Immunohistochemical Staining For The Interleukin 2 Receptor: The expression of the transgene in tissues transfected with the plasmid pCMVZ was determined by indirect immunofluorescence. Frozen sections of various tissues were fixed with acetone for 10 minutes at −20° C., and treated with for ten minutes at 22° C. to reduce autofluorescence. The sections were then incubated with 10% goat serum in PBS, pH 7.5, for one hour at room temperature. The cells were incubated sequentially with a mouse monoclonal anti-interleukin 2 receptor antibody and fluorescein isothiocyanate-conjugated goat anti-mouse IgG. Both antibodies were diluted 1:100 in PBS, and between each incubation, the cells were washed three times for five minutes with PBS, pH 7.5. The stained cells were examined by fluorescent microscopy.

Results

In vivo Transfection Using The Anti-Secretory Component Fab Antibody-Polylysine Carrier: All animals injected with the anti-rat secretory component Fab antibody-polylysine carrier-DNA complex survived. Luciferase assays were performed 48 hours after infusion of the complexes in tissue homogenates extracted from liver, lungs, spleen, and heart. We observed significant levels of transgene expression in the protein extracts from the liver and lungs obtained from transfected animals. No detectable luciferase activity was found in the spleen and heart, tissues that do not express the pIgR. Furthermore, animals treated with the complexes consisting of an irrelevant plasmid (pCMVlacZ) bound to the carrier or the expression plasmid (pGEMluc) bound to a carrier based on an irrelevant Fab fragment resulted in no significant luciferase activity in any tissue examined. Thus, only tissues that contain cells bearing pIgR are transfected, and transfection cannot be attributed to the nonspecific uptake of an irrelevant Fab antibody-based complex.

A time course of the expression of the transferred gene, in which luciferase activity in protein extracts derived from the four tissues was measured at different timepoints after injection of the complex, was developed. Luciferase activity persisted in the liver and lung, tissues which have pIgR, achieving maximum values of 13795±4431 and 461402±230078 integrated light units (ILU) per milligram of protein extract, respectively, at four to six days after injection. Tissues that failed to express the receptor did not have significant transgene expression.

The cellular distribution of the transgene expression was examined in sections of various tissues. Three days after the injection of complexes containing pCMVlacZ, tissue sections of trachea, lung, and liver underwent cytochemical staining for β-galactosidase activity. An animal treated with complexes made using an irrelevant plasmid (pCMVIL2r) served as control. Expression in the trachea was limited to the cells lining the epithelial surface. No β-galactosidase activity was detected in the tracheal sections from the mock transfected animal. The expression of the transgene was variable, and in some areas of the respiratory epithelium greater than 50% of the cells stained blue. In general, expression ranged from 10–20% of the tracheal epithelial cells. Both ciliated and secretory (goblet) respiratory epithelial cells expressed β-galactosidase activity, based on Alcian blue/periodic acid Schiff staining of adjacent sections of the airway. No expression from the transgene was detected in the terminal airways or alveoli in either the transfected or control animal (data not shown). This conforms to the distribution of epithelial cells that express the pIgR based on in situ immunohistochemical staining. Rare submucosal glands were evident in the tracheal sections, and only faint blue staining was noted. No inflammatory response was found in any of the tracheal sections from the non-, mock-, and transfected animals. In addition, a mouse monoclonal antibody directed against the human interleukin 2 receptor, a surface protein that has been used as a reporter in the transduction of respiratory epithelial cells in vitro but is not naturally expressed in these cells, was used for immunofluorescent localization of the transgene product in the trachea of the animal transfected with the plasmid pCMVIL2r. Serial sections of the trachea were examined for the presence of fluorescence, and the apical membrane of numerous respiratory epithelial cells from the transfected animal stained appropriately. No specific fluorescent staining was detected in the airway epithelia of an animal mock-transfected with pCMVlacZ. Rare, blue-stained hepatocytes were also found in hepatic sections of the transfected animal. Transgene expression was not identified in the livers from either non- or mock-transfected rats.

Discussion

We report the successful transfer of reporter genes into the airway epithelium in vivo following the injection of a targeting complex consisting of the Fab portion of immunoglobulin G directed against the rat polymeric immunoglobulin receptor conjugated to poly (L-lysine), and noncovalently bound to plasmid DNA. This technique specifically delivered the transgene to the liver and lung, tissues in which this receptor is expressed. Other tissues that do not express the receptor, like the spleen and heart, were not transfected. In addition, following injection of a conjugate prepared with irrelevant Fab fragments no expression was detected, and a complex prepared with a plasmid containing an irrelevant reporter gene also failed to produce detectable luciferase activity. Thus, this complex specifically targets receptor-bearing tissues and the normal trafficking of the receptor's natural ligands does not interfere with the uptake of the transgene in vivo.

Most of the strategies for gene transfer into the respiratory tract currently available depend on viral vectors which do not specifically target respiratory epithelial cells, and rely upon the intratracheal route of delivery to permit targeting of the airway. Intratracheal instillation has also been used to specifically direct gene transfer by other means, like liposomes and adenovirus-transferrin-polylysine conjugates, to the airway epithelium. Systemic delivery of DNA bound to cationic liposomes has not been selective and transfers functional genes to a number of cell types in different tissues. The specificity of receptor-mediated gene transfer for cells that bear the pIgR may be useful in targeting defective cells in the airways of patients with cystic fibrosis.

EXAMPLE 4

Familial hypercholesterolemia (FH) is a human genetic disease characterized by fulminant atherosclerosis and cardiovascular disease. A mutation in the gene for the receptor that mediates the uptake of the low density lipoprotein (LDL) is responsible for this disease. One in every 500 people is heterozygote for a mutation in the LDL receptor gene that is responsible for FH. As a result, LDL is removed from their plasma at only two thirds the normal rate. In the fourth to fifth decade of life, the elevated levels of LDL in plasma cause symptomatic atherosclerosis in these patients. FH-homozygotes (one in a million people) have little or no functional LDL receptor, depending on the domain of the protein that is affected by the mutation. This results in symptomatic coronary atherosclerosis before the age of 20. Treatment with bile acid-binding resins and inhibitors of cholesterol synthesis has been considerably successful in heterozygous FH patients by stimulating the production of LDL receptor from the single normal gene. In FH homozygotes there is no response to drug therapy. Because of the absence of a normal gene that can be stimulated, the replacement of the mutated gene is the only possible approach for the treatment of homozygous FH patients. Since the liver is the major organ responsible for LDL catabolism, the two approaches taken for the treatment of the disease target this organ: liver transplantation and gene therapy. Transplantation of a normal liver into a patient with FH can correct hyperlipidemia, suggesting that reconstitution of the hepatic LDL receptor should be sufficient for phenotypic improvement. Based on this results, all the approaches undertaken using gene therapy for the treatment of FH have targeted the hepatocytes.

In order to understand the mechanism of disease, it is necessary to be aware of the metabolism/fate of cholesterol in the organism. Every cell needs cholesterol for the synthesis of the plasma membrane. The adrenal glands and the corpus luteum in the ovary, in addition, require cholesterol for the synthesis of steroid hormones. The liver is the organ with the highest demand because of the production of bile acids. Cholesterol is obtained in peripheral tissues either from receptor-mediated uptake of low density lipoproteins (LDL), which are the main carriers of endogenous cholesterol in the blood, or by biosynthesis. HMG CoA reductase is the rate-determining enzyme in the pathway. Dietary cholesterol is carried in the bloodstream by chylomicron particles, which are taken up by specific receptors in the liver. In order to provide the different tissues with cholesterol, the liver secretes very low density lipoprotein (VLDL) particles composed of triglycerides, cholesteryl esters and apoproteins C, E and B-100. The uptake of triglycerides from VLDL by adipose tissue and muscle converts these particles into intermediate density lipoproteins (IDL). The LDL receptor, present at highest concentration in the liver and adrenal glands but also in the rest of tissues, recognizes the apo E and apo B-100 components of IDL. Thus, under normal conditions IDL is mostly cleared from the bloodstream by LDL receptor-mediated uptake. The remaining IDL is converted to LDL, which is taken up as well by the LDL receptor that recognizes the apo B-100 component. The clearance of cholesterol from the organism is carried out by the liver, where it is converted to bile acids and secreted into the digestive tract. Although most of the cholesterol is reabsorbed in the terminal ileum for liver reutilization, this pathway provides the route of exit.

Thus, the presence of non-functional LDL receptors that are unable to clear IDL and LDL from the blood results in elevated serum LDL levels, and therefore total serum cholesterol. This is responsible for cholesterol deposition in the artery walls and thus, atherosclerosis.

The Watanabe Heritable Hyperlipidemic (WHHL) rabbit has been previously used to study the effectiveness of gene therapy techniques in correcting hypercholesterolemia. A 12 nucleotide in-frame deletion in the ligand-binding domain of the LDL receptor, similar to one class of mutation found in FH patients, results in symptoms, evolution and histopathology that parallel those of FH.

Materials And Methods
Construction Of The DNA Plasmids

The plasmid DNAs used in this work are pLDLR-17, PCK-hLDLR, PCK-rLDLR and SV40-luciferase. pLDLR-17 was provided by Dr. David Russell (University of Texas, Medical Center, Dallas) and consists of the cytomegalovirus (CMV) promoter/enhancer linked to the human LDL receptor cDNA. It contains a fragment of DNA corresponding to the 5' untranslated region (UTR) of the Alfalfa Mosaic Virus 4 (AMV4) RNA linked to the human LDL receptor cDNA. This sequence acts as a translational enhancer by decreasing the requirements for initiation factors in protein synthesis. The PCK-hLDLR plasmid has been constructed by subcloning the hLDL receptor cDNA from the pLDLR-17 into a pTZ18R vector (Pharmacia) containing the phosphoenolpyruvate carboxykinase (PEPCK) promoter (−460 to +73) and an intron and polyadenylation signal from the simian virus 40 (SV40) small T antigen. In a two step process, the hLDL receptor cDNA was excised with SacI and SmaI from the pLDLR-17 and blunted using T4 DNA polymerase. The blunted fragment was subcloned into the HincII site of a pTZ18R vector. The cDNA was then excised with XbaI and SalI and introduced into the homologous sites of the pTZ18R-PEPCK promoter-SV40 polyA plasmid. For the construction of pPCK-rLDLR, the EcoRI-EcoRI fragment from prLDLR-9 (provided by Dr. James Wilson, University of Pennsylvania) containing the rabbit LDL receptor cDNA was subcloned into the EcoRI site of a pBluescript (Stratagene). This construct was digested with SacI and blunted and then digested with XbaI, and directionally subcloned into the XbaI-blunted HindIII sites of a pTZ18R vector containing the PEPCK promoter (−460 to +73) and an intron and polyadenylation signal from SV40 small T antigen. The SV40-luciferase plasmid (Promega) contains the SV40 viral promoter and enhancer ligated to the P. pyralis luciferase gene inserted into the pUC19 vector (Pharmacia).

Formation Of The poly-L-lysine-DNA Complex

Production Of The Galactosylated poly-L-Lysine: Poly-L-lysine was galactosylated as described (PNAS). Two mg of poly-L-lysine-HBr (Sigma P-7890, average chain length, 100) was reacted with 85 mg of a-D-galactopyranosyl phenylisothiocyanate (Sigma G-3266). The solution was adjusted to pH 9 by the addition of 1/10 volume of 1M sodium carbonate pH 9. The tube was shielded from light by aluminum foil and mixed for 16 hours at room temperature, then dialyzed using Spectra-Por dialysis tubing (3500 M.W. cutoff) against 500 ml of 5 mM NaCl for 2 days with frequent changes of buffer (4 changes/day). The reaction is stoichiometric and resulted in the galactosylation of 0.8 to 1% of the $NH_3$ groups present in the solution.

Basic Protocol For The Condensation Of DNA: Plasmid DNA was prepared using standard techniques. The DNA was resuspended in 10 mM Tris-HCl, pH 8.0, containing 1 mM EDTA and the concentration of the DNA determined spectrophotometrically. The DNA preparation was treated twice with RNAse A+T1. This step ensures that RNA is not present in the solution (RNA inhibits the condensation of DNA by poly-L-lysine). A solution containing a high concentration of DNA (1.5–2 mg/ml) was used in further steps. An example of a typical protocol for DNA condensation is described as follows:

a) 300 mg of DNA in 200 ml of 0.75M NaCl (added from 5M NaCl solution) is vortexed at medium speed, using a VIBRAX apparatus (IKA-VIBRAX-VXR). This step is necessary to increase the effective length of the DNA polymer in high salt solutions, thus achieving efficient binding of the poly-L-lysine moiety to the DNA backbone.

b) 120 mg of poly-L-lysine or galactosylated poly-L-lysine (average chain length 100) in 200 ml of 0.75M NaCl (added from a 5M NaCl solution) is added dropwise over a period of 30 minutes to 1 hour in 5 μl aliquots. This amount translates into a molar ratio of 1 DNA $PO_4$ group to 1 carrier $NH_3^+$ group.

c) The solution becomes turbid at the end of the process. Three μl aliquots of 5M NaCl are added dropwise to the vortexing solution until turbidity disappears as monitored by eye. This process is slow, allowing 60 seconds between the addition of each new aliquot of 5M NaCl. Then the solution is subjected to circular dichroism (CD) spectroscopic monitoring. The solutions of DNA/poly-L-lysine complexes were also analyzed using a JEOL-100C electron microscope. The condensation process is complete when the diagnostic spectrum of the DNA complex is observed and is further established by EM. For subsequent preparations of DNA complex consisting in the same plasmid DNA at the same concentration of nucleotide, the protocol can be followed without monitoring with CD. When using different concentration of DNA or a different plasmid the CD monitoring should be repeated.

Animals

Six adult male Watanabe rabbits (2.8–3.2 Kg of bodyweight) were used in these studies. These animals have been purchased from an established colony at the National Institutes of Health. In order to introduce the DNA complex into the animal, we perform a single injection of 3–10 ml of the DNA-complex solution (~400–900 mM NaCl) into the marginal ear vein of the rabbit. Approximately 1.5 ml of blood was drawn from the ear artery at 4 p.m. The determination of the concentration of serum cholesterol was performed in the Clinical Laboratory of University Hospitals of Cleveland from 300 µl of serum. At different time points following the introduction of the DNA complex, a rabbit was subjected to a liver biopsy. Total DNA was isolated from the hepatic sample and subjected to PCR amplification in order to detect the presence of the transferred DNA. Rabbit #774 was treated with lovastatin (Mevacor, Merck and Dohme) orally at a dose of 10 mg per day.

Polymerase Chain Reaction (PCR) Amplification

In order to detect the presence of the transferred DNA in the liver of the treated animal, total DNA was isolated from the hepatic sample obtained upon biopsy. In the case of rabbit #737, the DNA of interest was then amplified by PCR using an upstream primer corresponding to positions 32–50 in exon 1 of the 5' UTR of the PEPCK gene and a downstream primer complementary to nucleotides 589–607 of the human LDL receptor cDNA. The amplified fragment corresponds to a 1100 bp band upon hybridization with a 700 bp fragment corresponding to the 5' end of the human LDL receptor cDNA labeled with 32P-dCTP. Appropriate primers corresponding to the chimeric CMV-hLDL receptor gene will be used for the PCR amplification of the transferred plasmid from liver tissue obtained from rabbit #774.

ELISA

Aliquots of 75 µl corresponding to 1 µg of DNA of either newly prepared galactosylated-poly-L-lysine/DNA complex, plasmid DNA or galactosylated-poly-L-lysine were incubated overnight at 4° C. to coat each well of a 96 well microtiter plate. The next day the wells were washed 3 times with phosphate-buffered saline (PBS), then blocked for 2 hours at 37° C. with 5% bovine serum albumin (BSA) in PBS and washed 3 times with the washing buffer containing 1% BSA and 0.5% Tween-20 in PBS. Seventy-five µl of serum from rabbit #774 obtained at different time points before and after the repeated administration of the DNA complex at dilutions of 1:3 and 1:30 were added to the wells and incubated for 90 minutes at 37° C. The wells were then washed with washing buffer and incubated with the secondary antibody at 1:3000 dilution. The secondary antibody consists of a mouse monoclonal antibody against rabbit immunoglobulins conjugated to alkaline phosphatase (Sigma). After a final wash with washing buffer, the pNPP substrate at 1 mg/ml in glycine buffer was added to the wells to develop the reaction and spectrophotometric readings at 410 nm were taken in a Dynatech automated ELISA reader. Values taken at 120 minutes were chosen for comparison.

Results

1. Rabbit #676: injection of the poly-L-lysine/DNA complex containing 3 mg of the chimeric PCK-hLDLR gene.

In a first set of experiments, we condensed 3 mg and 9 mg of pPCK-hLDLR with galactosylated poly-L-lysine using the technique developed in our laboratory and we injected them into the peripheral circulation of Watanabe rabbits.

The promoter from the gene for the cytosolic form of the phosphoenolpyruvate carboxykinase (PEPCK) from the rat has been characterized in detail. This promoter was used in these experiments because it is expressed at a high level in the liver and its expression can be controlled by diet and hormones. Starvation and a high protein, carbohydrate-free diet stimulate PEPCK gene transcription while a high carbohydrate diet reduces transcription from the PEPCK promoter. In addition, cAMP and glucocorticoids induce, and insulin inhibits, expression of the PEPCK gene in the liver. The PEPCK promoter is thus suitable for the regulation of a linked structural gene introduced into the liver and was used in our first experiments for the hepatic expression of LDL receptor.

Figure 13:
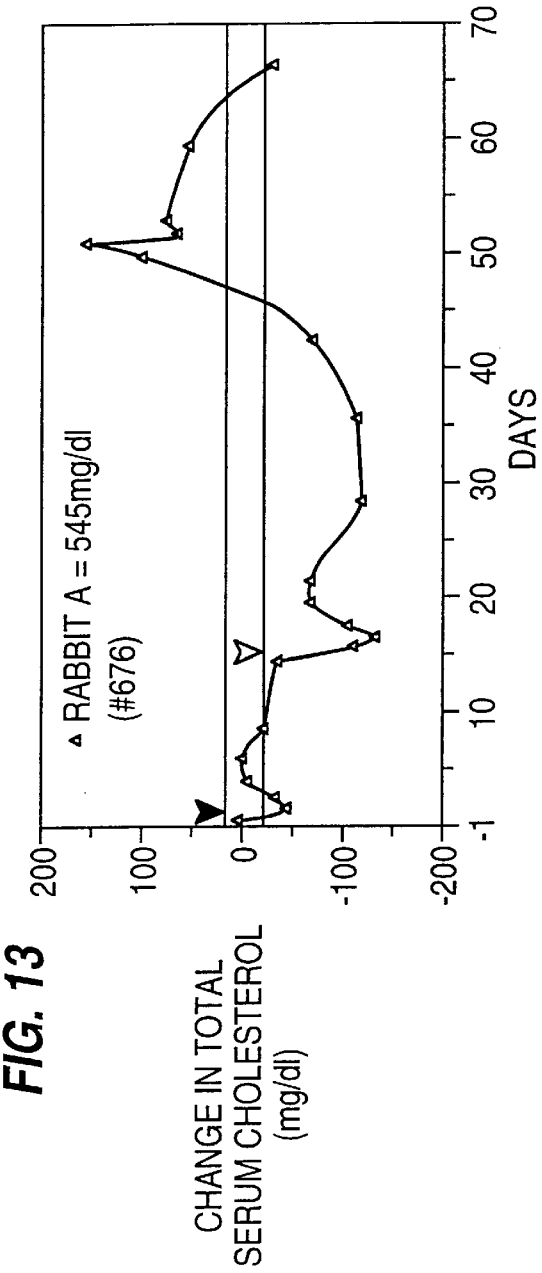

In our first approach we have injected the poly-L-lysine/DNA complex containing 3 mg of DNA. This basic dose of DNA was decided based on previous experiments performed in rats. As shown in FIG. 13, the administration of a DNA complex solution containing 3 mg of the pPCK-hLDLR plasmid in a relaxed state to rabbit #676 did not result in a significant decrease in total serum cholesterol levels. A second injection of DNA complexes appropriately condensed containing 3 mg of the same DNA caused a 20% reduction of the levels of cholesterol in the blood. Four weeks after this second administration, cholesterol returned to approximately pretreatment levels, reaching a peak at about 35 days.

A 20% decrease in total serum cholesterol levels resulting from the expression of the PCK-hLDL receptor gene will likely be helpful but will not totally alleviate the disorder in FH patients. The number of poly-L-lysine/DNA complexes corresponding to 3 mg of DNA that we have introduced into the animal in our first approximation to these experiments accounts for 0.01% of the total number of asialoglycoprotein receptors in the liver. Consequently, a linear correlation between increasing concentration of DNA complexes and expression of the PCK-hLDL receptor gene is to be expected.

2. Rabbit #737: injection of the poly-L-lysine/DNA complex containing 9 mg of the chimeric PCK-hLDLR gene.

Figure 14:
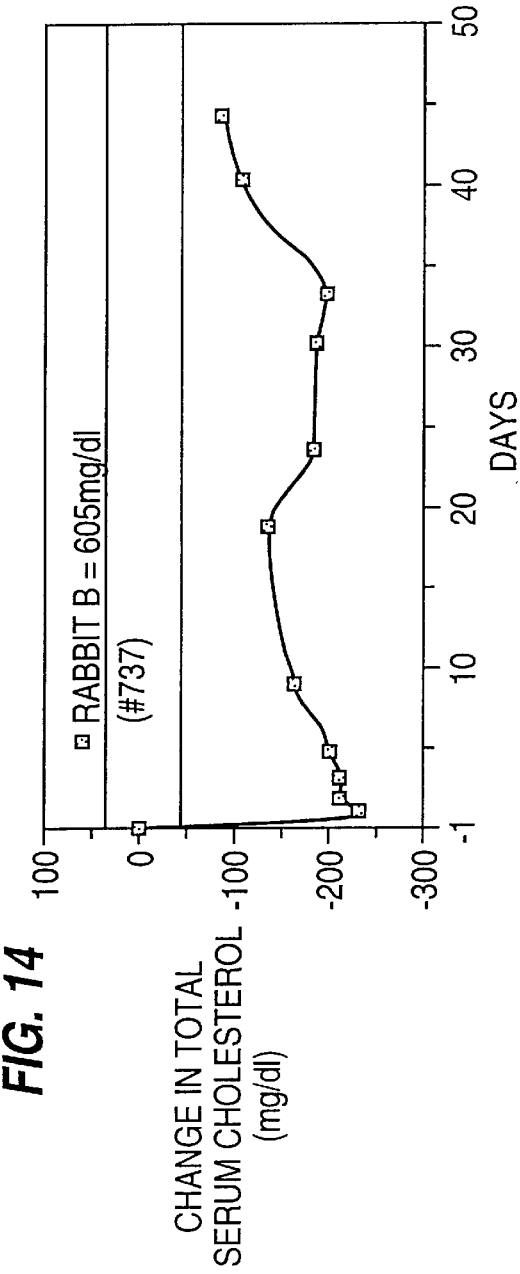

In our second experiment, 9 mg of the PCK-hLDLR gene appropriately condensed with galactosylated poly-L-lysine were administered to rabbit #737. As shown in FIG. 14, the treatment resulted in a 38% reduction of total serum cholesterol levels which lasted for about 5 weeks. Thus, a 3-fold increase in the dose of DNA complex resulted in a 2-fold reduction in total serum cholesterol levels.

3. Rabbit #16: injection of the DNA complex containing 3 mg of the CMV-hLDLR gene.

The promoter for the cytosolic form of the PEPCK gene has the advantage of driving expression in the liver almost specifically and in a regulated fashion. Although they are neither physiologic nor regulated, viral promoters confer high levels of expression to linked structural genes. The chimeric CMV promoter/enhancer has been used with success for gene therapy in WHHL rabbits using adenoviruses for gene transfer. Recently, Kozarsky et al. have reported that the CMV promoter/enhancer and the chimeric β-actin/CMV promoter were the promoters of choice in order to obtain highest expression of the human LDL receptor gene transferred to WHHL rabbits using adenoviral infection. Based on these observations, we injected the chimeric CMV-hLDLR gene in order to increase the level of expression of the human LDL receptor gene in the liver of WHHL rabbits.

Figure 15:
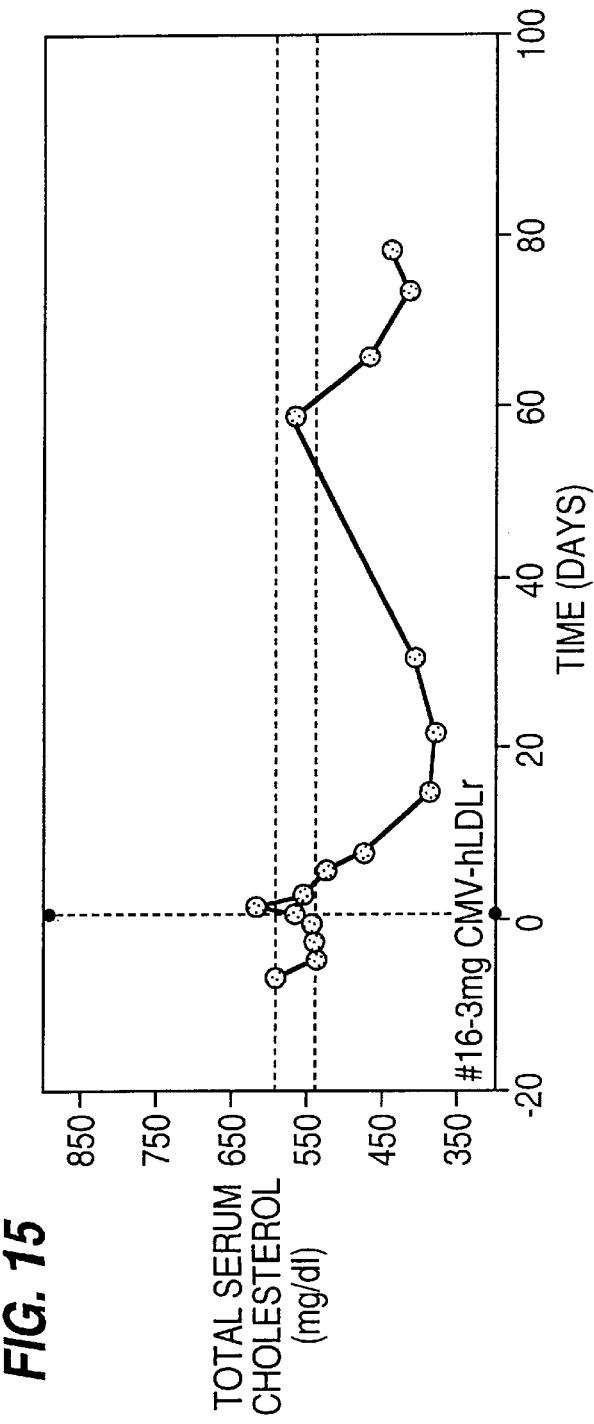

The administration of a DNA complex solution containing 3 mg of the chimeric CMV-hLDL receptor gene to rabbit #16 resulted in a maximal reduction of 30% in total serum cholesterol levels (FIG. 15). Eleven weeks after the injection cholesterol levels are still 20% below those observed before the treatment.

4. Rabbit #775: repeated administration of the DNA complex containing 3 mg of pCMV-hLDLR.

Figure 16A:
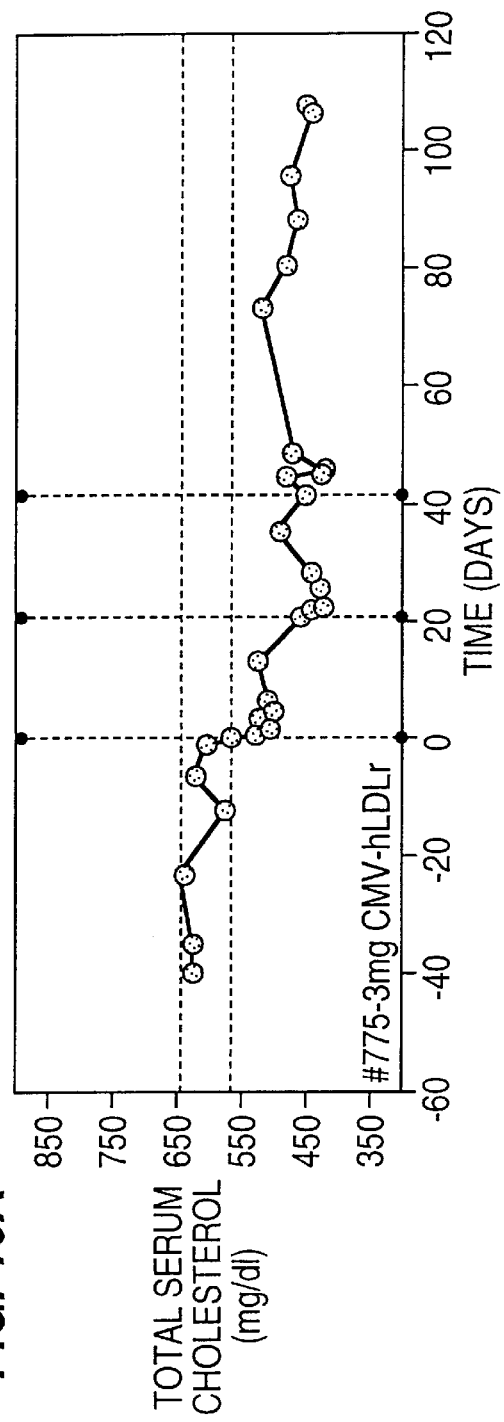

Three mg of pCMV-hLDLR contained in a DNA complex solution were injected into rabbit #775, causing a maximal 24% reduction in the concentration of cholesterol in the blood 3 weeks after the treatment (FIG. 16A).

The life-span of hepatocytes is reported to be about 108–150 days, so that the persistence of the introduced DNA is limited. Furthermore, a larger therapeutic effect may be of interest after a single injection of the DNA complex. Thus, it may be necessary to inject a patient multiple times to ensure the appropriate level of LDL receptor in the liver. We tested the effect of injecting the DNA complex several times into the same animal. Rabbit #775 has been reinjected twice with 3 mg of the pCMV-hLDLR DNA complex being each injection spaced by 3 weeks. The repeated administration of the complex did not result in a further significant reduction in total serum cholesterol levels.

5. Rabbit #774: repeated administration of the DNA complex containing 3 mg of pCMV-hLDLR.

Figure 16B:
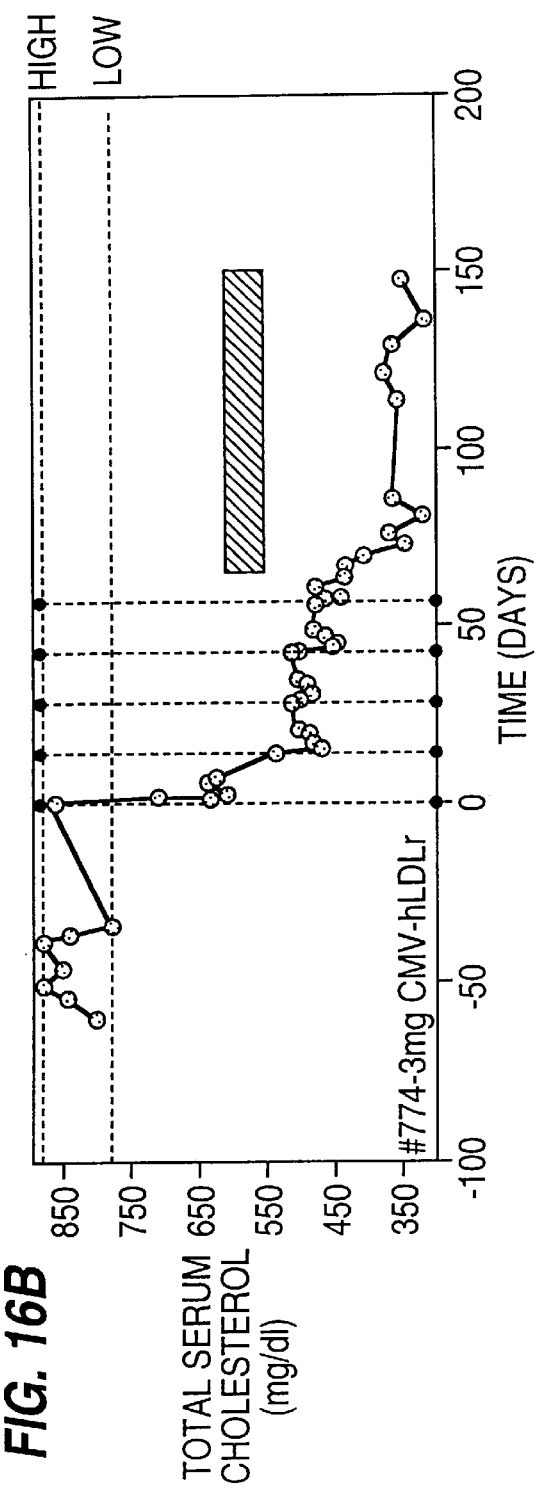

Rabbit #774 was injected with 3 mg of the pCMV-hLDLR complex. We observed a 36% decrease in the cholesterol levels in the blood (FIG. 16B). To date four reinjections once every 2 weeks have been performed with the same amount of DNA complex. Two of them have resulted in a minimal effect while the other two in a null reduction of total serum cholesterol levels. However, after five administrations of the DNA complex solution containing 3 mg of pCMV-hLDLR, the concentration of cholesterol has dropped about 48% with respect to pre-treatment levels.

6. Administration of lovastatin to rabbit #774: inhibition of the endogenous synthesis of cholesterol.

As described in the introduction, there is a pathway for cholesterol synthesis inside the cell. A failure in repressing this metabolic pathway even when the hepatocyte is supplied with cholesterol through the uptake by the human LDL receptor could possibly inhibit further clearance of cholesterol. Lovastatin is a known inhibitor of HMG CoA reductase, the rate-limiting enzyme in the synthesis of cholesterol. Thus, the treatment with this drug of a rabbit that has been injected repeated times with the DNA complex should indicate if cholesterol synthesis was the limiting factor for a further reduction of total serum cholesterol levels. Rabbit #774 has been treated with 10 mg of lovastatin per day for 10 weeks. A further 20% reduction in the levels of cholesterol has been observed. The inhibition of the endogenous pathway for cholesterol synthesis has thus brought the cholesterol concentration of rabbit #774 to 40% of that prior the first gene transfer (FIG. 16B).

7. Injection of the DNA complex containing an irrelevant DNA.

Figure 17:
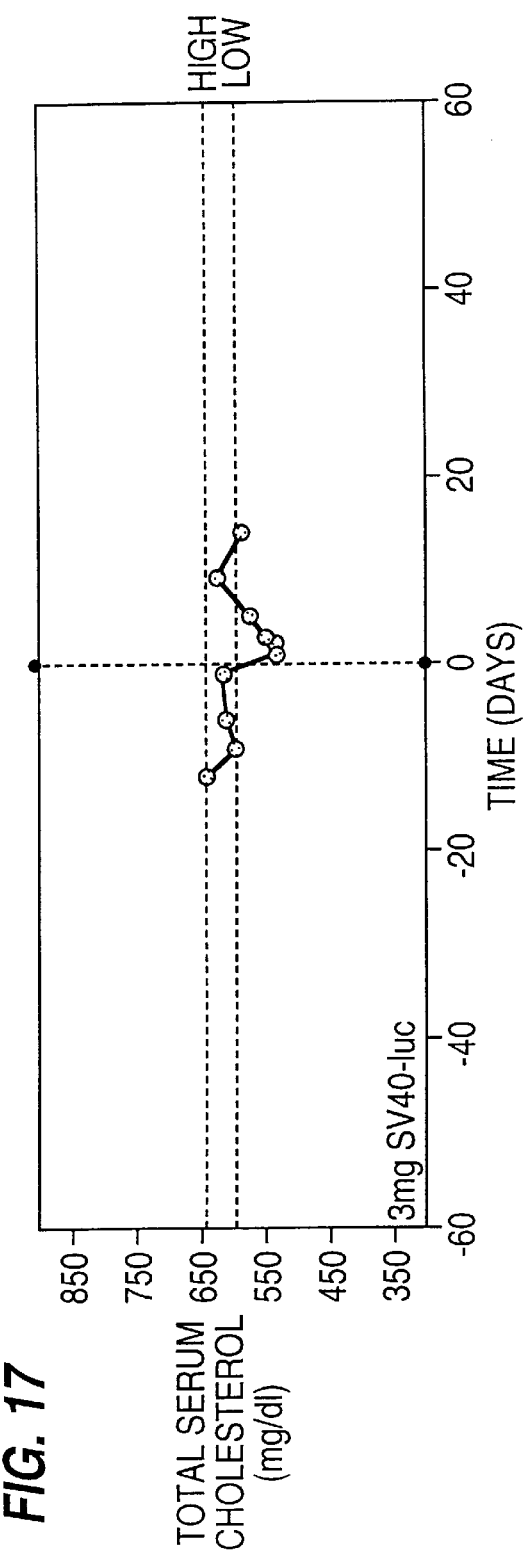

In order to control for a possible artifactual reduction in total serum cholesterol levels by injecting rabbits with the galactosylated poly-L-lysine/DNA complexes in a solution with high NaCl concentration (~900 mM), we have administered a DNA complex solution containing an irrelevant DNA such as the luciferase gene into rabbit #775. FIG. 17 shows that the injection results in a non-significant ($\leq 12\%$) and transient ($\leq 5$ days) reduction in the serum cholesterol concentration. In addition, we have also injected inappropriately condensed DNA complexes encoding the PCK-hLDLR gene. They result in a null or minimal and transient decrease in the cholesterol levels in the blood as well. Thus, we have confirmed that the reduction in total serum cholesterol levels after the injection of appropriately condensed DNA particles encoding the human LDL receptor gene are not a result of either the high NaCl concentration of the solution or the presence of galactosylated poly-L-lysine/DNA particles.

8. Detection of the transferred DNA in the liver of rabbit #774.

The DNA complex used in this project is targeted to the hepatic asialoglycoprotein receptor using galactose as a ligand. It is known that macrophages have a similar receptor which is able to clear galactosylated particles larger than 15 nm from the bloodstream.

In order to prove that the human LDL receptor DNA was delivered to the hepatocytes, we performed a liver biopsy in rabbit #737 60 days after the injection of 3 mg of the PEPCK-hLDL receptor gene. Total DNA was isolated and subjected to PCR amplification with the primers described above, together with total DNA from the liver of a non-injected rabbit. The expected band of 1,100 bp was detected in the lane corresponding to the treated rabbit but not in the non-treated animal.

9. Evaluation of the immune response of rabbit #774 after the repeated administration of the poly-L-lysine/DNA complex.

In the field of gene therapy, immunogenicity of the delivery vehicle is often a concern. While retroviral vectors can escape detection by the immune system, it has been reported that adenoviral vectors do not. The success of a second administration of adenoviral particles for the transfer into Watanabe rabbits of the human LDL receptor gene was blocked by the onset of an immune response against the viral proteins (REF Kozarsky).

The system for receptor-mediated gene transfer has not been studied in depth in regard of its immunogenicity. It has been reported that after the repeated administration of an asialoorosomucoid-poly-L-lysine/DNA complex into mice, neutralizing antibodies against the asialoorosomucoid and poly-L-lysine components of the complex but not against the DNA can be detected at a dilution 1:1000 (REF). Ferkol et al. also reported the detection of circulating antibodies at a 1:2000 dilution against the Fab fragment-poly-L-lysine but not the DNA moiety of a complex upon repeated administration into mice.

We thus needed to test if the use of galactosylated-poly-L-lysine for the condensation of DNA was immunogenic as well. For this purpose, the presence of antibodies against the galactosylated-poly-L-lysine-DNA complex was evaluated in sera obtained from rabbit #774 at different time points before and after the repeated administration of the complex. In a first experiment, the DNA complex solution containing 1 $\mu$g of DNA was adsorbed to the wells of a microtiter plate and then incubated with sera at dilutions 1:3, 1:30 and 1:300. Bound antibodies were detected with an anti-rabbit secondary antibody conjugated with alkaline phosphatase. There is an increase of antibodies in the serum of rabbit #774 upon repeated administration of the DNA complex. In fact, they start to be detectable after the third injection of the DNA complex but not after the first or the second. In addition, it has to be emphasized that only at dilutions 1:3 and 1:30 could a response be detected.

A second experiment was performed in order to establish which moiety of the DNA complex is responsible for inducing the weak though clear immune response. We then adsorbed to the microtiter plate wells either 1 $\mu$g of DNA, freshly prepared DNA complex containing 1 $\mu$g of DNA or the corresponding amount of galactosylated-poly-L-lysine. The results show that the galactosylated-poly-L-lysine moiety accounts almost entirely for the induction of an immune response against the complex in Watanabe rabbits.

Discussion

The data presented here strongly suggest that the method has been able to at least partially correct hyperlipidemia in WHHL rabbits.

FIGS. 13–16 clearly show that a single injection of the DNA complex containing the human LDL receptor gene results in a significant decrease of total serum cholesterol levels in WHHL rabbits. This reduction ranges from 20% in rabbit #676 to 38% in rabbit #737. In contrast, we show that the administration of a non-relevant plasmid DNA such as pSV40-luciferase (FIG. 17) or of a human LDL receptor-encoding plasmid that is not appropriately condensed (FIG. 17) results in a null or non-significant decrease in serum cholesterol.

We have used two different promoter regions for the regulation of expression of the human LDL receptor gene. It is tentatively suggested that the CMV regulatory region confers higher levels of expression in the liver of rabbits than the promoter for the cytosolic form of the rat PEPCK gene. This observation may not be correct for every species. PEPCK activity in the liver of rabbits is characterized by being only 10% due to the cytosolic isozyme. In addition, stimulation of the cytosolic gene results in only a 2-fold induction of activity. Thus, the PEPCK promoter may not be the best choice for this species. But the use of a physiologic and tightly regulated promoter as the one for the PEPCK gene may well be the one of choice over a strong but viral promoter as the CMV in other species or for the treatment of other genetic diseases.

In order to determine the time-course of the therapeutic effect rabbits #676, #737 and #16 were subjected to a single injection of the DNA complex containing the human LDL receptor gene. The reduction in the levels of cholesterol in the blood persisted for 4 weeks in rabbit #676 and for 5 weeks in rabbit #737. Based on previous experiments performed in rats where the expression of the transfected pPEPCK-human Factor IX gene was shown for up to 140 days, we were expecting a longer duration of the effect. Different factors can explain this premature termination of the corrective effect of hyperlipidemia. It is well known that rabbits are highly immunogenic and that rats are not. The synthesis in the WHHL rabbits of a human protein after the introduction of the human LDL receptor gene could possibly trigger an immune response against the foreign protein, although there is an 80% homology between both species at the protein level. In addition, hepatocytes seem to have a limited life-span. Some studies in the rat indicate that the life-span of hepatic cells is 108–150 days. Based on this observation, 40% of the increase in cholesterol levels 5 weeks after the introduction of the DNA complex could result from the physiological turnover of liver cells. However, this fact cannot account for 100% of the increase. In addition, it would contradict with the long-term expression observed in rats injected with pPEPCK-human FIX. Another possible explanation for the premature termination in the therapeutic effects resulting from the expression of the human LDL receptor gene would be inactivation or degradation of the transferred DNA.

The theoretical number of poly-L-lysine-DNA complexes that can be formed with 3 mg of DNA accounts for 0.01% of the total number of asialoglycoprotein receptors in the liver. Consequently, we would expect that an increase in the dose of DNA complex results in an enhanced therapeutic effect. To study the dose-response relationship, we have injected rabbit #676 with 3 mg of pPCK-hLDLR and rabbit #737 with 9 mg of the same DNA. As shown in FIGS. 13 and 14, a 3-fold increase in the dose of DNA complex results in a 2-fold higher reduction in cholesterol levels. Although these data do not establish linear correlation, an increase in the dose clearly results in an enhanced response.

If we consider the poly-L-lysine/DNA complex as a potential drug, it is desirable to be able to repeatedly administer it to the same animal. For this reason, rabbit #774 has been subjected to repeated administration of 3 mg of the CMV-hLDLR DNA once every 2 weeks. After an initial decrease of 36% in serum cholesterol levels following the first injection, the effect of the repeated administration of the DNA complex has not been consistent. Rabbit #775 has been treated 3 times with 3 mg of the CMV-hLDLR DNA. Again, after an initial 24% reduction in the cholesterol levels, the second and third treatments have not resulted in a clear effect. We can find three possible explanations for these results. First, that the DNA complexes were not appropriately condensed. DNA upon condensation with poly-L-lysine can result in three different structures: aggregated (condensed particles out of solution), tightly condensed and relaxed. Only DNA tightly condensed into small particles is effective in delivering genes in vivo. Second, that the rabbits are producing neutralizing antibodies against the vehicle. We have some preliminary data regarding the immune response of rabbit #774 against the poly-L-lysine-DNA complex. Third, further clearance of cholesterol from the blood is limited by an impairment in the endogenous metabolism of cholesterol in the hepatocyte of the mutant Watanabe rabbit. In order to test this last hypothesis, rabbit #774 was treated with lovastatin (10 mg/day), a known inhibitor of HMG CoA reductase, for 10 weeks. The observation of a further 20% reduction in the cholesterol concentration suggests that the inhibition of cholesterol synthesis in the hepatocyte is not complete even when the cell is supplied with cholesterol upon uptake of LDL by the heterologous LDL receptor.

Preliminary results regarding the immunogenicity of the galactosylated-poly-L-lysine/DNA complex indicate that the repeated administration triggers the onset of an immune response in the Watanabe rabbit. They also show that circulating antibodies can recognize the galactosylated-poly-L-lysine but not the DNA moiety. These results agree with previous reports regarding the immunogenicity of an asialoorosomucoid-poly-L-lysine/DNA complex and of an Fab-poly-L-lysine/DNA complex. Though it is clear that the complex designed in our laboratory can in fact elicit an immune response upon repeated administration in the same animal, it has to be noticed that we could only detect circulating antibodies at much lower dilutions (1:3 and 1:30 as compared to 1:1000 and 1:2000 in their case). This observation might be indicative of its better ability to escape detection by the immune system. Nevertheless, serum from more animals subjected to repeated administration of the DNA complex need to be tested for the presence of neutralizing antibodies against the complex in order to conclude that immunogenicity is responsible for the failure of repeated injections in further lowering the cholesterol levels in the Watanabe rabbits.

EXAMPLE 5

Direct Injection Of Complexed vs. Naked DNA Into Muscle

Methods

Three rats per experimental set were used in the experiments involving direct tissue injection of the DNA complex.

One hundred micrograms of naked DNA containing the SV40-luciferase gene was injected into the liver and abdominal muscle of one of the animals. The same amount of the SV40-luciferase plasmid was complexed to poly-L-lysine and condensed as described above and injected as well into the liver and abdominal muscle of the other two animals. The rats were sacrificed 48 hours post-injection. A piece of liver and abdominal muscle were obtained for the measurement of luciferase activity.

Results

Figure 9:
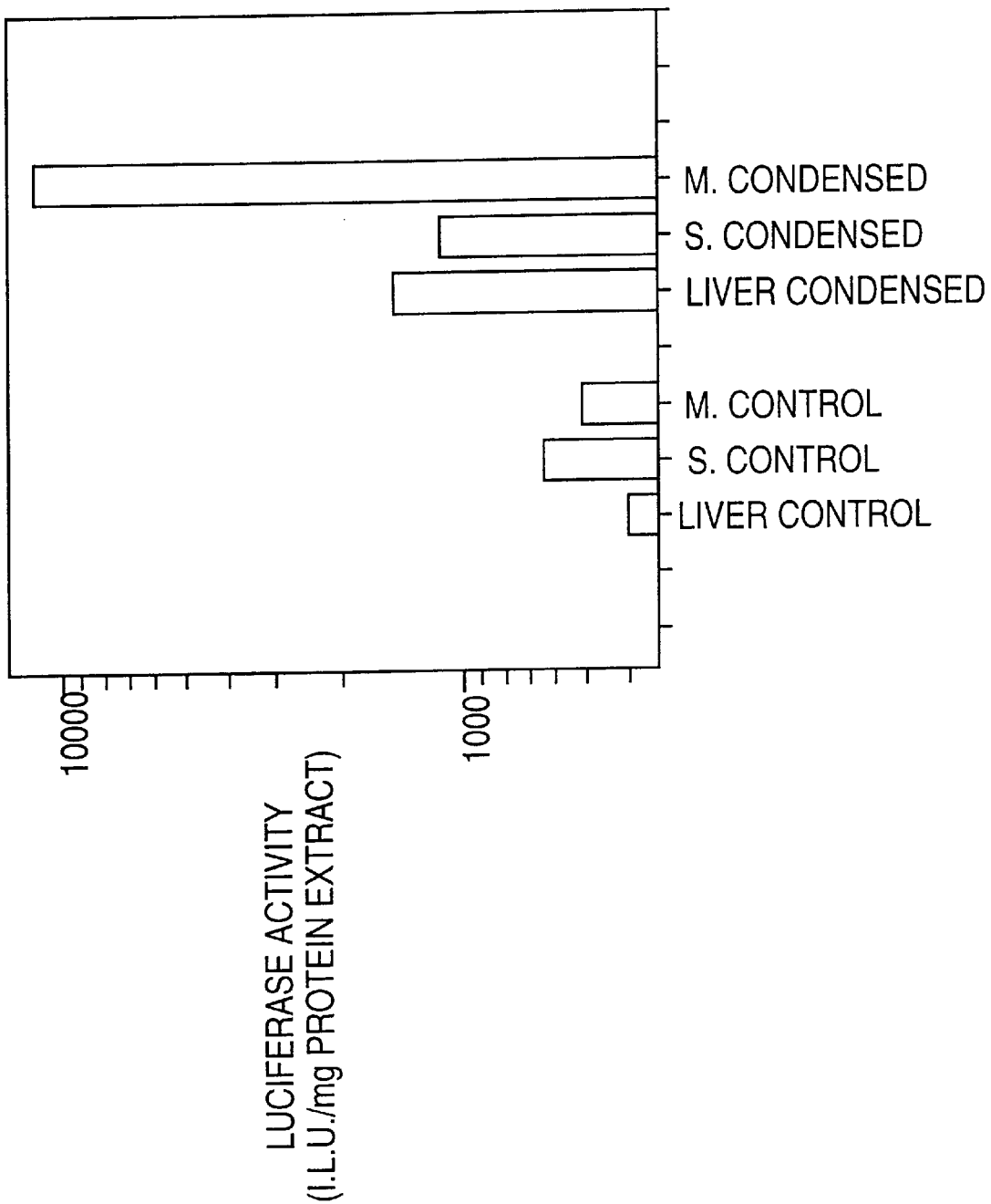

Evaluation Of Direct Injections Of The DNA Complex Into The Liver And Muscle Of Rats: The successful transfer of naked DNA into muscle cells of mice by direct injection has been reported. Prolonged and high levels of expression of a chimeric gene containing the Rous sarcoma virus (RSV) regulatory region linked to the luciferase cDNA were observed in the experiments. We have investigated the advantages of using DNA complexed to poly-L-lysine and condensed over using free DNA, when DNA has to be transferred into the liver or muscle by direct injection. Three rats have been used for these experiments. One hundred micrograms of naked DNA encoding SV40-luciferase were injected into the liver and abdominal muscle of one of the animals. The same amount of the pSV40-luciferase plasmid complexed to poly-L-lysine and condensed as described above was injected as well into the liver and abdominal muscle of the other two animals. Rats were sacrificed 48 hours post-injection. A piece of liver and abdominal muscle were homogenized in lysis buffer and cell lysates were analyzed for luciferase activity. All luciferase measurements were performed in triplicate, expressed as an average of the values and standardized for total protein. FIG. 9 shows the integrated luciferase units per mg of protein in the two different sets of animals. The efficiency of transfection of DNA complexed to poly-L-lysine and condensed seems to be slightly higher when injected into the liver. However, it appears to result in a much higher efficiency when introduced into muscle tissue. We observe a 20-fold higher luciferase activity in the sample of muscle injected with the condensed DNA compared to the one injected with naked DNA. We think that highly condensed and packaged DNA may be protected against nucleases and may be more stable. In addition, poly-L-lysines may increase the efficiency of nuclear transport once inside the cell. First, the small size of the complex may allow its passage through nuclear pores and second, strings of positively charged amino acids as lysine and arginine are known to be nuclear localization signals (NLS) in various nuclear proteins. Regarding the differences found between the response in the liver and in the muscle, it is most probable that the characteristic interconnected structure of skeletal muscle cells makes them a better target for the passive diffusion of DNA from cell to cell. This would easily allow the distribution of the DNA complex along the muscle tissue and its transport to the nuclei.

EXAMPLE 6

Direct Injection Of Naked vs. Condensed DNA Into The Brain: Gene Transfer Of Retinal Ganglion Cells In Vivo Introduction Insertion of foreign DNA into adult neurons has potentials for the study of normal neuronal physiology and for the treatment of neural diseases. Gene transfer in neurons has been achieved using viral vectors, however it requires sophisticated methodologies and usually cells transfected can not be restricted to any particular type of neuron.

Axonal Retrograde transport is a continuous physiological process that has been found to transport a large variety of different types of molecules. Many molecules are known to be incorporated into the axon lumen through endocytosis, whether they are adsorbed or fluid-phase particles. in the situation where axons have been severed, it is postulated that soluble particles from the extracellular space can diffuse into the axon and move towards the soma.

In the present experiments we tested whether plasmid DNA naked or condensed into a compact spheroid, applied to the cut end of retinal ganglion cell axons in the optic nerve or to the tectum of the brain is transported back to the soma and expressed into protein.

Methods

Three plasmids under the control of one of three promoters which are effective in a wide variety of eukaryotic cell types were used: RSV-lacZ, CMV-lacZ and SV40-luc. They were prepared at different concentrations ranging from 1 to 20 $\mu g/\mu l$. pCMV-lacZ and pSV40-luc were complexed with poly-L-lysine (1:1) by Jose Carlos Perales (PNAS, 1994).

Assessment of retrograde transport of the plasmid complex to the retinal ganglion cell somas was done using epifluorescence microscopy FITC-poly-L-lysine was used to form complexes with pCMV-lacz. To assess the retrograde transport of pure plasmid, pRSV-lacZ was digested in one site using Hind III. Biotin-dUTP was then linked to the 3'-OH ends of pRSV-lacZ by reaction with Terminal dexynucleotidyl Transferase. Plasmid was then precipitated and washed from free biotin-dtyrp and resuspended at 2 $\mu g/\mu l$.

Adult Wistar rats were anesthetized and their optic nerves were exposed. 1.5 $\mu l$ of the plasmid solution (different concentrations and plasmids) was applied covering the Optic Nerve. Optic nerve axons were then cut avoiding the retinal blood supply. Another 1.5 $\mu l$ of the same plasmid solution was applied in soaked gelfoam. The conjunctiva was then closed. Same procedure was done in the contralateral eye using unspecific plasmid. Animals were sacrificed 3 days later. For direct injection into the tectal area, animals were anesthetized and injected stereoscopically into the tectal area of the brain with naked DNA or condensed DNA.

For liquid β-galactosidase assays, retinas were kept at −70° C. until they were cell-lysed by repeated thawing and freezing. Tissue was centrifuged at 12000 rpm for 2 min and the supernatant collected and analyzed for protein content. Volumes containing 360 $\mu g$ of protein were incubated overnight at 37° C. in buffer A containing 15 mg/ml chlorophenol red B-D-galactopyranoside (CPRG). The absorbance was recorded.

For luciferase assays were done in lysis supernatants of retinas added with luciferase assay buffer. Samples were put into a luminometer which was injected with D-luciferin and then registered luminiscence.

For in situ β-galactasidase assays (for pRSV-lacZ and pCMV-lacZ) retinas were fixed in 2% formaldehyde, 0.5%; glutaraldehyde, PBS for 30 min., washed in PBS and incubated for 6 hrs at 37° C. in 1 mg/ml X-Gal, 4 mM potassium ferrocyanide, 4 mM potassium ferricyanide, 2 mM $MgCl_2$, PBS pH 7.3, 0.02% Nonidet p-40, 0.01% Deoxycholate. Tissue was then rinsed arid analyzed immediately. Counts of blue labeled cells were made to estimate the percentage of transfected cells.

Results

1) Administration of plasmid DNA to the cut end of rat optic axons results in its retrograde transport to the cell body. Double labeled field (confocal microscopy) from a retina 2 days after administration of FITC-polylysine/pCMV-lacZ complex at the cut end of the optic nerve and then incubated in propidium iodide showed that FITC (green), Propidium iodide (red) and the mixture of both nuclei double labeled (yellow), counted in randomized fields represented about 45% of the population of retinal ganglion cells.

Microscopic fields taken at different magnifications showed blue colored cells in the retinal ganglion cell layer following in situ β-galactosidase assay in retina. 20 μg/μl of pRSV-lacZ were administered at cut optic nerve and comparison was made with contralateral eye treated with pSV40-luc. Cells positive for β-galactosidase were noted to be in the range size known only for ganglion cells in the retina. These cells were counted in randomized fields and were estimated to represent 35% of total ganglion cells.

2) Plasmid DNA in retinal ganglion cells is expressed in a dose dependent manner and the condensed DNA is expressed at higher efficiency. Luciferase activity in retinas from rats whose severed optic nerves were administered with pSV40-luc at increasing concentrations, as compared with retinas just axotomized, or treated with the non-specific plasmid pCMV-lacZ (1μg/μl) showed concentration dependent increase in activity of pSV40-luc.

The results of β-galactosidase activity in retinas from rats whose severed optic nerves were administered with pCMV-lacZ, as compared with retinas just axotomized, or treated with non-specific plasmid pSV40-luc (10 μg/μl) showed that the highest activity was registered from the maximum concentration of pCMV-lacZ. pCMV-lacZ complexed with poly-lysine produced higher activity in β-galactosidase than non-specific plasmid.

3) This method can be used in the transfer of specific genes to precise neuronal types through their projections.

Figure 10:
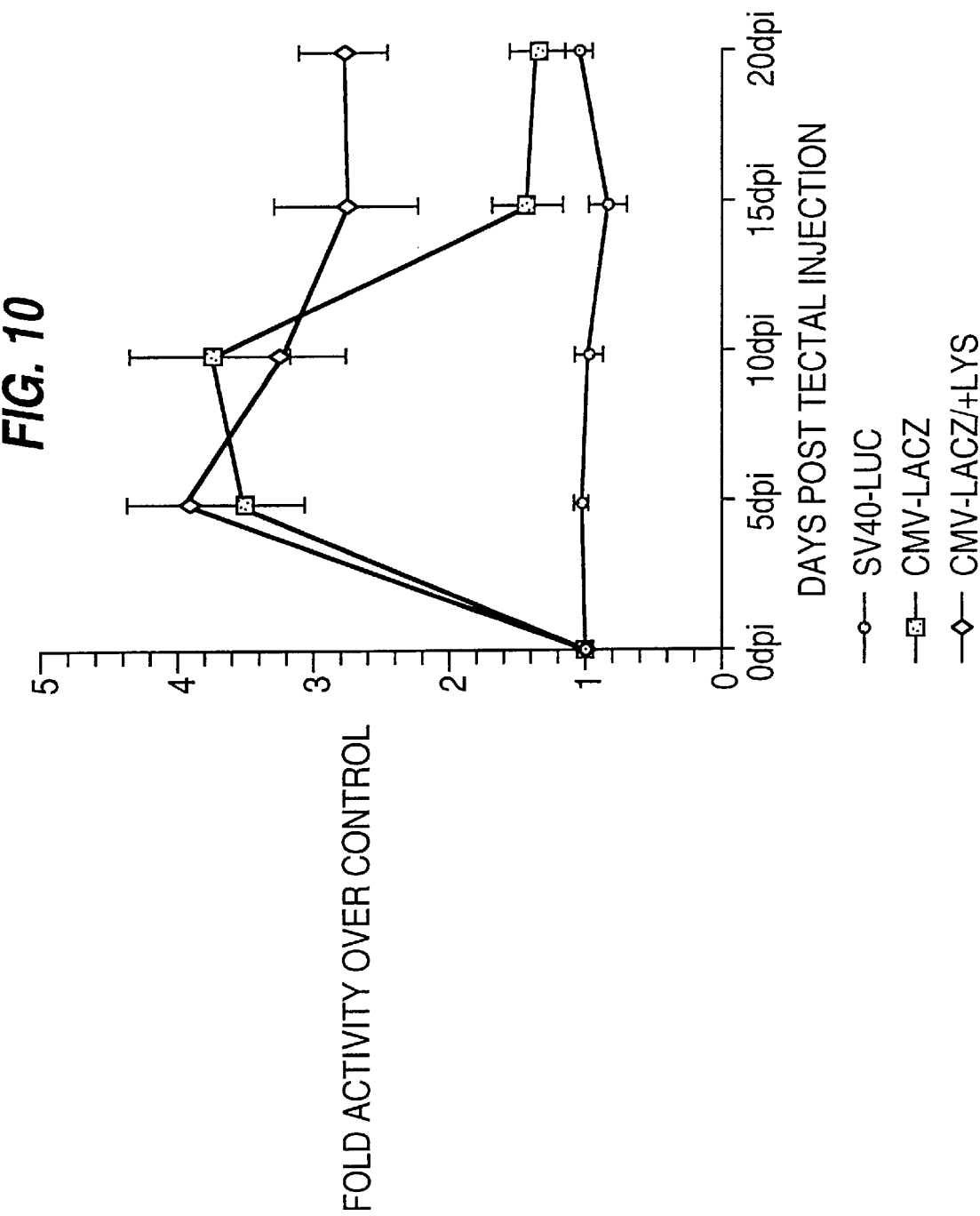

4) Intratectal injections of naked and polylysine condensed plasmid DNA can achieve high levels of expression in the cell body of the neuron over 20 days. When the DNA is not condensed with poly-L-lysine the level of expression returns to background after 10 days post-injection (FIG. 10).

EXAMPLE 7

Improved Reagents For Targeted Delivery Via The Polymeric Immunoglobulin Receptor In Example 3 above, it was demonstrated that Fab fragments prepared from polyclonal rabbit anti-rat secretory component (SC) antibodies mediate the transfer of DNA into the lungs of rats. The transfer was mediated by the polymeric immunoglobulin receptor (pIgR). This transfer system provides a means for targeting macromolecules, such as DNA, into the lung from the blood rather than the airway. Transfer via the blood is advantageous when therapeutic or pharmaceutical complexes are to be transferred to the lungs of individuals, such as cystic fibrosis (CF) patients, who have plugged airways.

CF patients lack expression of functional cystic fibrosis transmembrane conductance regulator (CFTR) in airway epithelial cells and submucosal glands which results in chronic, suppurative pulmonary disease. CF is an autosomal recessive disorder and is therefore amenable to correction by gene transfer.

In human airways, the distribution of the pIgR and CFTR coincide, as both are expressed on the surface epithelium and the serous cells of submucosal glands. As described above, gene transfer complexes, which consist of the Fab portion of rabbit polyclonal antibody directed against the pIgR coupled to polylysine condensed with plasmids containing reporter genes injected intravenously into rats resulted in maximal luciferase activity of 500,000 light units per mg homogenized lung protein and labelling of about 20% of tracheal epithelial cells with lac Z and 70% with the interleukin 2 receptor gene. Activity persisted for about two weeks.

The exquisite specificity and targeting of receptor-mediated gene transfer minimizes the amounts of gene transfer complex and plasmid DNA needed, and limits ectopic expression of the transgene. However, areas in which ectopic expression might be expected, e.g., liver and intestinal epithelium (sites of pIgR receptor concentration outside of the lung), are also sites of CF disease, and might benefit from delivery of normal CFTR. The large packaging capacity permits inclusion of regulatory sequences to mimic native gene regulation. Reactivation of a pathogenic virus cannot occur. For CF, delivery of a pharmaceutical or therapeutic compound from the blood avoids accessing the lumens of plugged or diseased airways, and allows treatment to readily reach submucosal gland cells, which express abundant CFTR, but are difficult to reach via the lumen. However, gene expression is transient. In order to treat a lifelong disease like CF, the complex must be administered repeatedly. With multiple administrations (greater than two injections), antibodies, all directed against the Fab, are induced and the complex becomes less efficient for gene transfer. In addition, for human use, the reagents must be characterized and purified. The reagent used in Example 3 was constructed by coupling the Fab portion of polyclonal antibodies with poly-L-lysine using SPDP or EDC. Polyclonal antibodies are heterogeneous (only 3% of the polyclonal antisera contains antibodies which are specific for the pIgR), the coupling reagents are nonselective, and heterogeneous product results. Homogeneous product may provide improved gene transfer complexes.

The present invention addresses two of the problems associated with effective gene therapy: the immunogenicity (i.e., antigenicity) and molecular heterogeneity of the gene transfer complex. Thus, to improve a very promising strategy of gene therapy, the immunogenicity of the gene transfer complex is minimized or abolished by constructing chimeric monoclonal antibodies and single-chain antibodies. As the heterologous sequences in the Fabs are the most likely cause of the immune response, most of the heterologous sequences in the Fabs are replaced with same-species sequences (i.e., for use in humans, chimeric rodent-human monoclonals are generated). To further reduce the immunogenicity of the gene transfer complex, single chain antibodies were generated. The molecular heterogeneity of the complex is reduced or abolished by using monoclonal antibodies directed against human SC, and by constructing fusion proteins comprising a single-chain Fv molecule, directed against the pIgR, in a fusion protein with a polycation. These fusion proteins obviate the need to chemically couple a polycation to the Fab.

Although the above discussion focused on treatment of CF, treatment of other diseases will benefit from receptor-directed gene transfer and from pIg receptor-directed gene transfer in particular. For example, other genetic disorders which affect the lung, such as $\alpha_1$-antiprotease deficiency would benefit from epithelial gene transfer.

The present invention contemplates the fusion proteins comprising a single-chain Fv directed against human SC linked to therapeutic proteins, such as $\alpha_1$-antitrypsin, cytokines (e.g., interleukin-2, interleukin-10) and peptide antibiotics (e.g., aerosporin, amphomycin, aspartocin, bacitracins, caperomycins, colistins, dactinomycins, glumamycins, gramicidin D, gramicidin S, mikamycin B, polymiyxins, pristinamycin, siomycin, staphylomycin S, thiotrepton, tyrocidines, tyrothricin, valinomycin, vancomycins, veramycin B, viomycins, etc.). The Fv portion of the fusion protein may be separated by a linker or spacer from the portion comprising the therapeutic protein. The spacer may vary from 0 to 30 amino acid residues in length.

The use of antibodies (including Fab fragments, single-chain Fv and single-chain Fv fusion proteins) directed against the pIgR to target the delivery of genes or therapeutic proteins is particularly useful in the treatment of diseases where the sites of disease are relatively inaccessible to conventional therapy. For example, targeting therapeutic (i.e., pharmaceutical) complexes or compounds to the pIgR allows the delivery of therapeutic compounds to the lung, bowel and biliary tract, sites which are difficult to treat using conventional approaches.

Acute disorders might also be ameliorated by direct delivery of genes to airway epithelium using the methods of the present invention. For example, patients who must be treated with high $FIO_2$ or patients with the acute respiratory distress syndrome (ARDS) would benefit from high levels of superoxide dismutase expression in the airways. Patients about to undergo chemotherapy with bleomycin might have their lungs protected against dose-limiting toxicity by transfer of bleomycin hydroxylase to the lung. Treatments for acute stresses may require only transient gene expression. Moreover, the use of antibody-mediated receptor-targeted gene therapy directed at receptors other than the pIgR will allow the treatment of a variety of disorders. The methods described below, while illustrated using the pIgR system, are generally applicable for the development of antibodies, including single-chain antibodies, against receptors other than the pIgR.

a) Production Of Monoclonal Antibodies Directed Against Human Secretory Component
      i) Purification Of Human Secretory Component Free secretory component (SC) is purified from human colostrum according to published methods [Kobayashi (1971) *Immunochemistry* 8: 785–800]. Briefly, human colostral whey is applied to a DEAE-cellulose column. The free SC is eluted by application of 0.01M Na-phosphate buffer (pH 7.6). Ammonium sulfate (27 g ammonium sulfate per 100 ml of the solution at pH 7.6) is then added. The solution is centrifuged at 10,000 rpm for 15 min, the precipitate is discarded and the supernatant (500 mg protein) is dialyzed against 0.005M sodium acetate buffer, pH 5.0. The dialyzate is then applied to a CM-cellulose column (2×25 cm) equilibrated with 0.005M sodium acetate buffer, pH 5.0. A linear gradient consisting of 0.005M (300 ml) and 0.5M (300 ml) sodium acetate buffer, pH 5.0 is applied. Fractions containing free SC are identified (e.g., by double immunodiffusion in an agar gel with anti-bound SC serum), pooled and then concentrated by gel-filtration on a Sephadex G-200 (Pharmacia) (2.4×100 cm) with $\mu$=0.05. The Sephadex G-200 column is equilibrated with Tris-HCl buffer, pH 8.0 containing 1M NaCl and is run using a flow rate of 20 ml/hr; 5 ml fractions are collected. The absorbance of material coming off the column is measured at 280 nm; two major peaks are obtained with the second peak containing the free SC (at about fractions 50–65). The SC-containing fraction is re-applied to the same G-200 column, dialyzed against distilled water and lyophilized. The purified free SC is then optionally adsorbed twice on a column of immobilized antibodies prepared against human lactoferrin, a protein that often co-purifies with SC.

ii) Production Of Anti-Human SC Monoclonal Antibodies

Mice were injected intraperitoneally with an initial dose of 50 $\mu$g purified human free SC in 100 $\mu$l sterile PBS emulsified with an equal volume of complete Freund's adjuvant. Following the initial immunization, the mice were boosted three times, 3–4 weeks apart, with 25 $\mu$g human free SC in 100 $\mu$l sterile PBS, emulsified with an equal volume of incomplete Freund's adjuvant. Serum was screened in an ELISA assay against purified human free SC (ELISAs were conducted as performed in Example 4 with the exception that purified human SC was used to coat the wells of microtiter plates). Mice with high antibody titers were sacrificed and their spleen cells were fused with Sp2/0-Ag14 murine myeloma cells (ATCC CRL 1581). The hybridoma cells were selected in HAT medium and cloned by limiting dilution using protocols known to the art [Harlow and Lane (1988) *Antibodies: A Laboratory Manual*, Cold Spring Harbor Laboratory Press, Cold Spring Harbor, N.Y., pp. 196–223].

Positive clones were identified by screening culture supernatants derived from the hybridoma clones in an ELISA assay against purified human SC. Several positive hybridoma clones were identified; these clones secrete monoclonal antibodies which cross-react with secretory IgA (sIgA), and therefore probably recognize epitopes outside the binding site for the natural ligand (the first Ig-like domain is the natural ligand binding site). Therefore, sIgA (the natural ligand for the pIgR) and Fab fragments derived from these MAbs are not expected to compete for binding to the pIgR. Several of these anti-human SC MAbs with the best affinities were selected for further studies (hybridomas 4121 and 4114 were among those selected). Hybridoma 4121 was selected because in FACS analysis of cells which express the pIgR, the 4121 MAb recognizes the receptor in the context of the cell surface better than the other MAbs examined. Other hybridomas were selected for further studies based on the productivity of the cells and the affinity of MAbs.

Alternatively, monoclonal antibodies capable of binding to human SC were also generated by immunization of rats with a 16 amino-acid synthetic peptide [YYPDTSVNRHTRKYWC (SEQ ID NO:1)] from the first Ig-like domain of rat SC coupled to bovine thyroglobulin. This sequence is identical in mouse and rat, and differs by one amino acid from the human sequence. Several clones were obtained which produce MAbs that recognize human SC but not sIgA, consistent with a recognition site in the region which binds to dimeric IgA (dIgA).

b) Use Of Anti-Human SC Monoclonal Antibodies For Gene Transfer

High-titer monoclonal antibodies which recognize human SC (generated as described above) are tested for their ability to facilitate gene transfer by including Fab fragments prepared from each of them in gene transfer complexes prepared by chemical coupling (as described in the preceding examples). Production of the monoclonal antibodies is scaled up in mouse ascites. Monoclonal antibodies are purified on a Protein A-MAPS column and cleaved with papain to form Fab fragments (the papain is linked to beads for ease of removal). The product is passed again through the Protein A-MAPS column to remove Fc fragments. Purity and yield of the Fab portion is checked by gel electrophoresis (appearance of a 52 kDa band). This Fab portion is reacted with N-succinimidyl 3-(2-pyridyldithio)-proprionate (SPDP; Pierce) according to the manufacturer's instructions, and purified on a gel filtration (e.g., Sephadex G-200) column (alternatively, dialysis may be conducted to remove unreacted SPDP and low molecular weight reaction products). At the same time, poly-L-lysine (10 kDa average molecular weight; Sigma) is reacted with SPDP, and the product cleaved with DTT. The number of SPDP molecules added is monitored during the cleavage step at $OD_{343}$. Provided that an average of <2 SPDP were added per polylysine molecule, the product is reacted with the modified Fab and the reaction is monitored with the release of the chromophore at 343 nm. In addition, the product is examined by gel electrophoresis to demonstrate loss of the 52 kDa band and appearance of a greatly retarded protein in the stacking gel. FPLC is also be used to demonstrate appearance of a new peak.

Alternatively mouse protamine 1, cloned from mouse testes by PCR, utilizing sequences in GenBank, may be used as polycation. Mouse protamine has only a few lysines concentrated at the ends of the molecule (the remainder of the cations are supplied in arginines), so coupling may occur in a much more defined configuration.

This protein portion of the complex will be rendered 0.5M in NaCl, as will twice-CsCl-purified pGL3 (an expression vector encoding luciferase). The protein will be added dropwise to the DNA, with constant vortexing, and then 1M NaCl added until turbidity disappears. The complex is used immediately, after an aliquot is removed for electron microscopy to confirm production of a tight toroid structure.

The complex is tested using MDCK cells (ATCC CRL 6253) which have been transfected with the gene for the human pIgR grown on a porous support (obtained from Dr. C. Kaetzel, Case Western Reserve University School of Medicine, Cleveland, Ohio). These cells are particularly useful because by FACS analysis, 100% of these cells express pIgR and release it predominantly at the apical surface. However, other cells may be employed to study the ability of complexes comprising Fab fragments of anti-human SC monoclonal antibodies to mediate gene transfer. For example, human tracheal epithelial cells in primary culture on collagen gels may be employed [Fiedler et al. (1991) Am J. Physiol 261:L255]; 5–66% of these cells are positive for pIgR. HT29.74 cells induced to express pIgR by growth in glucose-free medium and treatment with interferon-y may also be employed; 10–20% positive of these cells express pIgR.

The condensed monoclonal Fab/polycation/expression vector complexes are added to the basolateral surface of multiple samples of the desired cells (e.g., MDCK cells expressing the pIgR). After 24 hours, the cells are fed and samples are harvested every 24 hour thereafter for 7 days. The cells are lysed and homogenized, and luciferase activity measured as described (above). The antibody giving the greatest gene transfer over a 1 week period is selected.

EXAMPLE 8

Generation Of Chimeric Mouse-Human Monoclonals Directed Against Human SC

In order to reduce the immunogenicity of the anti-pIgR mouse MAbs in humans, yet preserve antigen specificity, murine/human chimeric antibodies are generated. These antibodies contain the variable domain and antigen binding characteristics of mouse origin but utilize the human constant domains, the domains most likely to be immunogenic. Vectors with the genes encoding the four human gamma constant regions and the human kappa gene are used to produce chimeric rodent anti-pIgR MAbs (these vectors are described in Morrison and Oi (1989) Adv. Immunol. 44:76 and Shin and Morrison (1989) Methods Enzymol. 178:459].

a) Production Of Chimeric Mouse/Human Anti-Human SC MAbs

RNA from a hybridoma cell line expressing the rodent anti-pIgR MAb of interest is isolated and reverse transcribed to cDNA using techniques well known in the art. Degenerate primers designed to prime conserved sequences in the framework 1 and constant regions will be used to amplify by PCR the cDNA for the variable regions, $V_H$ and $V_L$, for heavy and light chains respectively. The PCR is conducted using the high-fidelity editing Pfu polymerase (Stratagene) to minimize the introduction of mutations during amplification. The PCR product is then ligated into a pCR II plasmid vector (Invitrogen, San Diego Calif.), and transformed into INVαF' Escherichia coli (Invitrogen).

Transformants harboring the plasmid with the variable region inserts are confirmed by size and restriction analysis. Plasmid DNA obtained from the transformants is isolated by alkaline lysis followed by RNAase and polyethylene glycol precipitation, and then sequenced via dideoxy chain termination using the Sequenase 2.0 DNA sequencing kit (US Biochem, Cleveland Ohio). Several transformants are sequenced so that PCR-induced errors are not propagated. A specific J region primer is then designed based on the sequence information obtained. This new primer allows the elimination of the mouse constant regions in a new PCR product. The $V_H$ and $V_L$ regions are then amplified using new J region and leader region primers as described [Morrison and Oi, supra and Shin and Morrison, supra], and resequenced to ensure that Pfu polymerase-induced mutations are not introduced. The amplified $V_H$ region gene is then ligated into the Morrison expression vectors containing the human gamma 1 constant region genes via NheI and EcoRV restriction sites engineered into the 5' end of the PCR primers. The constant region vectors contain the his gene for future selection.

The gene encoding the mouse $V_L$ region is similarly inserted into the vector containing the gene for human kappa region using SalI and EcoRV restriction sites. Both vectors are then co-transfected into the SP2/0-Ag14 mouse myeloma cell line by electroporation using a BTX 600 electroporator. Cells are grown in selective media (7.5 mM histidinol) for 12 days and then screened by ELISA using plates coated with goat anti-human Ig. Plates are blocked with 1% BSA, washed 3 times, cell supernatant added, washed and then exposed to goat anti-human kappa chain alkaline phosphatase conjugate and the ELISA developed with substrate using standard procedures. Positive controls include human IgG from IVIG (Sandoglobulin) while negative controls include non-chimeric monoclonal antibody from the original hybridoma. The histidinol selects for chimeric heavy chains, and the ELISA identifies clones that also express light chain. Antibody is concentrated and purified from bulk cultures via passage of supernatant over protein A or G columns and Amicon ultrafiltration. Alternatively, the "Micro-mouse" "Cell-pharm" apparatus (UniSyn, Inc, Tustin, Calif.) are employed in which hollow fiber membranes allow antibodies to be trapped and highly concentrated.

After purification, the chimeric antibodies are tested for their ability to bind to antigen (hSC) in ELISA assays and are compared to the original mouse antibodies as well as irrelevant chimeric clones. In addition, the antibodies will be tested in two other ways to insure proper size and structure:

(1) in SDS-PAGE to check molecular size of reduced and unreduced chimeric antibody against murine and human standards. (2) by immunoprecipitation in which cytoplasmic as well as supernatant antibodies will be $^{35}$S labeled and immunoprecipitated with monoclonal and polyclonal antisera.

Once the identity of the product is confirmed and its binding properties are confirmed to approximate the mouse antibody, Fab fragments will be prepared and coupled to polycation, condensed with DNA and tested in using human cells expressing the pIgR (e.g., the MDCK-hSC system described below).

Increased expression of the mouse/human chimeric MAbs may be achieved, if necessary or desirable, as follows. Cell lines that have been cotransfected with mouse variable heavy and light chain genes and with human constant genes as described above and that are producing chimeric antibody, are secondarily transfected with the cytomegalovirus immediate-early gene (CMV iel) that also contains the hygromycin B resistance gene ($Hy^R$). Chimeric antibody-producing cells will be electroporated with 5 μg of pON308 containing the CMV iel DNA together with 5 μg of pY3 containing 5 μg of the $Hy^R$ DNA (Dr. B. Zerler, Miles Research Institute, West Haven, Conn.). Cells will then be grown in 96 well plates after transfection in media containing 400 μg of Hy per ml. Wells containing cells that produce high amounts of antibody as detected by ELISA will be expanded in Hy media, and antibody will then be collected and purified as described above. This strategy is employed when the vectors which contain the NF-kB sequences in the promoter region are used to express the chimeric constructs.

b) Addition Of Sequences Encoding Polycation

To obtain a construct which will contain the recognition sites of the antibody embedded constant region in human as well as the polycation sequences suitable for condensation with plasmid DNA to form the gene transfer complex the following steps are taken. The plasmids which encode the "humanized" monoclonal antibody are used as a template to permit the replacement of sequences in the Fc region of the heavy chain with sequences which encode a polycation.

In order to create DNA sequences encoding polylysine, the following strategy is proposed. Oligomers of the following sequences 5-AAG AAG AAG AAA AAA A-3' (SEQ ID NO:2) and 5'-C TTC TTC TTC TTC TTT TTT-3' (SEQ ID NO:3) are annealed and then oligomerized, and the desired size (210–240 bp) separated and purified by agarose gel electrophoresis. Filling in with dTTP will leave one blunt end and a TT overhang. At the same time, the shuttle vector (any suitable vector such as pCR II) is digested with SmaI, a blunt end cutter, and EcoRI and filled in with dATP, leaving a blunt end and an AA overhang. Vector and insert are ligated, giving a gene encoding polylysine embedded in a multiple cloning site, which can then be excised and cloned into the CH vector via a unique restriction site at the 3' end of the CH2 domain inserted via site-directed mutagenesis. The 3' end of poly-L-lysine will then be connected to the 5' end of the 3' untranslated region.

To create DNA sequences encoding protamine, the gene for mouse protamine 1 is cloned by PCR from mouse testes (see below). Convenient restriction sites can be inserted at the ends by PCR, and the resulting fragment cloned into the heavy chain construct.

Fusion proteins will be purified from cell supernatant using molecular sizing chromatography and a Sepharose G-200 column. Protein A may not be adequate for purification since some of our complexes will contain Fab only and no intact constant domain, and some of the complexes will contain antibodies with altered constant domain due to insertion of the polycation (which could decrease protein A binding). Therefore, the fusion proteins are first purified by affinity chromatography using a column made with SC. Alternatively, fusion proteins are be purified by ion exchange.

The new complex is first tested in an ELISA assay for its ability to recognize hSC presented on an ELISA plate. If the binding affinity has been severely compromised, the complex will be reengineered to alter the relative position of the polycation in order to better preserve the binding site. If its binding affinity is good, the chimeric protein will be condensed with plasmid DNA containing SV40-luciferase sequences to form a gene transfer complex, an aliquot reserved for electron microscopy to assess complex size and compaction, and the complex tested for gene transfer activity.

c) Testing The Chimeric Protein For Its Ability To Effect Gene Transfer

The MDCK-hSC cells described below are used as a test system. The complex will be applied to the basolateral surface of the MDCK-hSC cells and incubated for 24 hr. Cells will be harvested 48, 72, and 96 hours later, lysed, and luciferase activity measured in the cell lysates. Different concentrations of DNA will be applied to obtain a dose-response curve, and lipofection of the same plasmid will be used as a positive control for the ability of these cells to process the luciferase protein (these cells, transfected with SV40 luciferase construct by lipofection, express this reporter gene in robust fashion).

EXAMPLE 9

Production Of Anti-Human SC Single-Chain Antibodies

Chimeric rodent/human MAbs (prepared as described in Example 8) contain the variable domain and antigen binding characteristics of rodent origin but utilize the human constant domains, the domains most likely to be immunogenic. These chimeric MAbs should be less immunogenic when administered to a human than the corresponding Fab fragments isolated from the rodent MAb. To further reduce the potential immunogenicity of antibodies capable of binding to the human pIgR, single-chain antibody molecules (scFvs) directed against human SC (pIgR) were generated. The scFvs generated include scFv alone and scFv as a fusion protein with mouse protamine sequences. The scFv fusion proteins which contain polycation sequences (e.g., protamine) avoid the need to chemically couple a polycation to the antibody used to target DNA to the pIgR.

Single-chain antibodies consist of an antibody light chain variable domain ($V_L$) and heavy chain variable domain ($V_H$) connected by a short peptide linker. The peptide linker allows the structure to assume a conformation which is capable of binding to antigen [Bird et al., (1988) *Science* 242:423 and Huston et al. (1988) *Proc. Natl. Acad. Sci. USA* 85:5879]. Single-chain antibodies directed against cell surface proteins (e.g., transferrin receptor, the p55 subunit of the interleukin 2 receptor) have been used as one portion of a fusion protein with a cytotoxin (e.g., Pseudomonas exotoxin A or diphtheria toxin) [Batra et al. (1991) *Mol. Cell. Biol.* 11:2200; Chaudhary et al. (1989) *Nature* 339:394; Chaudhary et al. (1990) *Proc. Natl. Acad. Sci. USA* 87:949; Pantoliano et al. (1991) *Biochem.* 30:10118]. These fusion proteins kill only those cells which express the appropriate receptor, and some are up to 750 times more potent than their congeners assembled from the components by chemical means [Batra et al. (1991), supra; and Chaudhary et al. (1989) Nature, supra]. This improvement in efficiency occurs despite a loss of 2–10 fold in binding efficiency of the Fv compared to native antibody from which it was derived. Presumably the poorer affinity of the Fv is compensated by less distortion of the binding site in the course of the chemical coupling.

Because the first and third complementarity determining regions (CDRs) of rearranged immunoglobulin genes are flanked by conserved sequences, it is possible to design PCR primers capable of amplifying cDNA for the variable regions from hybridoma mRNA without any specific knowledge of the nucleotide sequence of that specific antibody. Nicholls et al. describe a set of six $V_L$ specific primers and four $V_H$ specific primers [*J. Immunological Methods* (1993) 165:81]. Any variable region will have a maximum of three mismatches with the most homologous primers. The cloning of the $V_L$ and $V_H$ domains from hybridoma cell lines expressing rodent anti-human SC MAbs and the linking of these two domains by a $(GGGGS)_3$ linker is described in detail below.

a) Generation Of Anti-Human SC Single-Chain Fv i) Cloning Of $V_L$ And $V_H$ Regions RNA was extracted from hybridoma cells expressing the antibody of interest (e.g., hybridomas 4121 and 4114) using guanidinium isothiocynate and was reverse transcribed into cDNA by Moloney murine leukemia virus reverse transcriptase using random hexamers as primers. As described by Nicholls et al. (supra), the resulting cDNA was screened by PCR with ten sets of primer pairs to determine from which Kabat family the heavy and light chain variable genes were derived [Kabat et al. (1991) *Sequences of Proteins of Immunologic Interest*, 5th edn., U.S. Public Health Service, Bethesda, Md.]. The Nicholls primers are (the UNI primers are used to partner with each of the other primers in a set):

For anti-human SC clone 4121, the variable light chain was amplified most effectively by family Vb primers ($V_L$-Vb and $C_L$-UNI), and the variable heavy chain was amplified most effectively by family V primers ($V_H$-V and $C_H$-UNI). The following new primers were then designed to incorporate convenient restriction sites, start and stop codons, and sequences encoding the linker region:

Primer 1 (5' VL): 5'-GGC CCA AGC TTG CCA CCA TGG ACA TTG TGC TG-3' (SEQ ID NO:16). Primer 1 includes a HindIII site for cloning, a Kozak consensus start site (bold), and the original Nicholls $V_L$-Vb sequences (underlined).

Primer 2 (3' VL): 5'-ACC GGA TCC GCC ACC GCC CGA GCC ACC GCC TCC TTT TAT CTC CAG CTT TGT GCC-3' (SEQ ID NO:17). Primer 2 includes the original Nicholls $C_L$-UNI primer sequences (underlined) and sequences encoding the first 11 amino acids of the desired linker region (GGGGSGGGGSG) (SEQ ID NO:18). Twenty-one bases (double underlined) present in Primer 2 overlap with 21 bases in Primer 3 so that the products may be spliced together by overlap extension and PCR [e.g., using the PCR techniques known as gene splicing by overlap extension (SOE); Johnson and Bird (1991) *Methods in Enzymol.* 203:88].

Primer 3 (5' VH): 5'-TCG GGC GGT GGC GGA TCC GGT GGC GGC GGC TCT GAG GTT CAG CTT CAG CAG TCT-3' (SEQ ID NO:19). Primer 3 includes the original Nicholls VH-V primer sequences (underlined) as well as sequences encoding last 11 amino acids of linker (SGGGGSGGGGS) (SEQ ID NO:20), including 21 bases that overlap with Primer 2 (double underlined).

Primer 4 (3' VH): 5'-CCT AGT CTA GAC TTA CAT CGA TGA GGA GAC TGT GAG AGT GGT GCC-3' (SEQ ID NO:21). Primer 4 includes 24 bases of the original Nicholls $C_H$-UNI primer sequences (underlined), a stop codon, a ClaI site upstream of the stop codon, and an XbaI site downstream from the stop codon.

| $V_L$ Primers: | | |
|---|---|---|
| $V_L$-I/III | 5'-GAC ATT GTG ATG ACY CAY TCT-3' | SEQ ID NO:4 |
| $V_L$-IV/VI | 5'-CAA AWT GTK CTC ACC CAG TCT-3' | SEQ ID NO:5 |
| $V_L$-IIa | 5'-GAT GTT KTG ATG ACC CAA ACT-3' | SEQ ID NO:6 |
| $V_L$-IIb | 5'-GAT ATT GTG ATA ACC CAG GMT-3' | SEQ ID NO:7 |
| $V_L$-Va | 5'-GAC ATC SAG ATG ACY CAG TCT-3' | SEQ ID NO:8 |
| $V_L$-Vb | 5'-GAY-ATT GTG MTG ACM CAG TCT-3' | SEQ ID NO:9 |
| $C_L$-UNI | 5'-TTT TAT CTC CAG CTT KGT SCC-3' | SEQ ID NO:10 |

| $V_H$ Primers: | | |
|---|---|---|
| $V_H$-I | 5'-CAG GTG CAG CTK MAG GAG TCA-3' | SEQ ID NO:11 |
| $V_H$-II | 5'-CAG GTC CAR CTG CAG CAG YCT-3' | SEQ ID NO:12 |
| $V_H$-III | 5'-GAR GTG AAG CTG GTC GAR TCT-3' | SEQ ID NO:13 |
| $V_H$-V | 5'-GAG GTT CAG CTT CAG CAG TCT-3' | SEQ ID NO:14 |
| $C_H$-UNI | 5'-TCA GGA GAC TGT GAG AGT GGT GCC TTG RCC CCA-3' | SEQ ID NO:15 |

Where: M = A or C, R = A or G, W = A or T, S = C or G, Y = C or T and K = G or T
(Nicholls et al., supra).

ii) Assembly Of Single-Chain Fv

Clone 4121 $V_L$ was re-amplified by PCR using Primers 1 and 2. $V_H$ was re-amplified using Primers 3 and 4. Both products were gel-purified and then spliced together by overlap extension and PCR using Primers 1 and 4 [Johnson and Bird (1991), supra]. A product of the appropriate size (approx. 750 bp) was generated and sequenced.

The single-chain Fv construct (as a HindIII-XbaI fragment) was subcloned into pRC/CMV (Invitrogen) which had been digested with HindIII and XbaI sites. The resulting construct was termed pRC/CMV-4121 scFv.

iii) Cloning Of Mouse Protamine 1 cDNA And Construction Of A 4121 Single-Chain Fv/Protamine Fusion The cDNA sequence for mouse protamine 1 was obtained from Genbank [Johnson et al. (1988) *Biochem. Biophys. Acta* 950:45]. The following primers were designed to amplify the mouse protamine 1 cDNA while incorporating convenient restriction sites onto either end:

Primer 5: 5'-GAC CCA TCG ATG GCC AGA TAC CGA TGC TGC-3' (SEQ ID NO:22); the ClaI site is indicated by underlining.

Primer 6: CCT AGT CTA GAT AAG CTT CTA GTA TTT TTT ACA CCT TAT-3' (SEQ ID NO:23); Primer 6 contains HindIII and XbaI sites (underlined) downstream from stop codon.

RNA was extracted from mouse testes and was reversed transcribed into cDNA by Moloney murine leukemia virus reverse transcriptase using random hexamers as primers. The protamine cDNA was then amplified by PCR using Primers 5 and 6. The resulting PCR product was digested with ClaI and XbaI and was subcloned into pRC/CMV-4121 scFv which had been digested with ClaI and XbaI to generate the fusion construct. The fusion construct was termed pRC/CMV-4121 scFv/protamine. The DNA sequences encoding the anti-human SC single-chain Fv/protamine fusion protein are listed in SEQ ID NO:24. The amino acid sequence of the anti-human SC single-chain Fv/protamine fusion protein is listed in SEQ ID NO:25.

Analysis of the DNA sequence encoding the single-chain Fv protein revealed that a single codon for glycine located within the linker region had been dropped during the assembly of the single-chain Fv. The resulting single-chain Fv contains a linker having the amino acid sequence GGGGSGGGGSGGGS (SEQ ID NO:26) instead of the intended (GGGGS)$_3$ (SEQ ID NO:27). The linker region in a single-chain Fv is reported to require a length of 3.5Å or greater (3.5Å being the distance between the light and heavy chain variable regions in native antibodies as determined by crystal structure) [Huston et al. (1988) *Proc. Natl. Acad. Sci. USA* 85:5879]. As each peptide bond is 0.38Å in length, the 14 amino acid linker present in the anti-human SC single-chain Fv would more than satisfy the linker length requirement reported by Huston et al. Pantoliano et al. reported that the affinity of the single-chain Fv is reduced when the linker is only 12 amino acids in length but that lengths between 14 and 25 amino acids show similar binding affinity to the target protein [Biochem. (1991) 30:10117]. The 4121 single-chain Fv containing the 14 residue linker has been shown to recognize the receptor protein by "Western blot" type analysis (described below).

DNA encoding the single-chain Fv and the single-chain Fv/protamine fusion directed against human SC was cloned into pBluescript (Stratagene) and expressed in the TnT® rabbit reticulocyte lysate expression system (Promega) in the presence of $^{35}$S-methionine. Translation of the 4121 single-chain Fv yielded a protein of about 30 kDa, the expected size. Translation of the 4121 fusion protein yielded a broad band about 56 kDa, probably because of the highly basic nature of protamine (pK1 about 12) moving in a gel having a pH of 8.8.

The labelled reticulocyte lysate (programmed with the 4121 single-chain Fv) was then incubated with a nylon membrane onto which had been transferred proteins from clarified human milk separated by gel electrophoresis. The blot was extensively washed and developed by autoradiography. This radioactive protein bound to a protein in human milk of the appropriate molecular weight for human SC. These results demonstrate that 4121 single-chain Fv containing the 14 residue linker recognizes the receptor protein (human SC).

iv) Expression Of Single-Chain Fv And Single-Chain Fv Fusion Proteins

DNA sequences encoding the single-chain Fv and single-chain Fv fusion proteins are expressed in *E. coli* cells by insertion of the coding region into the QIAexpress expression system (Qiagen, Chatsworth, Calif.). In this system, expression is under the tight control of the *E. coli* phage T5 promoter and two lac operator sequences which minimizes "leaky" expression prior to induction by IPTG. In addition, these expression vectors also encode a 6-histidine tag to facilitate purification on a Ni-NTA column. This advantageously allows tight binding of the expressed protein to the column (Kd at pH 8.0 is $10^{-13}$) which facilitates removal of bacterial nucleic acid which may bind to the polycation sequences present on the single-chain Fv fusion proteins. The fusion construct will be assembled with the 6-His at the N terminus and the polycation at the C terminus to minimize destabilization of the 6-His interaction by the highly charged polycation. Other suitable and equivalent expression systems are known to the art.

Expression of the single-chain Fv and single chain Fv fusion proteins may be achieved in eukaryotic cells [e.g., COS-7 (ATCC CRL 1651), myeloma cell lines, and HEK293 cells (ATCC CRL 1573)]. To permit expression of these proteins in eukaryotic cells, leader sequences are added to the proteins to assure that the proteins are secreted (thereby improving ease of purification). The leader sequences may be added, or the immunoglobulin sequences upstream of the Nicholls primers may simply be included.

Following expression and purification of the single-chain Fv and single-chain Fv fusion proteins, these proteins are condensed with the desired expression vector to form a gene transfer complex. An aliquot is examined by electron microscopy to assess complex size and compaction and the complex is tested for gene transfer activity.

EXAMPLE 10

Construction Of A Peptide-Polycation Carrier For The Targeted Delivery Of Genes Via The Serpin Enzyme Complex Receptor The serine protease inhibitor (serpin) enzyme complex receptor (SEC-R) is found on a variety of cell types, including hepatoma cells, mononuclear phagocytes, the human neutrophil cell lines U937 and HL-60, the human intestinal epithelial cell line CaCo2, mouse fibroblast L cells, rat neuronal cell line PC12, and the human glial cell line U373MG [Perlmutter (1994) *Pediatric Res.* 36:271–277]. This receptor binds to a region of serine protease inhibitors which is exposed by the proteolytic digestion of the serpin by its enzyme ligand with formation of a serpin/serine protease complex [Enghild, el al. (1994) *J. Biol. Chem.* 269:20159–20166; Perlmutter, et al. (1990) *J. Biol. Chem.*

265:16713–16716; Perlmutter, et al. (1990) *Proc. Natl. Acad. Sci. USA* 87:3753–3757; Kahalil, et al. (1994) *Brain Res.* 651:227–235; Joslin, et al. (1991) *J. Biol. Chem.* 266:11282–11288; Joslin, et al. (1993) *J. Biol. Chem.* 268:1886–1893]. Following binding, the serpin-enzyme complex is internalized and routed to the lysosomes for degradation. Synthetic peptides, based in sequence on amino acids 359–374 of $\alpha_1$-antiprotease, bind in a specific and saturable fashion to the receptor on HepG2 cells and mediate a functional response [Perlmutter, et al. (1990) *J. Biol. Chem.*, supra; Perlmutter, et al. (1990) *Proc. Natl. Acad. Sci. USA*, supra; Kahalil, et al. (1994), supra; Joslin, et al. (1991), supra; Joslin, et al. (1993), supra]. The receptor also binds amyloid-β peptide, substance P, and bombesin [Joslin, et al. (1991) *J. Biol. Chem.* 266:21897–21902; Boland, et al. (1995) *J. Biol. Chem.* 270:28022–28028]. Thus, like other receptors described in the preceding examples which are favorable for gene transfer, the SEC-R is adapted for binding and internalizing large molecular complexes with low selectivity as long as a pentapeptide binding domain [FVF/YLI (SEQ ID NOS:28 and 29)] is present [Perlmutter (1994) *Pediatric Res.* 36:271; Kahalil, et al. (1994), supra; Joslin, et al. (1991), supra; Joslin, et al. (1993), supra and Bu et al. (1992) J. Biol. Chem. 267:15595].

The following examples demonstrate that exogenous DNA complexes bearing the pentapeptide binding motif can be targeted to and internalized by the SEC receptor. Its abundance and bulk flow characteristics coupled to the prospect of targeting hepatocytes (the site of many inherited disorders) as well as cells primarily affected by Alzheimer's disease, and $\alpha_1$-antiprotease deficiency [reviewed in Perlmutter (1994) *Pediatric Res.*, supra], make this receptor system an attractive candidate for receptor-mediated gene delivery. Furthermore, its presence in the brain may provide the potential to transfer therapeutic genes across the blood-brain barrier. In this example a carrier comprising poly-L-lysine coupled to a synthetic peptide ligand for the SEC receptor was constructed. Foreign DNA condensed by the poly-L-lysine on the carrier can be targeted to and expressed in cells bearing the receptor.

a) Generation Of Peptides Containing The Pentapeptide SEC-R Binding Motif

Peptides C105Y [CSIPPEVKFNKPFVYLI (SEQ ID NO:30)] and C1315 [CFLEAIPMSIPPEVKFNKPFVFLIIHRD (SEQ ID NO:31)] were synthesized by solid phase methods, purified, and subjected to amino acid composition and sequence analysis as described previously [Joslin, et al. (1991) *J. Biol. Chem.* 268:1886–1893]; the pentapeptide recognition sequence is indicated by bold type. The pentapeptide binding domain is indicated by the bold letters in each sequence. The C105Y peptide was used to quantitate the amount of SEC-R present on the surface of cultured cell lines. The C1315 peptide was conjugated to polylysine to form a carrier capable of delivering DNA to cells expressing the SEC-R.

b) Formation Of C1315-Polylysine Conjugates

The C1315 peptide was covalently linked to poly-L-lysine (average $M_r$=22.5 kD; Sigma) using the heterobifunctional cross-linking reagent LC sulfo SPDP (Pierce) as described in Example 3 above [see also, Ferkoll et al. (1993) *J. Clin. Invest.* 92:2394]. Briefly, 77 µl of 20 mM LC sulfo SPDP in water were incubated with 3 mg poly-L-lysine (10 fold molar excess of LC sulfo SPDP to polylysine) in 0.1M phosphate buffered saline (PBS), pH 7.4, at room temperature (about 22° C.) for 30 minutes. The reaction mixture was then dialyzed exhaustively water to remove unreacted LC sulfo SPDP and low molecular weight reaction products. A three fold molar excess of modified poly-L-lysine was then added to peptide C1315 and the reaction allowed to go to completion at 22° C. for 24 h. The conjugate was dialyzed to remove unreacted peptide and low molecular weight reaction products.

c) NMR Analysis Of The C1315-Polylysine Conjugate

Construction of the protein conjugate of poly-L-lysine to C1315 peptide was monitored by NMR, both at the step of LC sulfo SPDP modification of polylysine, and at the step of conjugation of the C1315 peptide to modified polylysine. An aliquot (5–10 mg) of the conjugate was exhaustively dialyzed against water, lyophilized from water and subsequently from $D_2O$ then resuspended in 99.999% $D_2O$ (Merck). Samples were then loaded onto a NMR spectrometer (Varian Unity Plus 600) and spectra were obtained between 0.5 and 16 hrs. Chemical shifts were referenced to the residual HDO resonance at 4.9 ppm. Representative NMR spectra are shown in FIG. 21.

FIG. 21 A shows the spectrum obtained from unmodified polylysine; FIG. 21B shows the spectrum obtained from LC sulfo SPDP-conjugated polylysine; FIG. 21C shows the spectrum obtained from LC sulfo SPDP-conjugated polylysine following treatment with DTT; and FIG. 21D shows the spectrum obtained from LC sulfo SPDP-conjugated polylysine complexed with the C1315 peptide.

Figure 21B:
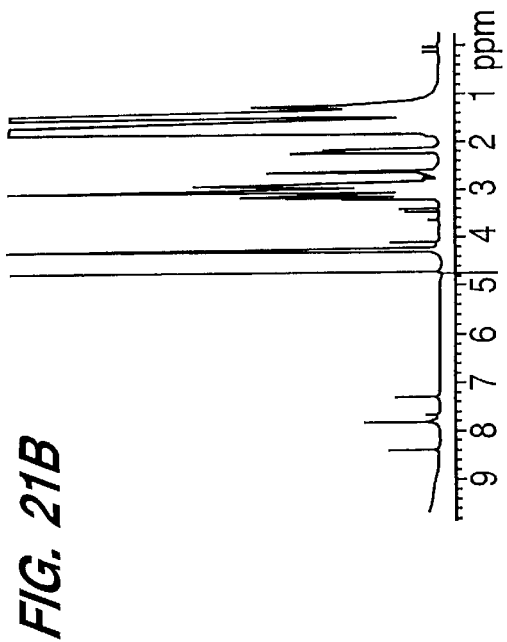
Figure 21D:
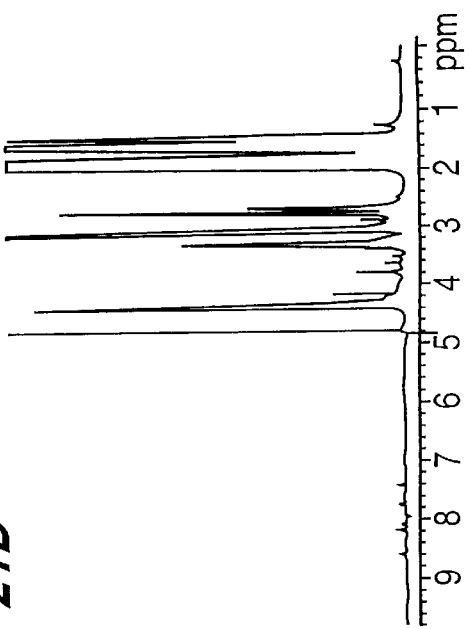
Figure 21A:
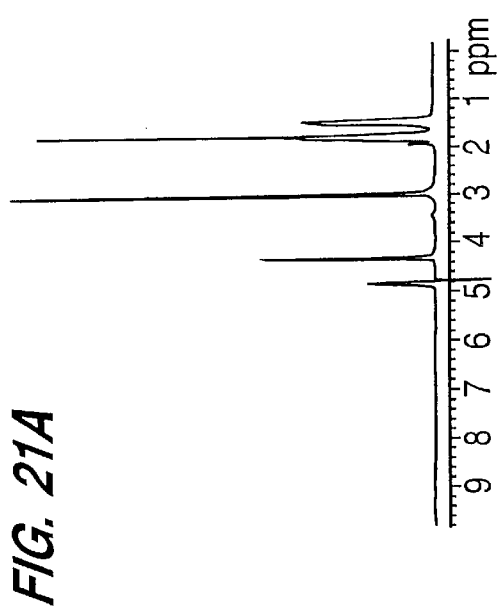
Figure 21C:
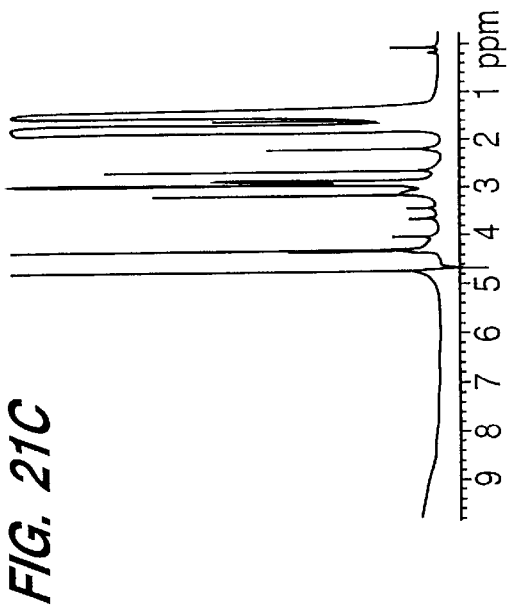

The spectrum for unmodified polylysine (FIG. 21A) serves as a "background" control for the conjugation reactions. Lysine hydrogens are less deshielded than aromatic hydrogens and thus have low resonance shifts ($\alpha$H: 4.25 ppm, βH: 1.87 ppm, γH: 1.46 ppm, δH: 1.79 ppm, ΣH: 3.07 ppm). The aromatic hydrogens on LC sulfo SPDP, however, are more deshielded, with chemical shifts at higher ppm. To assess linker binding to the primary amine side chain of lysine, a spectrum for LC sulfo SPDP modified polylysine was obtained (FIG. 21B). Hydrogen chemical shifts at 7.36 ppm, 7.88 ppm, and 8.45 ppm belonged to the 1, 2 and 3, and 4 hydrogens of the SPDP aromatic ring. Furthermore, treatment of the polylysine/LC sulfo SPDP with dithiothreitol cleaved the ring and resulted the disappearance of 98.8% the aromatic hydrogen shifts (FIG. 21C). This maneuver also demonstrated that dialysis is efficient in removing SPDP and low molecular weight products from the solution. Thus, the NMR spectrum represents only materials covalently bound to polylysine. Integration of the lysine as well as the SPDP aromatic hydrogens' peaks revealed that 1 in 14 lysines reacted and bound to LC sulfo SPDP. Based on the molar ratios of polylysine to LC sulfo SPDP during the coupling reaction, it was estimated that this reaction was 75% efficient. $H^1$NMR analysis of the C1315/polylysine conjugate, shown in FIG. 21D, confirmed our expectations of the appearance of the aromatic phenylalanine and histidine hydrogen shifts concurrent with the disappearance of the LC sulfo SPDP aromatic protons. Phenylalanine aromatic hydrogens shifted at 7.25 to 7.60 ppm (labeled in FIG. 21D). Integration of these peaks revealed that 1 in 159 lysines and 1 in 11.4 LC sulfo SPDP linkers were linked to the peptide. Based on molar ratios described in the methods section, this reaction was 85% efficient (e.g., 85% of added peptide C1315 was conjugated to polylysine).

EXAMPLE 11

Formation Of C1315 Peptide-Based DNA Complexes

Complexes comprising the C1315 peptide/polylysine conjugate and several different expression vectors were generated. The DNA comprising the expression vector was condensed by the peptide based carrier into highly compact complexes suitable for efficient internalization via an endocytic pathway (e.g., via uptake and internalization through the SEC-R).

a) Reporter Genes And Plasmid Preparation

Three plasmids coding for three different reporter genes were used. The expression plasmid pGL3 (Promega) contained the simian virus (SV40) viral promoter and enhancer ligated to the *Photinus pyralis* luciferase gene and inserted into the *E. coli* pUC19 vector. The plasmids pCMV lac Z II [Lin and Culp (1991) *Biotechniques* 11:344–351] and pFIX (Dr. E. Davie, University of Washington, Seattle;available from Immune Response, San Diego, Calif.) contain the cytomegalovirus (CMV) promoter ligated to the *E. coli* β-galactosidase (lac Z) and the human factor IX (hFIX) genes, respectively. The plasmids were grown in *E. coli* strain DH5α, extracted, and purified twice on a cesium chloride density gradient [Sambrook et al. (1989) Molecular Cloning: *A Laboratory Manual*, 2nd Ed., Cold Spring Harbor Laboratory Press, Cold Spring Harbor, N.Y.]. Identity of the plasmids was confirmed by restriction endonuclease digestion, and purity was established by electrophoresis on a 1.0% agarose gel. The sizes of the plasmids were as follows: pGL3, 5.6 Kb; pCMV lac Z, 10.8 Kb; pFIX, 5.4 Kb.

The purity of the DNA is important to permit proper condensation of the DNA. In particular, the plasmid DNA is preferably free of bacterial RNA and proteins. Plasmid DNA is purified twice on a CsCl density gradient followed by extraction with phenol:chloroform and digestion twice with RNAses A+T1. The absorbance of a solution containing the purified plasmid DNA is measured at 260 nm and 280 nm and the ratio between the readings at 260 nm and 280 nm ($OD_{260}/OD_{280}$) is preferably about 1.8. The absence of contaminating RNA is confirmed by running an aliquot of the purified plasmid DNA preparation on an agarose gel followed by staining with EtBr. The lack of fluorescent species having a MW lower than that of the plasmid DNA indicates that the contaminating RNA has been removed.

b) Formation Of The C1315 Peptide-Based DNA Complexes

The carrier DNA complexes were formed using general techniques previously described for the galactosylated polylysine ligand in Example 1 above. Briefly, the DNA was condensed by the slow addition (5 μl over 5 min.) of the C1315 peptide carrier in the presence of 400 mM sodium chloride under constant vortexing at room temperature. An IKA VIBRAX-VXR 51 vortex mixer (IKA Labortechnik Staufen) was employed; the vortex mixer is used at speeds up to 1200 rpm. The speed employed depends upon the volume of solution present in the tube. For volumes which represent about ½ the capacity of the vessel (e.g., a microcentrifuge tube), a speed of about 1000 to 1200 rpm is employed (the speed cannot be so great as to permit the solution to escape from the tube); when very small volumes (e.g., about 10 μl in a 500 μl microcentrifuge tube) are used, speeds of 200 to 300 rpm are sufficient to allow mixing.

The amount of carrier added was calculated by the amount of charge on poly-L-lysine required to neutralize the negative charge on the phosphate groups of DNA. After the addition of the carrier to the DNA and the appearance of aggregates, the sodium chloride concentration in the solution was adjusted by the addition of small aliquots of 5M NaCl. With the rise in ionic strength of the solution, the aggregated C1315/poly-L-lysine-DNA complexes assumed a condensed state, and the turbidity of the solution cleared as described in Example 1.

The final volume of the solutions was typically 500 μl, containing a mixture of 1:0.45 wt/wt DNA to peptide/poly-L-lysine conjugate ratio in 0.8–1M NaCl. The different final concentrations of sodium chloride required were due to minor differences, between preparations, in DNA and poly-L-lysine size and physical state. An aliquot of the reaction mixture was examined under the electron microscope (EM) to assess condensation.

c) Electron Microscopy Of The Condensed DNA Complexes

Micro-graph grids were prepared as described in the description of FIG. 1 above. Briefly, immediately after formation of the DNA complexes, a drop of a solution (1:10 dilution of complex mixture in water) was added to a 1,000-mesh electron microscope carbon grid, blotted, and stained with 0.04% uranyl acetate. The samples were then shadowed using rotary shadowing and examined using a JEOL-100C electron microscope.

d) Electron Microscope Analysis Of The C1315 Peptide Based Carrier-DNA Complexes Since tightly condensed particles apparently increase the efficiency of internalization, the C1315 peptide based carrier-DNA complexes were examined by electron microscopy. Typically, C1315/polylysine-pGL3 DNA (5.5 Kb) complex mixtures contained complexes between 17 and 23 nm in diameter. Solutions used to make the complexes were also examined to ensure the absence of artifacts, and contained no visible structures. "Shadows" bordering the complexes, indicate a proportional height dimension to these complexes. Aggregated complexes were present in solution prior to the addition of 5M NaCl. Final complex mixtures contained less than 0.5% of these aggregates. Mixtures that contained greater than 50% of the aggregated form failed to transfect HuH7, HepG2 (high) or HepG2 (low) cells (transfection protocol described below). These data correlated with previous reports showing that only tightly formed complexes transfect cells efficiently [see preceding examples and Ferkol et al. (1996) *Proc. Natl. Acad. Sci. USA* 93:101]. Because plasmid size might affect the size of these particles, the pCMV lac Z II DNA (10.8 Kb), and C1315/polylysine-pCMV Lac Z II complexes were compared. These complexes also ranged in size from 20 to 25 nm in diameter. Complexes with pFIX (5.4 Kb) were identical to pGL3 complexes in size.

EXAMPLE 12

Gene Transfer Into Cells Expressing the SEC Receptor Using C1315 Peptide-Polylysine-DNA Complexes C1315 peptide-polylysine-DNA complexes were used to transfect human hepatoma cell lines which expressed various levels of the SEC receptor on the cell surface.

a) Cell Culture

Two populations of HepG2 cells were maintained as previously described [Perlmutter et al. (1990) J. Biol. Chem. 265:16713]. Briefly, the HepG2 cell lines were maintained in EMEM with L-glutamine (GibcoBRL) containing 10% FCS. HepG2 (high) cells (passage #2) were obtained from ATCC (Rockville, Md.). HepG2 (low) cell (passage #300) were obtained from Dr. Lucyndia Marino (Cleveland, Ohio). These cells were designated (high) or (low) based on their ability to bind SEC receptor ligands C105Y and C1315 (see below). HuH7 cells (Immune Response, San Deigo, Calif.) were cultured in RPMI medium (GibcoBRL) containing 10% FCS. Fresh medium was added every second day.

b) Determination Of Cell Surface SEC Receptor Binding

Peptide C105Y was radio-iodinated by a modification of the chloramine T method [Hunter and Greenwood (1962) Nature 194:49] as follows. Briefly, approximately 50 μg of the C105Y peptide in 20 μl PBS was mixed with 20 μl chloramine T (120 mg/10 ml) and 1 mCi $^{125}$I (DuPont-New England Nuclear, Boston, Mass.). The reaction mixture was incubated for 30 seconds at room temperature and then 50 μl of sodium metabisulfite (36 mg/10 ml) was added. The labeled C105Y peptide was purified on a Sephadex G10 column (Bio-Rad) which had been blocked by application of 3 mg/ml BSA in PBS prior to the addition of the iodinated peptide. The specific radioactivity of $^{125}$I peptide C105Y ranged between 3,500 and 11,700 dpm/ng.

HuH7 cells and two populations of HepG2 cells were studied. Cells were plated in 24 well tissue culture plates, allowed to become confluent, then thoroughly washed with phosphate-buffered saline containing 1 mM $CaCl_2$ and 2.5 mM $MgCl_2$ ($Ca^{2+}/Mg^{2+}$ PBS) and incubated at 4° C. for 2 h with $^{125}$I-labeled ligand (e.g., C105Y) at concentrations of 12.5 to 400 nM in the absence or presence of 200 fold excess unlabeled ligand and diluted in binding medium (DMEM containing 50 mM HEPES, 0.1 mg/ml cytochrome c, 0.01% Tween 80, 2 mg/ml bovine serum albumin). The cells were then rinsed in $Ca^{2+}$ $Mg^{2+}$ PBS, homogenized in 1 N NaOH, and cell-associated radioactivity determined. Non-specific binding was determined by incubating cells with a 200 fold molar excess of cold ligand. Specific binding was defined as the difference between total and non-specific binding. Binding parameters were determined by Scatchard analysis. Binding assays were performed on all three cell lines [HuH7, HepG2 (high), and HepG2 (low)] simultaneously with the same batch of iodinated C105Y peptide so that the proper comparisons could be made.

c) Determination Of Surface SEC Receptor Binding In Cultured Hepatoma Cells

HuH7, HepG2 (high) and HepG2 (low) cells were incubated with different concentrations of $^{125}$I labeled C105Y peptide in the presence and absence of a 200-fold molar excess of unlabeled peptide. The results are summarized in FIG. 22; the results are representative of 6 individual experiments.

Figure 22:
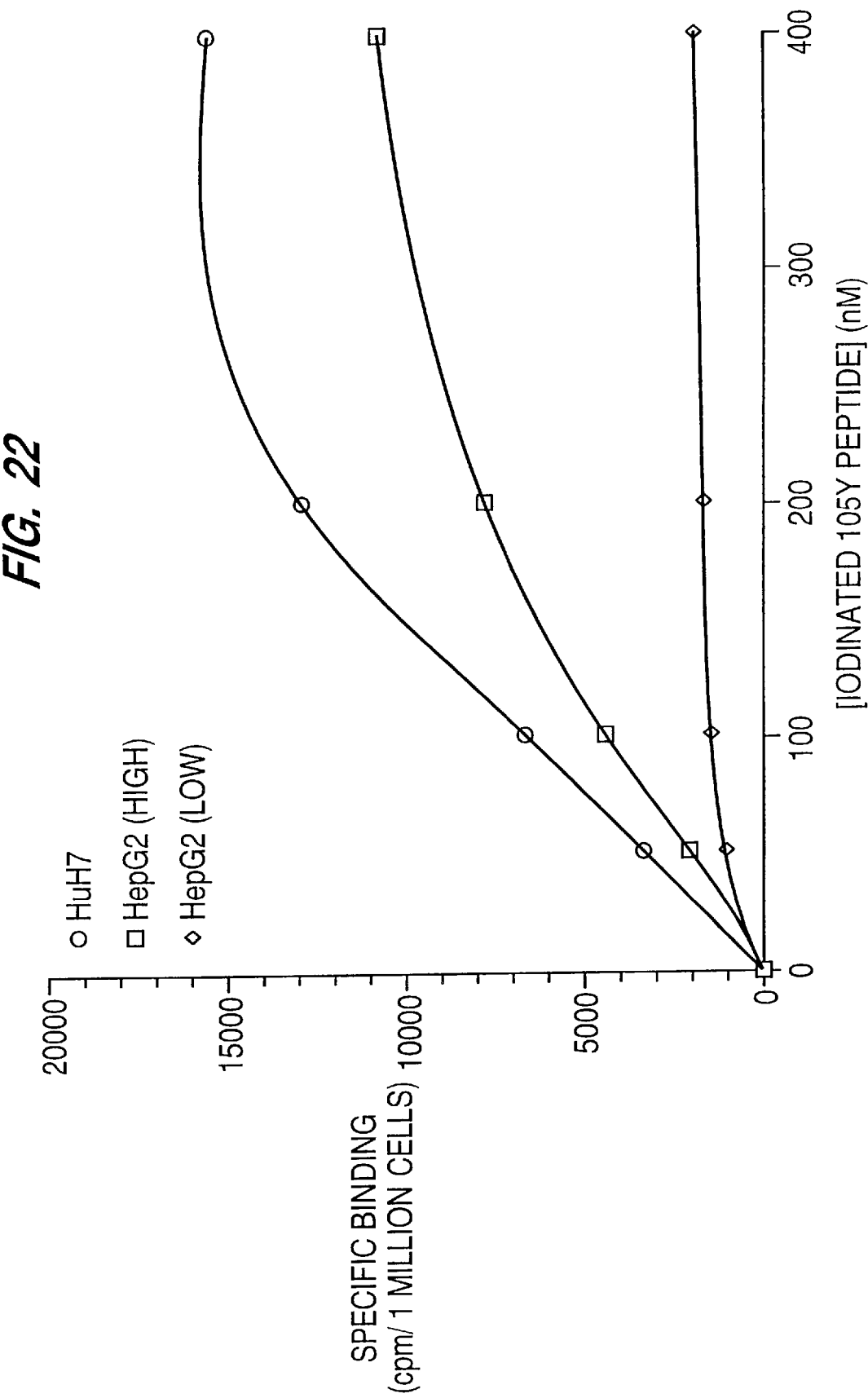

In FIG. 22, the specific binding (expressed as cpm/one million cells) is plotted against the concentration of iodinated C105Y ppeptide (nM). Traces are shown for the specific binding of $^{125}$I-C105Y to HuH7 cells (○), HepG2 (high) cells (□) and HepG2 (low) cells (◇). Specific binding was determined by subtracting the cpm obtained from binding C105Y$^{125}$I (total binding) from the cpm obtained by binding $^{125}$I-C105Y in the presence of a 200-fold excess of unlabelled peptide (non-specific binding).

Both HuH7 and HepG2 (high) cells exhibited specific and saturable binding, shown in FIG. 22 (circles, and squares respectively). Scatchard analysis of HepG2 (high) binding revealed a $K_d$ of 50 nM, consistent with previous reports [Perlmutter, et al. (1990) J. Biol. Chem. 265:16713; Perlmutter et al. (1990) Proc. Natl. Acad Sci. USA 87:3753; Kahalil, et al. (1994) Brain Res. 651:227; Joslin, et al. (1991) J. Biol. Chem. 266:11282; and Joslin, et aL (1993) J. Biol. Chem. 268:1886]. HuH7 cells bound more C105Y [1.5 fold more than HepG2 (high)] with a $K_d$ of about 70 nM. HepG2 (low) cells exhibited 10 fold less specific binding of iodinated ligand than HuH7 cells and 7.5 fold less than HepG2 (high) cells (FIG. 22, diamonds). HepG2 (low) cells bound iodinated C105Y with a $K_d$ of about 22.5 nM. These binding trends were consistent in seven experiments which compared binding in HuH7, HepG2 (high), and HepG2 (low) cells.

d) DNA Delivery To HuH7 And HepG2 Cells In Culture

C1315 peptide/poly-L-lysine-DNA complexes were used to transfect HuH7 and HepG2 cells. Cells were transfected with complexes containing pGL3, pCMV lac Z II and pFIX as follows. Two days before transfection, the HuH7 or HepG2 cells were washed twice with PBS, pH 7.4, trypsinized with 0.05% trypsin in DMEM, and plated in six well plates in serum DMEM containing with glutamine. The cells were allowed to adhere to the plate and become 30% confluent. Cell density was typically $5 \times 10^5$ cells per plate at the time of transfection. On the day of transfection, the growth medium was changed and the cells were washed with $Ca^{2+}/Mg^{2+}$ PBS. Aliquots containing C1315 peptide/poly-L-lysine-DNA complex (0.83, 1.11, or 1.34 pmol pGL3, pFIX (except 1.34 pmol), or pCMV lac Z II DNA condensed with 62 (122 for lac Z II), 80 (160 for lac Z II), or 97 (194 for lac Z II) pmol C1315/polylysine conjugate, respectively) were added to 2 mL of media in individual wells.

The following controls were included: 1) HuH7 or HepG2 (high) cells transfected with 1.11 pmol pGL3, pFIX, or pCMV lac ZII DNA condensed with 80 (160 for lac ZII) pmol unconjugated polylysine in the presence of 80 (160 for lac ZII) pmol C1315 peptide and 200 (400 for lac ZII) pmol LC sulfo SPDP linker; 2) HepG2 (low) cells transfected with 1.11 pmol pGL3 or pCMV lac Z II DNA condensed with 80 or 160 pmol C1315/polylysine conjugate, respectively; 3) HepG2 (high), HepG2 (low), or HuH7 cells transfected with 1.0 pmol of pGL3, pFIX, or pCMV lac Z II DNA by lipofection using Lipofectin® reagent according to the manufacturer's instructions (Life Technologies); and 4) HepG2 (high), HepG2 (low) or HuH7 cells transfected with 1.11 pmol of polylysine condensed DNA by Lipofectin®. Controls 1 and 2 were designed to test for non-specific uptake; controls 3 and 4 were designed to confirm that target cells could express the transgene if delivered.

After addition of the complex and/or Lipofectin®, all cells were incubated at 37° C. for six hours. Cells were then rinsed with $Ca^{2+}/Mg^{2+}$ PBS and fresh growth media added and incubated at 37° C. (with a change of media every 2 days) until the appropriate functional assay was performed. Competition experiments were conducted by transfecting HepG2 (high) cells with 1.11 pmol C1 315 carrier condensed DNA in the presence and absence of a 10 fold excess free C1315 peptide. All transfections were done in duplicate. No cell death was observed in any of the wells transfected with the DNA/conjugated polylysine complexes throughout the incubation.

Luciferase expression was assessed at 2, 4, 6, 8, 10, and 12 days after transfection. lac Z staining was done 36 hours after transfection. Media from cells transfected with pFIX were assayed for human Factor IX activity 4 days after transfection.

i) Assay For Luciferase Expression

Cells were harvested on days 2, 4, 6, 8, 10, and 12 after transfection with complexes containing pGL3, homogenized in lysis buffer (Promega), and incubated for 15 min. Lysates were then centrifuged (12,000× g for 5 min at 4° C.) to pellet cell debris and the supernatant collected for assay. Luciferase activity was measured using Promega assay reagents according to the manufacturer's instructions. 20 μL of each sample's cell lysate was analyzed for luciferase activity as previously described [Brasier, et al. (1989) BioTechniques 7:1116–1122]. Protein was determined by the Bradford method (Bio-Rad kit). The results were expressed as the integrated light units (ILU)/mg protein. All measurements were done in duplicate and averaged.

ii) Assay For β-galactosidase Activity

Individual HuH7 and HepG2 cells expressing β-galactosidase were identified as previously described [Lim and Chase (1989) *Biotechniques* 7:576–579]. Briefly, cells transfected with the pCMV lac Z II plasmid were thoroughly washed with PBS, fixed (in the six well plates) with a solution of 0.5% glutaraldehyde in PBS for 10 min, washed again, then incubated in a solution containing 0.5% X-gal (BM) for 4.5 hrs at 37° C. Cells were then lightly counter-stained with Nuclear Fast Red. Blue colored cells were identified and photographed through a phase-contrast inverted light microscope. Efficiency was calculated by number of clearly blue cells in one hundred cells counted.

iii) Assay For Human Factor IX Production

Human Factor IX (hFIX) was expressed following transfection in HepG2 cells and excreted into the growth media. HepG2 cells do not express endogenous human Factor IX. HuH7, HepG2 (high) and HepG2 (low) cells were transfected as described above, with the appropriate positive and negative controls. Media was collected at days 1, 2, and 5 and assayed by ELISA for the presence of hFIX. Standards, ranging in concentration from 0.2 to 1 ng/ml were prepared using purified human plasma Factor IX (American Diagnostics, Inc., Greenwich, Conn.). ELISA plates were coated with the capturing monoclonal mouse IgG derived anti-human plasma Factor IX (Hematological Tech., Eessex, Vt.) and incubated at 4° C. the night before assay. The next day, the plates were thoroughly rinsed with PBS containing 0.1% Tween-20 PB and blocked with 100 $\mu$L of RPMI medium (GibcoBRL) containing 10% FCS for 1 hour. Standards and 50 $\mu$L aliquots of media collected from transfected HuH7 and HepG2 cells were then added and incubated at room temperature for 2 hr. Following stringent wash (e.g., washing 3 times with 0.1% Tween 20 in PBS), 50 $\mu$L of primary antibody [rabbit IgG derived polyclonal anti-human plasma Factor IX (Cal. Biotech.)] diluted in 10% FCS RPMI 1:1,000 was added to the wells and incubated a room temperature for 1 hour. Following stringent wash, 50 $\mu$L of the diluted secondary antibody, a goat anti-rabbit IgG conjugated to horseradish peroxidase (BM) was added and the mixture was incubated for 1 hour at RT (a 1:2,000 dilution in RPMI containing 10% FCS was made). After the final wash, the horseradish peroxidase activity in each sample was assessed by OD measurement of the samples after incubation for 1 hour with tetramethyl benzidine dihydrochloride (TMBD). All assays were done in duplicate, and the results were expressed as ng/ml/one million cells.

iv) β-galactosidase/SEC-R Cytochemical Staining Co-localization

HuH7, HepG2 (high) and HepG2 (low) cells were plated in six well plates and transfected as described above. Fluorescein labeling was carried out with fluorescein isothiocyanate, as described previously [Mann and Fish (1972) *Methods of Enzymology* 26:28–42]. Briefly, the C1315 peptide (145 $\mu$g) was incubated with 1 mg of fluorescein isothiocyanate for 1 hr at room temperature. Following incubation, 10 mg/ml glycine was added to destroy excess reagent, the pH was adjusted to 6.0 by the addition of 1N HCl and the labeled peptide was then purified on a Sephadex G10 column (Bio-Rad).

Two days following transfection, cells were washed with Ca$^{2+}$/Mg$^{2+}$ PBS, incubated with 100 nM fluorescein labeled C1315 peptide and diluted in binding buffer (DMEM containing 50 mM Hepes, 0.1 mg/ml cytochrome c, 0.01% Tween 80, 2 mg/ml bovine serum albumin) at 4° C. Individual cells were imaged on a Zeiss axiovert 35 microscope at an excitation wavelength of 493.5 nm and a measurement wavelength of 530 nm. Digital images were captured by a cooled CCD camera model CH250 for 25 seconds (Photometrics, Ltd., Tucson, Ariz.) and quantified by a Nu 2000 camera controller board (Photometrics) with a Macintosh Quadra 900 configuration. Data was processed with Oncor image software (Oncor Imaging, Rockville, Md.).

Following measurement, the cells were rinsed repeatedly, and the plates marked for future reference of orientation. The cells were then assayed for β-galactosidase activity as described above, imaged on a phase contrast light microscope in the exact orientation used during fluorescein measurements. Photographs were taken to scale so as to assess fluorescein labeled C1315 binding to cells expressing β-galactosidase.

EXAMPLE 13

C1315 Peptide-Polylysine-DNA Complexes Efficiently Transfer Genes Into Hepatoma Cell Lines Hepatoma cell lines were transfected with C1315 peptide-polylysine-DNA complexes as described above. The transfected cells were analyzed for expression of the appropriate reporter gene using the assays described above. The results described below demonstrate that the C1315 peptide-polylysine-DNA complexes efficiently transferred genes to hepatoma cells.

a) Transfection Of HepG2 Cells With The pGL3 Luciferase Expression Plasmid

Various concentrations of C1315/polylysine-pGL3 DNA complexes were applied to HepG2 cells as described in Example 12. Transfection and expression were assessed by luciferase enzyme activity in cell extracts. Positive controls (described above) established the capability of both HepG2 (high) and HepG2 (low) cells to express the pGL3 gene product. Receptor mediated transfer peak averaged at 404, 376 +/−247,034 ILUs/mg protein between days 2 and 4, about 20 and 40 percent of the DNA/lipofectin and condensed DNA/lipofectin controls, respectively. Luciferase activity declined to background 10 days after transfection. Cells exposed to pGL3 condensed with unmodified polylysine (e.g., unassembled complexes) served as negative controls. The results are summarized in FIG. 23 and are reported as the mean±standard error of the mean.

Figure 23A:
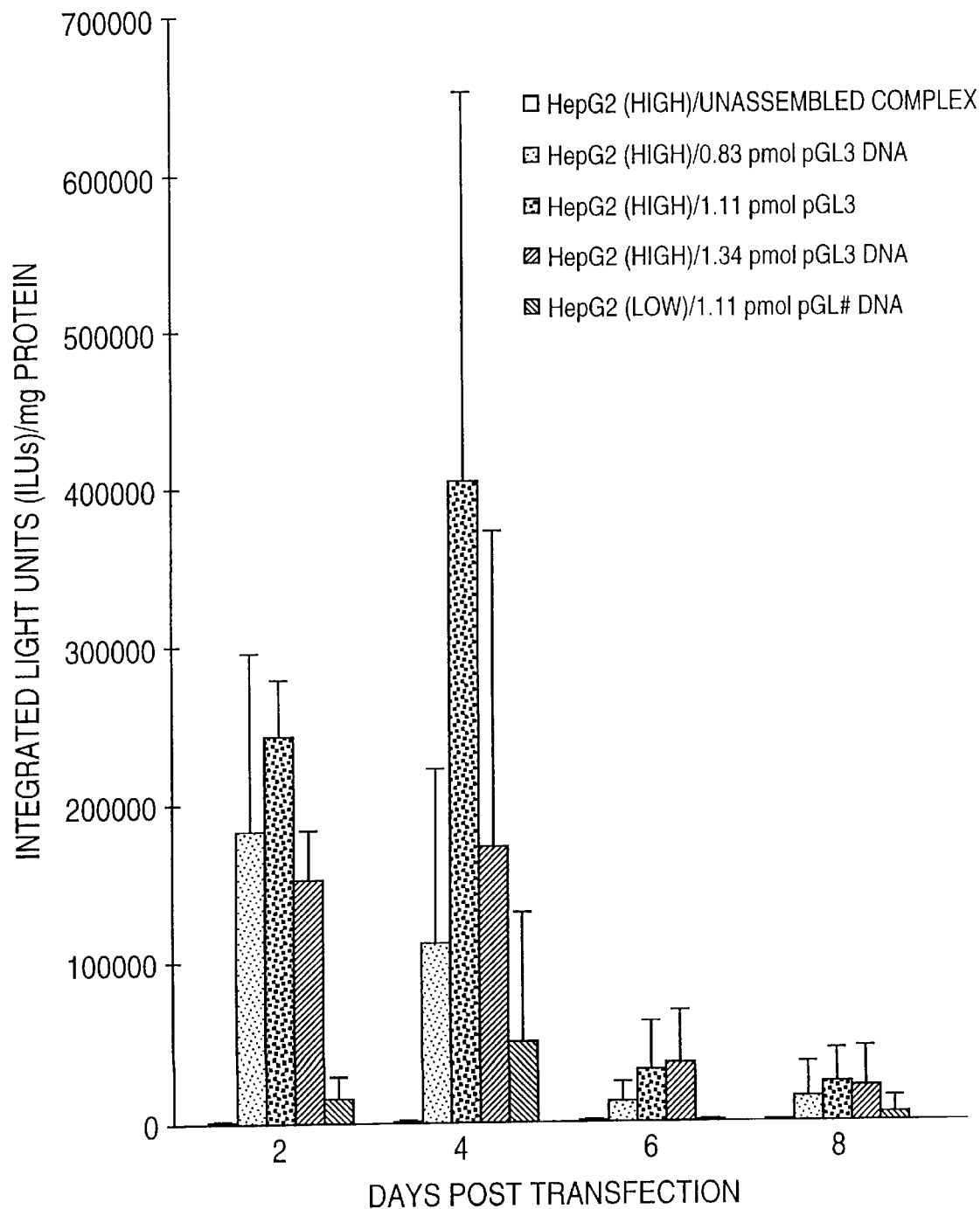

FIG. 23A demonstrates the dose dependence and time course of the transfection with the peptide based complex. In FIG. 23A, the number of ILUs/mg protein is plotted against the number of days post-transfection. For each time point shown, the results obtained from 1) HepG2 (high) cells transfected with unassembled complexes [e.g., unconjugated polylysine-condensed DNA (1.11 pmol) in the presence of 1.11 pmol each of free C1315 and LC sulfo SPDP linker], 2) HepG2 (high) cells transfected with 0.83 pmol pGL3 DNA complex, 3) HepG2 (high) cells transfected with 1.11 pmol pGL3 DNA complex, 4) HepG2 (high) cells transfected with 1.34 pmol pGL3 DNA complex, and 5) HepG2 (low) cells transfected with 1.11 pmol pGL3 DNA complex, are shown from left to right , respectively. In FIG. 23A, the values obtained from HepG2(high) cells 2 and 4 days post-transfection with each concentration of pGL3 complex tested represent a significant difference (P<0.05) compared to the values obtained from cells transfected with unassembled complexes. The values obtained from HepG2 (high) cells 2, 4 and 6 days post-transfection with each concentration of pGL3 complex tested represent a significant difference (P<0.05) compared to the corresponding transfected HepG2(low) cells. The values obtained from the pGL3-transfected HepG2(low) cells were not statistically different in comparison to the negative controls.

As seen in FIG. 23A, gene transfer was greatest with DNA content of 1.11 pmol per $5 \times 10^5$ cells in a 10 mm well. Complex concentrations either below or above the optimum concentration achieved less efficient transfer and expression [Wu and Wu (1991) *J. Biol Chem* 262:44299; Wu, et al. (1990) *J. Biol. Chem.* 266:14338; Ferkol, et al. (1995) *J. Clin. Invest.* 95:493; Perales, et al. (1994) *Proc. Natl. Acad. Sci. USA.* 91:4086]. HepG2 (low) cells were transfected by the complex with a much lower efficiency (FIG. 23A, solid black col). HepG2 (high) cells exposed to unconjugated polylysine-condensed DNA (1.11 pmol) in the presence of corresponding concentrations of free C1315 and LC sulfo SPDP linker were not transfected.

Figure 23B:
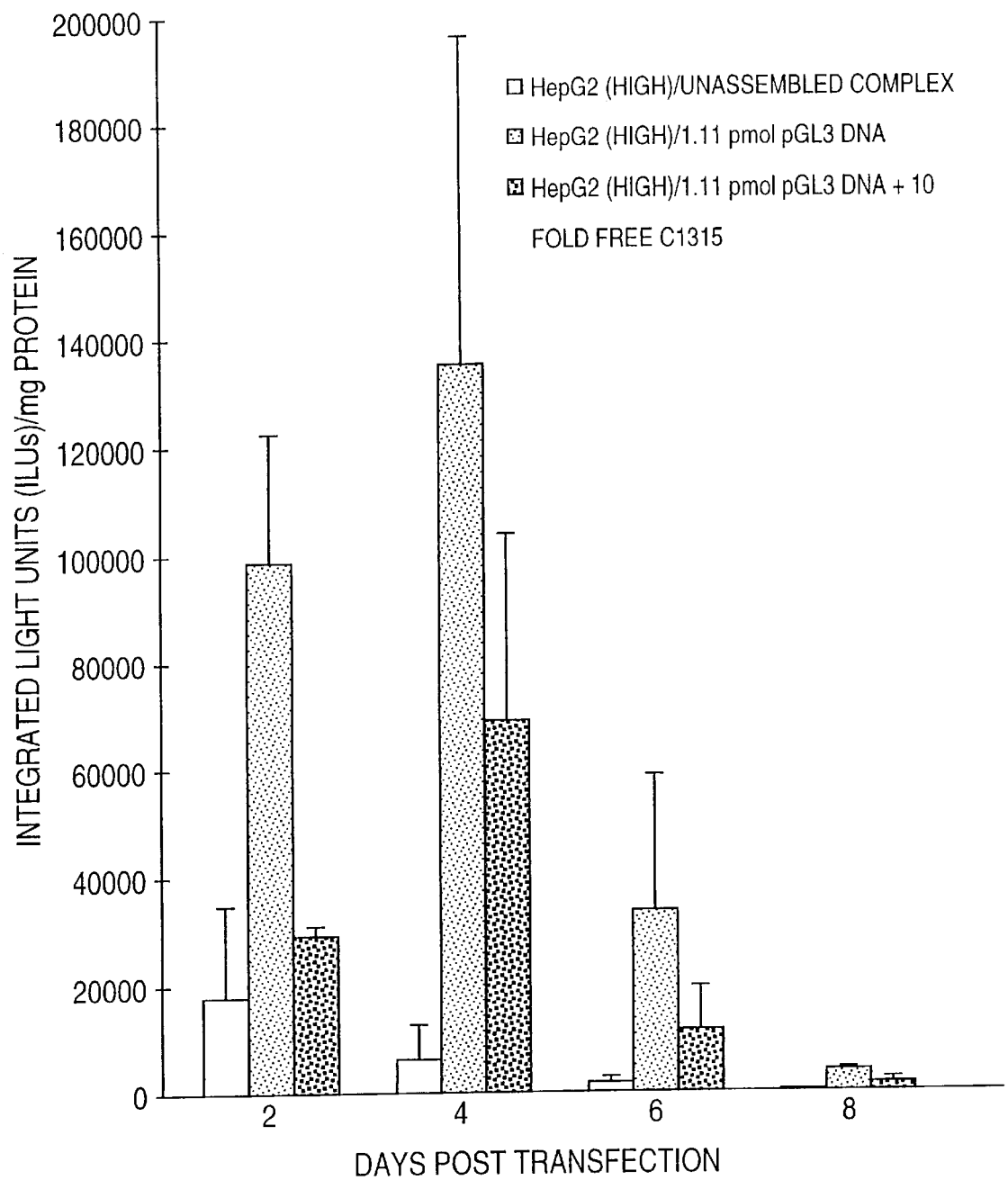

Addition of a 10 fold molar excess of free peptide at the time of transfection blocked uptake and expression by about 50%, as shown in FIG. 23B. Excess free peptide had no effect on cell viability. In FIG. 23B, the number of ILUs/mg protein are plotted against the number of days post-transfection. For each time point shown, the results obtained from 1) HepG2 (high) cells transfected with unassembled complexes [e.g., unconjugated polylysine-condensed DNA (1.11 pmol) in the presence of 1.11 pmol each of free C1315 and LC sulfo SPDP linker] (open col.), 2) HepG2 (high) cells transfected with 1.11 pmol pGL3 DNA complex (shaded col.) and, 3) HepG2 (high) cells transfected with 1.11 pmol pGL3 DNA complex in the presence of a 10-fold higher concentration of free C1315 peptide (solid col.) are displayed from left to right, respectively.

b) Transfection With The pCMV lac Z II-β-galactosidase Expression Plasmid

Both HuH7 and HepG2 cell lines were transfected with the pCMV lac Z II plasmid coding for the β-galactosidase protein as a complex with the C1315 peptide carrier or using Lipofectin®, as described above; three days after transfection, the cells were harvested and β-galactosidase activity was determined. The results (expressed as the mean±standard error of the mean) are summarized in Table 107. Cells staining blue represent cells expressing β-galactosidase; fluorescent cells represent cells which bound the fluoresceinated C105Y peptide. Cells which were counted as blue or fluorescent were intensely stained. The average % values represent the number of cells which were blue or fluorescent per 100 randomly selected cells. The results represent 6 independent experiments conducted. The cells were treated with either 1.1 1 pmol peptide carrier condensed pCMV Lac Z II ("peptide carrier complex") or 1.0 pmol pCMV Lac Z II mixed with Lipofectin® ("Lipofectin®")

As shown in Table 107, only HuH7 and HepG2 (high) cells, and not HepG2 (low), displayed substantial β-galactosidase staining. The pattern of staining varied with different DNA concentrations, correlating with luciferase expression. For both HuH7 and HepG2 (high), 1.11 pmol DNA/well produced the highest percentage of positive cells (Table 107). Non-specific Lipofectin® transfection of cells yielded, on average, twice the proportion of positive cells seen with our complex. DNA condensed with unconjugated C1315/poly-L-lysine failed to transfect any of the cells types. Positive cells were intensely stained and no background β-galactosidase activity was detected.

c) Transfer Of Human Factor IX To HepG2 Cells

The ability of C1315 peptide-polylysine-DNA complexes to deliver a clinically relevant gene was examined. HepG2 and HuH7 cells do not express endogenous human coagulation Factor IX. These cells were transduced cells with a plasmid coding for the human Factor IX gene and the amount of Factor IX secreted into growth media was measured 4 days later (using the assay described in Ex. 12). The media did not interfere with the ELISA assay for Factor IX. FIG. 24 illustrates the results (expressed as the mean±standard error of the mean) obtained from 24 experiments.

In FIG. 24, the amount of Factor IX secreted per $1 \times 10^6$ transfected cells is plotted against the cell type employed. For each cell line used, the amount of Factor IX expressed by cells receiving either: 1) unassembled complexes (open col.); 2) 0.83 pmol carrier condensed pFIX; and 3) 1.11 pmol carrier condensed pFIX (solid col.) is shown. When transfected with 1.11 pmol carrier condensed DNA, HuH7 cells produced 7.01+/−3.34 ng/mL, while HepG2 (high) cells produced 5.07+/−3.57 ng/mL human Factor IX. As with previous expression systems (e.g., expression plasmids containing the lac Z gene), HepG2 (low) cells expressed minimal amounts of protein peaking at 0.86 ng/mL human Factor IX with 1.11 pmol carrier condensed DNA. Again unconjugated poly-L-lysine condensed DNA failed to transduce any of the cells types. The transfected HuH7 and HepG2 (high) cells expressed levels of human Factor IX which were statistically significant in comparison to the levels expressed by transfected HepG2(low) cells.

c) Co-localization Of SEC-R And β-galactosidase Expression

A set of experiments were designed to permit the co-localization of the reporter gene product with the SEC receptor in transfected cells. Cytochemical staining for the receptor with fluoresceinated C1315 peptide revealed that only some cells in cultures of HuH7, HepG2 (high), and HepG2 (low) cells, bind detectable amounts of the ligand (shown in Table 107). Only those HepG2 (high) and HuH7 cells which bound the fluoresceinated peptide took up the complex, expressed the transgene, and stained positive for β-galactosidase expression. HepG2 (low) cells exhibiting minimal fluorescence did not stain positive for β-galactosidase. Furthermore, HuH7 cells bound the fluoresceinated peptide with less frequency than HepG2 (high) cells (Table 107). However, HuH7 binding as well as β-galactosidase expression was more intense. Cells treated with unfluoresceinated peptide or free fluorescein had no detectable autofluorescence.

The above results demonstrate that expression plasmids tightly condensed (18–25 nm in diameter) with polylysine conjugated to the C1315 peptide can be targeted to cells bearing the SEC receptor in vitro. The size of the peptide ligand as well as the repetitive nature of poly-L-lysine allow the coupling of the C1315 peptide to the poly-L-lysine to be assessed by NMR. Previous reports of receptor-mediated gene transfer have not determined the extent of conjugation. The nature of the present system has enabled us to estimate the extent of coupling and to verify the neutralization of reactive groups on unreacted SPDP using NMR. This is crucial since reactive cross-linking moieties might be toxic to cells. It was found that as few as one receptor ligand for every two poly-L-lysine molecules (69, and 138 ligands for each of the small and large plasmid DNA molecules, respectively) is sufficient to direct receptor-mediated gene transfer. Moreover, if the reaction conditions are set so that an excess of reactive sulfo LC SPDP moieties is added to poly-L-lysine, nearly all (85%) the added ligand is coupled to the polycation and the remaining SPDP groups are rendered inactive in the synthetic process. At the structural level, it was possible, using EM, to verify that tight condensation occurs. This data indicate that tightly condensed complexes are far more efficient for transfection than the aggregates, which form at lower NaCl concentrations as was reported by Ferkol et al. for the mannose receptor [*Proc. Natl. Acad. Sci. USA*. (1996) 93:101–105].

The above results demonstrate that gene transfer is mediated by the SEC-R and does not occur by nonspecific mechanisms. HepG2 (low) cells, which express few SEC-Rs, take up and express minimal levels of DNA (though they are capable of expressing the identical plasmid when it is delivered by lipofectin), whereas HuH7, and HepG2 (high) cells, which express abundant SEC-R, can be transduced with a 10 fold higher efficiency. This is true for all genes tested. In addition, a ten fold molar excess free ligand added at the time of transfection inhibited gene transfer by 50%, so receptor ligands apparently compete with the complex for receptor binding and uptake. HuH7, and HepG2 (high) cells transfected with DNA condensed with unmodified polylysine, in the presence or absence of free peptide did not exhibit gene expression, so uptake is not due to non-specific pinocytosis of condensed DNA particles. Cells shown by fluorescence to bind the C1315 peptide exhibit intense β-galactosidase activity, whereas cells which bind no fluorescent C13 15 do not express the lac Z gene. Moreover, intensity of cell fluorescence correlated with the intensity of β-galactosidase staining, indicating that cells expressing more SEC-R were capable of higher uptake of the complex. Only a fraction of cells in each of the populations studied bind C1315 peptide, indicating possible differential expression of the SEC receptor even within the same cell line. Successful delivery of three different reporter genes greatly reduces the likelihood of an artifact. Taken together, these data demonstrate that uptake and expression of the plasmid DNA gene is mediated through the SEC-R.

The above data demonstrate the specificity as well as success of gene transfer in vitro in cells that bear the SEC receptor. Gene transfer occurred in the presence of a tenfold molar excess of competitive ligand in vitro. Indeed, the peptides used as target binding moieties bind to the SEC-R with higher affinity than its natural ligands and therefore it is expected that serpin-protease complexes in vivo are unlikely to prohibit gene transfer.

SEC-R has been found in lung, liver, and brain [reviewed in Perlmutter (1994) *Pediatric Res.*, supra]; all of which exhibit severe disease in disorders for which the methods and compositions of the preset invention may be used for therapeutic treatment. Cells affected in α-1-antiprotease deficiency, the most common genetic cause of liver disease in children, and Alzheimer's disease express the SEC-R. Specific targeting of these cells using the methods and compositions of the present invention provides a means for gene therapy of these diseases.

Using the guidance provided in the Description of the Invention, as well as the experimental examples, pharmaceutical compositions comprising peptide-polycation carriers capable of binding to the SEC receptor coupled and condensed with the desired expression vector (e.g., a vector encoding α-1-antitrypsin) are administered to animals, including humans.

From the above it is clear that the present invention provides methods and compositions which permit the delivery of genes to cells expressing the SEC receptor.

TABLE 101

|  | Wu et al. | Wagner et al. | Present Invention* |
|---|---|---|---|
| [DNA] mg/ml | ~1 | ~0.01 | ~1 |
| PO$_4$/NH$_3$ Ratio | ~100 | ~1 | ~1.5 |
| Buffer | 150 mM NaCl | 10 mM Hepes (pH 7), 150 mM NaCl | Variable [NaCl] |
| Compaction Method | Annealing | Direct Mixing | Nucleation |
| Structure Of The DNA Complex | (Psi) | (Psi) or Uni-molecular | Unimolecular |
| Size Of The Complex | ≈200 nm | 80 nm | ~10 nm |
| Diagnostic Tools | Gel Retardation | Electron Microscopy | Circular Dichroism And Electron Microscopy |
| Expression in vivo | Yes | No | Yes |
| Length Of Expression | 6 Days | — | At Least 140 Days |

*Preferred Embodiment.

TABLE 102

Level Of Expression Of The PEPCK-hFIX Gene In The Livers Of Rats Injected With The DNA Complex

| Rat # | Days After Injection | Units Of hFIX Activity |
|---|---|---|
| 1 | 2 | 0.040 |
| 2 | 2 | 0.045 |
| 3 | 4 | 0.045 |
| 4 | 4 | 0.025 |
| 5 | 6 | 0.330 |
| 6 | 8 | 0.135 |
| 7 | 12 | 0.160 |
| 8 | 12 | 0.075 |
| 9 | 32 | 0.125 |
| 10 | 48 | 0.350 |
| 11 | 72 | 0.005 |
| 12 | 136 | 0.105 |

TABLE 103

| State Of DNA Or DNA/Polycation Complex | Naked Eye (Or Turdimetry At 400 nm) | Circular Dichroism | Electron Microscopy | Absorbance At 260 nm |
|---|---|---|---|---|
| Normal DNA (not complexed). | No turbidity. Clear solution. | Normal DNA spectrum, i.e., maxima at 220 and 269 nm; a minimum at 245 nm, and a zero-point crossover at 258 nm. | Very thin (about 1 nm thick or less) and long (about 300–1,000 nm) fibers. (FIG. 1B). | This absorbance is the reference for the other states. |
| Condensed complex (caused by polycation). | Low turbidity. Almost clear solution. | Identical to the spectrum of unbound (no poly-L-lysine) | Individually isolated spherical or toroidal | About 20–30% of reference absorbance. |

TABLE 103-continued

| State Of DNA Or DNA/Polycation Complex | Naked Eye (Or Turdimetry At 400 nm) | Circular Dichroism | Electron Microscopy | Absorbance At 260 nm |
|---|---|---|---|---|
| | | double stranded DNA in solution; positive maxima at 269 nm and very little contribution from the amide bond of the poly-L-lysine peptide to the spectrum at 220 nm. (FIG.1A). | structures. For DNA of about 5 kb, the toroids are about 10–20 nm in external diameter. Larger DNA, will of course compact to form larger toroids. Electron dense particles. No fibers. (FIG. 1D). | |
| Relaxed complex (caused by excess salt). | No turbidity. Clear solution. | Very difficult to differentiate from the condensed form. The only difference is that there is some contribution from the amide bond of the poly-L-lysine peptide to the spectrum at 220 nm. (FIG. 1A). | Rod-like fibers (usually 10–20 times the diameter of a naked DNA fiber, i.e., usually 10–20 nm thick, and longer than 60 nm) of DNA and branched toroidal structures of increased size. (FIG. 1F). | About 80–100% of reference absorbance. |
| Precipitated complex (caused by polycation if insufficient salt). | DNA fibers in solution. | Flat spectrum. (FIG. 1I). | Complex of macroscopic (micrometer range) DNA fibers. | About 1% of reference absorbance. |
| Unimolecular aggregated complex. | Highly variable from fine particulate to highly turbid. | Characteristic red-shift and positive ellipticity in the 300–320 nm band. | Unimolecular toroidal structures clumping together to form random networks of heterogeneous size and shape. | About 10-20% of reference absorbance. |
| Multimolecular aggregated complex (caused by polycation if insufficient salt).[1] | Clear. | Characteristic inversion in the spectrum maxima at 269 nm to the negative. Clear contribution from the amide bonci of the poly-L-lysine peptide to the spectrum at 220 nm. (FIG. 1H). | Isolated, multimolecular Toroidal structures of variable size depending on the number of DNA molecules condensed together. The size is usually approximately 10 to 70 times that of the unimolecular toroids. (See Wagner et al. and Shapiro et al.). (FIG. 1G). | About 100% of reference absorbance. |

[1] the DNA will aggregate into multimolecular complexes when the concentration of poly-L-lysine is increases suddenly in the DNA solution (i.e., by adding poly-L-lysine very rapidly to the vortexing solution of DNA) or the direct mixing of DNA and poly-L-lysine as in the method of Shapiro also used by Wagner et al.,
Aggregation into multimolecular complexes will be also the result of annealing both components (poly-L-lysine and DNA) in a gradient of decreasing NaCl concentration (i.e., the method of Wu and Wu).

TABLE 104

| Lys# | DNA (% super-coiled) | Initial [NaCl] | Final [NaCl] | [DNA] (mg/ml) | Physical State* | Activity |
|---|---|---|---|---|---|---|
| 15* | CMV-βGal (50) | 151.6 | 200 | 0.2 | CN: ND<br>EL: ND<br>Turbidity: None | + |
| 20* | MT-hGH (100) | 0 | 267 | 0.85 | CD: ND<br>EL: Relaxed<br>Turbidity: None | – |
| 27* | PEPCK-hLDLR (100) | 178 | 439 | 1 | CD: ND<br>EL: Condensed<br>Turbidity: Low | +++ |
| 56 | RS-Tr (50) | 803 | 1000 | 0.24 | CD: ND<br>EL: ND<br>Turbidity: None | ND |
| 56 | CMV-βGal (50) | 250 | 746 | 0.2 | CD: ND<br>EL: ND<br>Turbidity: Low | ND |
| 56* | PEPCK-hFIX (50) | 800 | 933 | 0.35 | CD: ND<br>EL: Condensed<br>Turbidity: Low | +++ |
| 56* | PEPCK-hFIX (50) | 636 | 970 | 0.6 | CD: ND<br>EL: ND<br>Turbidity: Low | +++ |
| 109* | CMV-βGal (50) | 500 | 909 | 0.2 | CD: +<br>EL: ND<br>Turbidity: Low | +++ |
| 109* | CMV-βGal (50) | 689 | 1000 | 0.39 | CD: ND<br>EL: ND<br>Turbidity: None | ND |

TABLE 104-continued

| Lys# | DNA (% super-coiled) | Initial [NaCl] | Final [NaCl] | [DNA] (mg/ml) | Physical State* | Activity |
|---|---|---|---|---|---|---|
| 109* | CMV-βGal (50) | 616 | 1036 | 0.95 | CD: ND<br>EL: ND<br>Turbidity: Low | +++ |
| 109* | CMV-βGal (50) | 735 | 941 | 0.39 | CD: ND<br>EL: ND<br>Turbidity: Low | +++ |
| 109* | CMV-βGal (50) | 500 | 1031 | 0.7 | CD: +<br>EL: ND<br>Turbidity: Low | ND |
| 109 | PEPCK-βGal (50) | 617 | 1004 | 0.3 | CD: ND<br>EL: ND<br>Turbidity: None | − |
| 109* | PEPCK-βGal (50) | 1085 | 1174 | 0.88 | CD: ND<br>EL: ND<br>Turbidity: Low | +++ |
| 109* | PEPCK-hFIX (50) | 630 | 1063 | 0.8 | CD: +<br>EL: Condensed<br>Turbidity: Low | +++ |
| 109 | PEPCK-hFIX (50) | 636 | 970 | 0.26 | CD: ND<br>EL: ND<br>Turbidity: None | ND |
| 109 | PEPCK-hFIX (50) | 750 | 1120 | 0.8 | CD: ND<br>EL: Relaxed<br>Turbidity: None | ++ |
| 109* | PEPCK-hFIX (50) | 812 | 1098 | 0.7 | CD: ND<br>EL: Condensed<br>Turbidity: Low | +++ |
| 109 | PEPCK-hFIX (50) | 812 | 1127 | 0.69 | CD: ND<br>EL: Relaxed<br>Turbidity: None | ++ |
| 109* | SV40-luc (80) | 1091 | 1144 | 0.9 | CD: ND<br>EL: Condensed<br>Turbidity: Low | +++ |
| 109* | SV40-luc (80) | 1091 | 1144 | 0.9 | CD: ND<br>EL: Condensed<br>Turbidity: Low | +++ |
| 109* | SV40-luc (80) | 961 | 1140 | 0.88 | CD: ND<br>EL: ND<br>Turbidity: Low | +++ |
| 109* | SV40-luc (80) | 1091 | 1144 | 0.8 | CD: ND<br>EL: ND<br>Turbidity: Low | +++ |
| 109 | SV40-luc (80) | 666 | 1000 | 0.19 | CD: +<br>EL: Relaxed<br>Turbidity: None | ND |
| 109* | SV40-luc (80) | 961 | 1121 | 0.8 | CD: ND<br>EL: ND<br>Turbidity: None | +++ |
| 109* | SV40-luc (80) | 735 | 972 | 0.55 | CD: ND<br>EL: ND<br>Turbidity: Low | +++ |
| 109* | Salmon sperm DNA (0) | 900 | 1231 | 1 | CD: ND<br>EL: ND<br>Turbidity: None | ND |
| 109 | PEPCK-OTC (50) | 774 | 948 | 0.9 | CD: ND<br>EL: ND<br>Turbidity: Low | ND |
| 123 | SV40-luc (100) | 719 | 1044 | 0.95 | CD: ND<br>EL: Relaxed<br>Turbidity: None | − |
| 123 | SV40-luc (100) | 905 | 1086 | 1 | CD: ND<br>EL: Relaxed<br>Turbidity: None | − |
| 123 | SV40-luc (100) | 689 | 1019 | 0.95 | CD: ND<br>EL: ND<br>Turbidity: None | − |
| 123 | SV40-luc (100) | 783 | 978 | 0.5 | CD: ND<br>EL: ND<br>Turbidity: None | − |
| 123 | SV40-luc (100) | 905 | 1149 | 0.57 | CD: ND<br>EL: Relaxed<br>Turbidity: None | − |
| 123* | CMV-13Gal (ND) | 825 | 1020 | 0.76 | CD: ND<br>EL: ND<br>Turbidity: None | ND |
| 150* | CMV-βGal (ND) | 886 | 1077 | 0.5 | CD: ND | +++ |

TABLE 104-continued

| Lys# | DNA (% super-coiled) | Initial [NaCl] | Final [NaCl] | [DNA] (mg/ml) | Physical State* | Activity |
|---|---|---|---|---|---|---|
| 150* | SV40-luc (80) | 800 | 972 | 0.36 | EL: Condensed Turbidity: Low CD: ND | +++ |
| 150 | SV40-luc (80) | 821 | 868 | 0.3 | EL: ND Turbidity: Low CD: Psi DNA | − |
| 150* | SV40-luc (80) | 821 | 968 | 0.3 | EL: Aggregated Turbidity: High CD: + | +++ |
| 150 | SV40-luc (80) | 821 | 1071 | 0.3 | EL: Condensed Turbidity: Low CD: + | − |
| 240* | SV40-luc (80) | 711 | 1125 | 1 | EL: Relaxed Turbidity: None CD: ND | +++ |
| 240 | SV40-luc (80) | 711 | 1162 | 1 | EL: Condensed Turbidity: Low CD: ND | + |
| 240 | SV40-luc (80) | 711 | 1280 | 1 | EL: Relaxed Turbidity: Low CD: ND | − |
| 240 | SV40-luc (80) | 800 | 1007 | 1 | EL: Relaxed Turbidity: None CD: ND | − |
| 240 | T7-T7 (90) | 708 | 1187 | 0.9 | EL: Aggregated Turbidity: High CD: + | ND |
| 240 | T7-T7 (90) | 708 | 1250 | 0.9 | EL: Condensed Turbidity: Low CD: + | − |
| 240 | PEPCK-hLDLR (100) | 642 | 947 | 0.73 | EL: Relaxed Turbidity: None CD: Psi DNA EL: Aggregated Turbidity: None | − |
| 240 | PEPCK-OTC (50) | 706 | 1174 | 0.35 | CD: ND EL: ND Turbidity: None | ND |
| 240 | PEPCK-OTC (50) | 898 | 1153 | 0.64 | CD: ND EL: ND Turbidity: None | ND |

Used in compiling Table 105.
ND = Not determined.
**Physical state of the DNA complex after polycation binding.
1. When circular dichroism (CD) was determined the results are indicated as follows: spectral changes due to the polycation condensation of DNA are insignificant (+); polycation condensation resulted in Psi-form DNA due to aggregation into multimolecular complexes (either rod-like or toroidal) (Psi DNA); appearance of an aberrant spectrum associated with a highly aggregative state (−).
2. Electron microscopic results have been indicated as follows: the association of the polycation with the DNA results in aggregation into complexes of increased size (>60 nm) (Aggregated); the structures resulting from the condensation are rod-like relaxed toroids of increased size (Relaxed); polycation binding results in proper condensation (toroids <30 nm in diameter) (Condensed). The number of properly condensed structures (toroids) per microscopic field has not been determined. There is approximately 3-fold variation in the number of toroids visible in the EL with different preparations of DNA complex.
3. Turbidity measurements are based on visual inspection of the final solution of DNA complex.
†A relative indication of the activity of the introduced gene after introduction of the DNA complex:
hFIX (human factor IX) is measured by the western blot hybridization or by a functional activity assay of rat plasma samples.
βGal (β-galactosidase) activity is measured by in situ histochemistry in fixed cells or tissue sections.
luc (luciferase) activity is measured using a specific enzyme activity assay with tissue extracts.
hLDLR (human LDL receptor) activity was measured indirectly after determination of the total serum cholesterol levels in a rabbit model for LDL receptor deficiency.
hGH (human growth hormone) activity refers to a direct measurement of hGH levels in the serum of animals transfected with the DNA complex. A radio-immunoassay specific for hGH was used.
The activity is relative to all the experiment performed with the same DNA. Not detectable activity after introduction of the DNA complex is indicated by "−".

TABLE 105

Final [NaCl] = 555.75 + [DNA] mg/ml * 180.91 + log (lys length) * y18.32

Regression Statistics

| | |
|---|---|
| Multiple R: | 0.881909585 |
| R Square: | 0.777764515 |
| Adjusted R Square: | 0.743574441 |
| Standard Error: | 135.5087624 |
| Observations: | 16 |

Analysis of Variance

| | df | Sum of Squares | Mean Square | F | Significance F |
|---|---|---|---|---|---|
| Regression | 2 | 835435.3166 | 417717.6583 | 22.748254 | 5.6792 E−05 |
| Residual | 13 | 238714.1209 | 18362.62469 | | |
| Total | 15 | 1074149.438 | | | |

| | Coefficients | Standard Error | t Statistic | P-value | Lower 95% |
|---|---|---|---|---|---|
| Intercept | −555.757861 | 228.34416556 | 2.433887324 | 0.0279103 | −1049.059922 |
| [DNA]mg/ml | 180.9113279 | 125.4285365 | 1.442345841 | 0.1697596 | −90.06049864 |
| log (lys length) | 718.3211054 | 117.7844848 | 6.098605488 | 2.037 E−05 | 463.8632453 |

TABLE 106

Estimated And Experimental Size Of Condensed DNA Complexes

| | | Condensed Diameter (nm ± SD) | | |
|---|---|---|---|---|
| DNA | Size(bp) | Electron Microscope[a] | Hydrated Model (Partial Specific Volume)[b] | Hydrated Model (X-Ray Diffraction Density)[c] |
| PEPCK-hFIX | 4,500 | 12.80 ± 1.56 | 18 | 22 |
| PEPCK-hOTC | 5,300 | 18.00 ± 1.83 | 20 | 23 |
| SV40-luciferase | 5,600 | 16.95 ± 3.50 | 20 | 24 |
| PEPCK-CAT | 5,800 | 16.30 ± 2.56 | 20 | 25 |
| CMV-hLDLr | 7,400 | 20.70 ± 2.60 | 22 | 26 |
| φ29[d] | 18,000 | 38[e] | 40 | 47 |

[a]measured diameter of at least 10 DNA complexes in a printed photograph (×240,000).
[b]calculated diameter of a unimolecular DNA complex assuming a condensed sphere. The partial specific volume of Na-DNA was deemed to be 0.5 ml/g. The contribution of galactosylated poly-L-lysine at a charge ratio of 1:1 has been added. The molecular weight of DNA was calculated based on an average molecular weight of 6,500 dalton/10 bp. The formula used is:DNA molecular weight (daltons)/6.023 × $10^{23}$ × 0.5(ml/g) = ml occupied by a molecule of DNA of X molecular weight. Diameter obtained from the formula for the volume of a sphere.
[c]calculated diameter of a unimolecular DNA complex assuming a condensed sphere. The calculation assumed a hydrated density of 1.25 ± 0.1 g/ml as determined by X-ray diffraction. The contribution of a galactosylated poly-L-lysine at a charge ratio of 1:1 has been added. The molecular weight of DNA was calculated based on an average molecular weight of 6,500 dalton/10 bp. The formula is:DNA molecular weight (daltons)/6.023 × $10^{23}$/1.25 (g/ml) = ml occupied by a molecular of DNA of X molecular weight. Diameter obtained from the formula for the volume of a sphere.
[d]from the literature.
[e]the size to the phage prohead includes the protein out-shell.

TABLE 107

| Cell Line | Average % Blue Cells (Treatment) | Average % Fluorescent Cells |
|---|---|---|
| HepG2(high) | 11.3 ± 5.5 (Peptide Carrier Complex) | 20.4 ± 11.2 |
| | 34.8 ± 6.7 (Lipofectin ®) | |
| HuH7 | 5.0 ± 3.7 (Peptide Carrier Complex) | 14.3 ± 4.0 |
| | 14.7 ± 3.6 (Lipofectin ®) | |
| HepG2(low) | 1.0 ± 0.9 (Peptide Carrier Complex) | 1.8 ± 1.4 |
| | 9.7 ± 1.6 (Lipofectin ®) | |

We claim:

1. A method for making a composition for delivering an oligonucleotide to a mammalian cell, comprising the steps of:
   (a) providing:
      i) a target binding moiety comprising a peptide having the amino acid sequence set forth in SEQ ID NO: 28, said target binding moiety being capable of binding to a serpin enzyme complex receptor;
      ii) a nucleic acid binding moiety comprising polylysine;
      iii) a vector comprising an oligonucleotide encoding one or more gene products;
   b) conjugating said target binding moiety to said nucleic acid binding moiety to form a carrier;
   c) coupling said vector with said carrier to form a composition which is able to bind to said receptor and deliver said expression vector to a mammalian cell having said receptor on its exterior surface.

2. The method of claim 1, wherein said expression vector further comprises a promoter sequence operably linked to said oligonucleotide encoding one or more gene products.

3. The method of claim 2, wherein said promoter sequence is derived from a mammalian gene.

4. The method of claim 2, wherein said promoter sequence is a viral promoter sequence.

5. The method of claim 4, wherein said viral promoter sequence is selected from the group consisting of the simian virus 40 promoter, the Moloney murine leukemia virus promoter and the cytomegalovirus promoter.

6. The method of claim 1 wherein said expression vector is compacted.

7. The method of claim 1 wherein said target binding moiety is a peptide comprising an amino acid sequence set forth in SEQ ID NO: 28.

8. The method of claim 7 wherein said target binding moiety is a peptide comprising the amino acid sequence set forth in SEQ ID NO: 31.

9. The method of claim 1 wherein said nucleic acid binding moiety is a polycation.

10. The method of claim 9 wherein said polycation is poly-L-lysine.

11. A method for delivering an oligonucleotide to a mammalian cell, comprising the steps of:

(a) providing:

i) a target binding moiety comprising a peptide having the amino acid sequence set forth in SEQ ID NOS: 28, said target binding moiety being capable of binding to a serpin enzyme complex receptor;

ii) a nucleic acid binding moiety comprising polylysine;

iii) a vector comprising an oligonucleotide encoding one or more reporter gene products;

iv) a mammalian cell having on its exterior surface a serpin enzyme complex receptor;

b) conjugating said target binding moiety to said nucleic acid binding moiety to form a carrier;

c) coupling said vector with said carrier to form a composition; and d) contacting said mammalian cell with said composition under conditions such that said composition binds to said receptor and results in delivery of said vector to the interior of said mammalian cell.

12. The method of claim 11 wherein said mammalian cell is located in a recipient animal.

13. The method of claim 12, wherein said mammalian cell is selected from the group consisting of hepatocytes, mononuclear phagocytes, neutrophils, intestinal epithelial cells, glial cells and neuronal cells.

14. The method of claim 12, wherein said contacting of said mammalian cell with said composition comprises administrating said composition to said recipient animal.

15. The method of claim 14, wherein said administering comprises injection of an aqueous solution containing said composition into said recipient animal.

16. The method of claim 14, wherein said injection is intravenous injection.

17. The method of claim 12, wherein said recipient animal is a human.

18. The method of claim 11 further comprising following contacting said mammalian cell with said composition, examining said contacted cell for the expression of said one or more reporter gene products encoded by said expression vector.

19. The method of claim 15 further comprising following injection of said composition, examining tissues in said recipient animal for the expression of said one or more reporter gene products encoded by said expression vector.

20. The method of claim 11 wherein the target binding moiety consists of a peptide which comprises the sequence set forth in SEQ ID NO: 28.

21. The method of claim 11 wherein the target binding moiety comprises a peptide which comprises the sequence set forth in SEQ ID NO: 31.

22. The method of claim 11 wherein the target binding moiety consists of a peptide which comprises the sequence set forth in SEQ ID NO: 31.

* * * * *

UNITED STATES PATENT AND TRADEMARK OFFICE
CERTIFICATE OF CORRECTION

PATENT NO.: 5,972,901
DATED: October 26, 1999
INVENTOR(S): Thomas W. Ferkol, Jr., et al.

It is certified that the errors appear in the above-identified patent and that said Letters Patent is hereby corrected as shown below:

On the Title Page:
In item [75] Inventors:

Insert --David Perlmutter, St. Louis, MO--.

In Claim 5, column 98, line 48:

After "promoter" insert --,--.

In Claim 13, column 99, line 20:

After "cells" insert --,--.

Signed and Sealed this

Third Day of April, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
    (A) LENGTH: 16 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO:1:

Tyr Tyr Pro Asp Thr Ser Val Asn Arg His Thr Arg Lys Tyr Trp Cys
1               5                   10                  15

(2) INFORMATION FOR SEQ ID NO:2:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AAGAAGAAGA AAAAAA                                                16

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CTTCTTCTTC TTCTTTTTT                                             19

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GACATTGTGA TGACYCARTC T                                          21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CAAAWTGTKC TCACCCAGTC T                                          21

(2) INFORMATION FOR SEQ ID NO:6:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:6:

GATGTTKTGA TGACCCAAAC T                                              21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GATATTGTGA TAACCCAGGM T                                              21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GACATCSAGA TGACYCAGTC T                                              21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GAYATTGTGM TGACMCAGTC T                                              21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TTTTATCTCC AGCTTKGTSC C                                              21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:11:

CAGGTGCAGC TKMAGGAGTC A                                    21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CAGGTCCARC TGCAGCAGYC T                                    21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GARGTGAAGC TGGTCGARTC T                                    21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GAGGTTCAGC TTCAGCAGTC T                                    21

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TCAGGAGACT GTGAGAGTGG TGCCTTGRCC CCA                        33

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGCCCAAGCT TGCCACCATG GACATTGTGC TG                         32

(2) INFORMATION FOR SEQ ID NO:17:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ACCGGATCCG CCACCGCCCG AGCCACCGCC TCCTTTTATC TCCAGCTTTG TGCC      54

(2) INFORMATION FOR SEQ ID NO:18:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:18:

Gly Gly Gly Gly Ser Gly Gly Gly Gly Ser Gly
1            5                 10

(2) INFORMATION FOR SEQ ID NO:19:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TCGGGCGGTG GCGGATCCGG TGGCGGCGGC TCTGAGGTTC AGCTTCAGCA GTCT      54

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:20:

Ser Gly Gly Gly Gly Ser Gly Gly Gly Gly Ser
1            5                 10

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CCTAGTCTAG ACTTACATCG ATGAGGAGAC TGTGAGAGTG GTGCC      45

(2) INFORMATION FOR SEQ ID NO:22:

(i) SEQUENCE CHARACTERISTICS:

(A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GACCCATCGA TGGCCAGATA CCGATGCTGC                                            30

(2) INFORMATION FOR SEQ ID NO:23:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CCTAGTCTAG ATAAGCTTCT AGTATTTTTT ACACCTTAT                                  39

(2) INFORMATION FOR SEQ ID NO:24:

(i) SEQUENCE CHARACTERISTICS:
        (A) LENGTH: 906 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..906

(xi) SEQUENCE DESCRIPTION: SEQ ID NO:24:

ATG GAC ATT GTG CTG ACC CAG TCT CCA GCT TCT TTG GCT GTG TCT CTA             48
Met Asp Ile Val Leu Thr Gln Ser Pro Ala Ser Leu Ala Val Ser Leu
 1               5                  10                  15

GGG CAG AGG GCC ACC ATC TCC TGC AGA GCC AGC GAA AGT GTT GAT AAT             96
Gly Gln Arg Ala Thr Ile Ser Cys Arg Ala Ser Glu Ser Val Asp Asn
             20                  25                  30

TAT GCC ATT AGT TTT ATG AAC TGG TTC CAA CAG AAA CCA GGA CAG CCA            144
Tyr Ala Ile Ser Phe Met Asn Trp Phe Gln Gln Lys Pro Gly Gln Pro
         35                  40                  45

CCC AAA CTC CTC ATC TAT GCT GCA TCC AAC CAA GGA TCC GGG GTC CCT            192
Pro Lys Leu Leu Ile Tyr Ala Ala Ser Asn Gln Gly Ser Gly Val Pro
     50                  55                  60

GGC AGG TTT AGT GGC AGT GGG TCT GGG ACA GAC TTC AGC CTC AAC ATC            240
Gly Arg Phe Ser Gly Ser Gly Ser Gly Thr Asp Phe Ser Leu Asn Ile
 65                  70                  75                  80

CAT CCT ATG GAG GAG GAT GAT ACT GCA ATG TAT TTC TGT CAG CAA AGT            288
His Pro Met Glu Glu Asp Asp Thr Ala Met Tyr Phe Cys Gln Gln Ser
                 85                  90                  95

AAG GCG GTT CCG TAC ACG TTC GGA GGG GGC ACA AAG CTG GAG ATA AAA            336
Lys Ala Val Pro Tyr Thr Phe Gly Gly Gly Thr Lys Leu Glu Ile Lys
            100                 105                 110

GGA GGC GGT GGC TCG GGC GGT GGC GGA TCC GGC GGC GGC TCT GAG GTT            384
Gly Gly Gly Gly Ser Gly Gly Gly Ser Gly Gly Gly Ser Glu Val
        115                 120                 125

CAG CTT CAG CAG TCT GGA CCT GAC CTG GTG AAG CCT GGG GCT TCA GTG            432
Gln Leu Gln Gln Ser Gly Pro Asp Leu Val Lys Pro Gly Ala Ser Val
    130                 135                 140

AAG ATA TCC TGC AAG ACT TCT GGA TAC ACA TTC ATT GAA TAT ACC ATG            480

```
Lys Ile Ser Cys Lys Thr Ser Gly Tyr Thr Phe Ile Glu Tyr Thr Met
145                 150                 155                 160

CAC TGG GTG AAG CAG AGC CAT GGA AAG AGC CTT GAG TGG ATT GGA GGT        528
His Trp Val Lys Gln Ser His Gly Lys Ser Leu Glu Trp Ile Gly Gly
                165                 170                 175

ATT AAT CCT AAC AAT GGT GGT ACT AGT TAC AAC CAG AAG TTC AAG GGC        576
Ile Asn Pro Asn Asn Gly Gly Thr Ser Tyr Asn Gln Lys Phe Lys Gly
            180                 185                 190

AAG GCC ACA TTG ACT GTA GAC AAG TCC TCC ACC ACA GCC TAC ATG GAG        624
Lys Ala Thr Leu Thr Val Asp Lys Ser Ser Thr Thr Ala Tyr Met Glu
            195                 200                 205

CTC CGC GGC CTG ACA TCT GAG GAT TCT GCA GTC TAT TCC TGT GCA AGA        672
Leu Arg Gly Leu Thr Ser Glu Asp Ser Ala Val Tyr Ser Cys Ala Arg
        210                 215                 220

TAC TAT AGG TAC GAC GTT CTC TCT GCT ATG GAC TAC TGG GGC CAA GGC        720
Tyr Tyr Arg Tyr Asp Val Leu Ser Ala Met Asp Tyr Trp Gly Gln Gly
225                 230                 235                 240

ACC ACT CTC ACA GTC TCC TCA GGG CCC ACC ATG GCC AGA TAC CGA TGC        768
Thr Thr Leu Thr Val Ser Ser Gly Pro Thr Met Ala Arg Tyr Arg Cys
                245                 250                 255

TGC CGC ACC AAA AGC AGG AGC AGA TGC CGC CGT CGC AGG CGA AGA TGT        816
Cys Arg Thr Lys Ser Arg Ser Arg Cys Arg Arg Arg Arg Arg Arg Cys
                260                 265                 270

CGC AGA CGG AGG AGG CGA TGC TGC CGG CGG AGG AGG CGA AGA TGC TGC        864
Arg Arg Arg Arg Arg Arg Cys Cys Arg Arg Arg Arg Arg Arg Cys Cys
            275                 280                 285

CGT CGC CGC CGC TCA TAC ACC ATA AGG TGT AAA AAA TAC TAG                906
Arg Arg Arg Arg Ser Tyr Thr Ile Arg Cys Lys Lys Tyr *
        290                 295                 300
```

(2) INFORMATION FOR SEQ ID NO:25:

(i) SEQUENCE CHARACTERISTICS:
        (A) LENGTH: 301 amino acids
        (B) TYPE: amino acid
        (D) TOPOLOGY: linear (ii) MOLECULE TYPE: protein (xi) SEQUENCE DESCRIPTION: SEQ ID NO:25:

```
Met Asp Ile Val Leu Thr Gln Ser Pro Ala Ser Leu Ala Val Ser Leu
1               5                   10                  15

Gly Gln Arg Ala Thr Ile Ser Cys Arg Ala Ser Glu Ser Val Asp Asn
                20                  25                  30

Tyr Ala Ile Ser Phe Met Asn Trp Phe Gln Gln Lys Pro Gly Gln Pro
            35                  40                  45

Pro Lys Leu Leu Ile Tyr Ala Ala Ser Asn Gln Gly Ser Gly Val Pro
        50                  55                  60

Gly Arg Phe Ser Gly Ser Gly Ser Gly Thr Asp Phe Ser Leu Asn Ile
65                  70                  75                  80

His Pro Met Glu Glu Asp Asp Thr Ala Met Tyr Phe Cys Gln Gln Ser
                85                  90                  95

Lys Ala Val Pro Tyr Thr Phe Gly Gly Gly Thr Lys Leu Glu Ile Lys
                100                 105                 110

Gly Gly Gly Gly Ser Gly Gly Gly Ser Gly Gly Ser Glu Val
            115                 120                 125

Gln Leu Gln Gln Ser Gly Pro Asp Leu Val Lys Pro Gly Ala Ser Val
        130                 135                 140

Lys Ile Ser Cys Lys Thr Ser Gly Tyr Thr Phe Ile Glu Tyr Thr Met
145                 150                 155                 160
```

```
His Trp Val Lys Gln Ser His Gly Lys Ser Leu Glu Trp Ile Gly Gly
                165                 170                 175

Ile Asn Pro Asn Asn Gly Gly Thr Ser Tyr Asn Gln Lys Phe Lys Gly
            180                 185                 190

Lys Ala Thr Leu Thr Val Asp Lys Ser Ser Thr Thr Ala Tyr Met Glu
            195                 200                 205

Leu Arg Gly Leu Thr Ser Glu Asp Ser Ala Val Tyr Ser Cys Ala Arg
    210                 215                 220

Tyr Tyr Arg Tyr Asp Val Leu Ser Ala Met Asp Tyr Trp Gly Gln Gly
225                 230                 235                 240

Thr Thr Leu Thr Val Ser Ser Gly Pro Thr Met Ala Arg Tyr Arg Cys
                245                 250                 255

Cys Arg Thr Lys Ser Arg Ser Arg Cys Arg Arg Arg Arg Arg Arg Cys
                260                 265                 270

Arg Arg Arg Arg Arg Arg Cys Cys Arg Arg Arg Arg Arg Arg Cys Cys
                275                 280                 285

Arg Arg Arg Arg Ser Tyr Thr Ile Arg Cys Lys Lys Tyr
                290                 295                 300
```

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:26:

```
Gly Gly Gly Gly Ser Gly Gly Gly Gly Ser Gly Gly Gly Ser
1               5                   10
```

(2) INFORMATION FOR SEQ ID NO:27:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:27:

```
Gly Gly Gly Gly Ser Gly Gly Gly Ser Gly Gly Gly Gly Ser
1               5                   10                  15
```

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:28:

```
Phe Val Phe Leu Ile
1               5
```

(2) INFORMATION FOR SEQ ID NO:29:

(i) SEQUENCE CHARACTERISTICS:

```
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:29:

Phe Val Tyr Leu Ile
    1               5

(2) INFORMATION FOR SEQ ID NO:30:

(i) SEQUENCE CHARACTERISTICS:
            (A) LENGTH: 17 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:30:

Cys Ser Ile Pro Pro Glu Val Lys Phe Asn Lys Pro Phe Val Tyr Leu
    1               5                   10                  15

Ile (2) INFORMATION FOR SEQ ID NO:31:

(i) SEQUENCE CHARACTERISTICS:
            (A) LENGTH: 28 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:31:

Cys Phe Leu Glu Ala Ile Pro Met Ser Ile Pro Pro Glu Val Lys Phe
    1               5                   10                  15

Asn Lys Pro Phe Val Phe Leu Ile Ile His Arg Asp
                    20                  25
```